US010663761B2

(12) United States Patent
De Juan, Jr. et al.

(10) Patent No.: US 10,663,761 B2
(45) Date of Patent: May 26, 2020

(54) CONFORMABLE THERAPEUTIC SHIELD FOR VISION AND PAIN

(71) Applicant: Journey1, Inc., Brisbane, CA (US)

(72) Inventors: Eugene De Juan, Jr., San Francisco, CA (US); Cary J. Reich, Los Gatos, CA (US); Yair Alster, Palo Alto, CA (US); K. Angela MacFarlane, Mountain View, CA (US); Doug Rimer, Los Altos, CA (US); Douglas Sutton, Pacifica, CA (US); Dean Carson, Mountain View, CA (US); Enrique Barragan, Monterrey (MX); Matt Clarke, Mountain View, CA (US); Ashley Tuan, Mountain View, CA (US); Brian Levy, New York, NY (US)

(73) Assignee: JOURNEY1, INC., Brisbane, CA (US)

( * ) Notice: Subject to any disclaimer, the term of this patent is extended or adjusted under 35 U.S.C. 154(b) by 0 days.

(21) Appl. No.: 15/695,889

(22) Filed: Sep. 5, 2017

(65) Prior Publication Data
US 2018/0011341 A1    Jan. 11, 2018

Related U.S. Application Data

(60) Continuation of application No. 14/966,918, filed on Dec. 11, 2015, now Pat. No. 9,810,921, which is a
(Continued)

(51) Int. Cl.
*A61B 3/14*    (2006.01)
*A61B 3/00*    (2006.01)
(Continued)

(52) U.S. Cl.
CPC ............. *G02C 7/047* (2013.01); *A61F 2/145* (2013.01); *A61F 2/147* (2013.01); *A61F 9/008* (2013.01);
(Continued)

(58) Field of Classification Search
CPC .. A61B 3/14; A61B 3/156; A61B 3/12; A61B 3/145; A61L 27/18
(Continued)

(56) References Cited

U.S. PATENT DOCUMENTS 2,641,161 A    6/1953 Silverstein
2,714,721 A    8/1955 Stone, Jr. et al.
(Continued)

FOREIGN PATENT DOCUMENTS

CA    993401 A1    7/1976
CA    2174967 C    5/1995
(Continued)

OTHER PUBLICATIONS

Alio, Jorge L. et al. "Contact lens fitting to correct irregular astigmatism after corneal refractive surgery," Journal of Cataract & Refractive Surgery, vol. 28, No. 10, pp. 1750-1757, Oct. 2002.
(Continued)

*Primary Examiner* — Mohammed A Hasan
(74) *Attorney, Agent, or Firm* — Wilson Sonsini Goodrich & Rosati

(57) ABSTRACT

A conformable covering comprises an outer portion with rigidity to resist movement on the cornea and an inner portion to contact the cornea and provide an environment for epithelial regeneration. The inner portion of the covering can be configured in many ways so as to conform at least partially to an ablated stromal surface so as to correct vision. The conformable inner portion may have at least some rigidity so as to smooth the epithelium such that the epithelium regenerates rapidly and is guided with the covering so as to form a smooth layer for vision. The inner portion may comprise an amount of rigidity within a range from about 1×10-4 Pa*m3 to about 5×10-4 Pa*m3 so as to deflect and conform at least partially to the ablated cornea and smooth
(Continued)

an inner portion of the ablation with an amount of pressure when deflected.

16 Claims, 66 Drawing Sheets

Related U.S. Application Data division of application No. 14/286,605, filed on May 23, 2014, now Pat. No. 9,241,837, which is a continuation of application No. 13/894,176, filed on May 14, 2013, now Pat. No. 8,926,096, which is a continuation of application No. 13/503,842, filed as application No. PCT/US2010/053975 on Oct. 25, 2010, now Pat. No. 9,498,385.

(60) Provisional application No. 61/322,206, filed on Apr. 8, 2010, provisional application No. 61/279,613, filed on Oct. 23, 2009.

(51) Int. Cl.
*G02C 7/04* (2006.01)
*A61F 9/00* (2006.01)
*A61F 9/013* (2006.01)
*A61F 9/04* (2006.01)
*A61L 27/18* (2006.01)
*A61F 2/14* (2006.01)
*A61F 9/008* (2006.01)
*A61F 13/12* (2006.01)

(52) U.S. Cl.
CPC ........ *A61F 9/0017* (2013.01); *A61F 9/00804* (2013.01); *A61F 9/013* (2013.01); *A61F 9/0136* (2013.01); *A61F 9/04* (2013.01); *A61F 13/124* (2013.01); *A61L 27/18* (2013.01); *G02C 7/048* (2013.01); *G02C 7/049* (2013.01); *A61F 9/00* (2013.01); *A61F 9/00802* (2013.01); *A61F 2009/00853* (2013.01); *A61F 2009/00893* (2013.01); *A61F 2250/0029* (2013.01); *A61L 2430/16* (2013.01); *G02C 2202/06* (2013.01)

(58) Field of Classification Search
USPC ........................................................ 351/207
See application file for complete search history.

(56) References Cited

U.S. PATENT DOCUMENTS

| | | |
|---|---|---|
| 2,952,023 A | 9/1960 | Hyman et al. |
| 3,246,941 A | 4/1966 | Moss |
| 3,431,046 A | 3/1969 | Conrad et al. |
| 3,468,602 A | 9/1969 | Rosen et al. |
| 3,488,111 A | 1/1970 | Isen |
| 3,489,491 A | 1/1970 | Creighton |
| 3,495,899 A | 2/1970 | Biri |
| 3,594,074 A | 7/1971 | Rosen |
| 3,619,044 A | 11/1971 | Kamath |
| 3,688,386 A | 9/1972 | Pereira |
| 3,833,786 A | 9/1974 | Brucker |
| 3,915,609 A | 10/1975 | Robinson |
| 3,944,347 A | 3/1976 | Barkdoll et al. |
| 3,973,837 A | 8/1976 | Page |
| 3,973,838 A | 8/1976 | Deichert et al. |
| 4,037,866 A | 7/1977 | Price |
| 4,053,442 A | 10/1977 | Jungr et al. |
| 4,068,933 A | 1/1978 | Seiderman |
| 4,071,272 A | 1/1978 | Drdlik |
| 4,121,885 A | 10/1978 | Erickson et al. |
| 4,126,904 A | 11/1978 | Shepard et al. |
| 4,166,255 A | 8/1979 | Graham |
| 4,171,878 A | 10/1979 | Kivaev et al. |
| 4,194,815 A | 3/1980 | Trombley |
| 4,198,132 A | 4/1980 | Jacobson et al. |
| 4,200,320 A | 4/1980 | Durham |
| 4,208,362 A | 6/1980 | Deichert et al. |
| 4,211,476 A | 7/1980 | Brummel et al. |
| 4,268,131 A | 5/1981 | Miyata et al. |
| 4,268,133 A | 5/1981 | Fischer et al. |
| 4,312,575 A | 1/1982 | Peyman et al. |
| 4,346,482 A | 8/1982 | Tennant et al. |
| 4,381,007 A | 4/1983 | Doss |
| 4,407,766 A | 10/1983 | Haardt et al. |
| 4,452,776 A | 6/1984 | Refojo et al. |
| 4,452,925 A | 6/1984 | Kuzma et al. |
| 4,487,905 A | 12/1984 | Mitchell |
| 4,563,779 A | 1/1986 | Kelman et al. |
| 4,581,030 A | 4/1986 | Bruns et al. |
| 4,593,981 A | 6/1986 | Scilipoti |
| 4,621,912 A | 11/1986 | Meyer |
| 4,624,669 A | 11/1986 | Grendahl et al. |
| 4,640,594 A | 2/1987 | Berger |
| 4,666,249 A | 5/1987 | Bauman et al. |
| 4,666,267 A | 5/1987 | Wichterle |
| 4,676,790 A | 6/1987 | Kern et al. |
| 4,693,715 A | 9/1987 | Abel, Jr. et al. |
| 4,701,288 A | 10/1987 | Cook et al. |
| 4,715,858 A | 12/1987 | Lindstrom et al. |
| 4,772,283 A | 9/1988 | White |
| 4,799,931 A | 1/1989 | Lindstrom et al. |
| 4,806,382 A | 2/1989 | Goldberg et al. |
| 4,810,082 A | 3/1989 | Abel, Jr. |
| 4,834,748 A | 5/1989 | McDonald et al. |
| 4,851,003 A | 7/1989 | Lindstrom et al. |
| 4,886,350 A | 12/1989 | Wichterle et al. |
| 4,890,911 A | 1/1990 | Sulc et al. |
| 4,909,896 A | 3/1990 | Ikushima et al. |
| 4,923,467 A | 5/1990 | Thompson et al. |
| 4,940,751 A | 7/1990 | Frances et al. |
| 4,943,150 A | 7/1990 | Diechert et al. |
| 4,952,045 A | 8/1990 | Stoyan |
| 4,969,912 A | 11/1990 | Kelman et al. |
| 4,973,493 A | 11/1990 | Guire et al. |
| 4,978,481 A | 12/1990 | Janssen et al. |
| 4,979,959 A | 12/1990 | Guire et al. |
| 4,981,841 A | 1/1991 | Gibson |
| 4,983,181 A | 1/1991 | Civerchia et al. |
| 4,994,081 A | 2/1991 | Civerchia et al. |
| 4,997,583 A | 3/1991 | Itzhak |
| 5,008,289 A | 4/1991 | Bernstein |
| 5,019,097 A | 5/1991 | Knight et al. |
| 5,030,230 A | 7/1991 | White et al. |
| 5,073,021 A | 12/1991 | Marron |
| 5,104,213 A | 4/1992 | Wolfson |
| 5,108,428 A | 4/1992 | Capecchi et al. |
| 5,112,350 A | 5/1992 | Civerchia et al. |
| 5,114,627 A | 5/1992 | Civerchia et al. |
| 5,143,660 A | 9/1992 | Hamilton et al. |
| 5,152,786 A | 10/1992 | Hanna |
| 5,156,622 A | 10/1992 | Thompson et al. |
| 5,159,360 A | 10/1992 | Stoy et al. |
| 5,163,596 A | 11/1992 | Ravoo et al. |
| 5,163,934 A | 11/1992 | Munnerlyn et al. |
| 5,166,710 A | 11/1992 | Hofer et al. |
| 5,171,318 A | 12/1992 | Gibson et al. |
| 5,191,365 A | 3/1993 | Stoyan |
| 5,192,316 A | 3/1993 | Ting et al. |
| 5,196,027 A | 3/1993 | Thompson et al. |
| 5,213,720 A | 5/1993 | Civerchia |
| 5,236,236 A | 8/1993 | Girimont |
| 5,244,799 A | 9/1993 | Anderson et al. |
| 5,245,367 A | 9/1993 | Miller et al. |
| 5,246,259 A | 9/1993 | Hellenkamp et al. |
| 5,178,879 A | 11/1993 | Adekunle et al. |
| 5,263,992 A | 11/1993 | Guire et al. |
| 5,292,514 A | 3/1994 | Capecchi et al. |
| 5,293,186 A | 3/1994 | Seden et al. |
| 5,312,320 A | 5/1994 | Esperance, Jr. |
| 5,346,491 A | 9/1994 | Oertli |
| 5,347,326 A | 9/1994 | Volk |

(56) References Cited

U.S. PATENT DOCUMENTS

| | | |
|---|---|---|
| 5,349,395 A | 9/1994 | Stoyan |
| 5,397,848 A | 3/1995 | Yang et al. |
| 5,401,508 A | 3/1995 | Manesis et al. |
| 5,428,412 A | 6/1995 | Stoyan |
| 5,433,714 A | 7/1995 | Bloomberg |
| 5,433,898 A | 7/1995 | Thakrar et al. |
| 5,434,630 A | 7/1995 | Bransome |
| 5,472,436 A | 12/1995 | Fremstad |
| 5,489,300 A | 2/1996 | Capecchi et al. |
| 5,496,084 A | 3/1996 | Miralles Medan |
| 5,517,260 A | 5/1996 | Glady et al. |
| 5,522,888 A | 6/1996 | Civerchia et al. |
| 5,538,301 A | 7/1996 | Yavitz et al. |
| 5,552,452 A | 9/1996 | Khadem et al. |
| 5,570,144 A | 10/1996 | Lofgren-Nisser |
| 5,578,332 A | 11/1996 | Hamilton et al. |
| 5,598,233 A | 1/1997 | Haralambopoulos et al. |
| 5,612,432 A | 3/1997 | Taniguchi et al. |
| 5,628,794 A | 5/1997 | Lindstrom |
| 5,632,733 A | 5/1997 | Shaw et al. |
| 5,632,773 A | 5/1997 | Graham et al. |
| 5,649,922 A | 7/1997 | Yavitz |
| 5,662,706 A | 9/1997 | Legerton et al. |
| 5,671,038 A | 9/1997 | Porat |
| 5,712,721 A | 1/1998 | Large |
| 5,713,957 A | 2/1998 | Steele et al. |
| 5,716,633 A | 2/1998 | Civerchia et al. |
| 5,732,990 A | 3/1998 | Yavitz et al. |
| 5,757,458 A | 5/1998 | Miller et al. |
| 5,760,100 A | 6/1998 | Nicolson et al. |
| 5,760,870 A | 6/1998 | Payor et al. |
| 5,804,263 A | 9/1998 | Goldberg et al. |
| 5,814,329 A | 9/1998 | Shah et al. |
| 5,820,624 A | 10/1998 | Yavitz |
| 5,836,313 A | 11/1998 | Perez et al. |
| 5,854,291 A | 12/1998 | Laughlin et al. |
| 5,869,533 A | 2/1999 | Holt |
| 5,885,597 A | 3/1999 | Botknecht et al. |
| 5,905,561 A | 5/1999 | Lee et al. |
| 5,910,512 A | 6/1999 | Conant |
| 5,923,397 A | 7/1999 | Bonafini, Jr. |
| 5,929,968 A | 7/1999 | Cotie et al. |
| 5,932,205 A | 8/1999 | Wang et al. |
| 5,942,243 A | 8/1999 | Shah et al. |
| 5,953,098 A | 9/1999 | Lieberman et al. |
| 5,957,921 A | 9/1999 | Mirhashemi et al. |
| 5,962,532 A | 10/1999 | Campbell et al. |
| 5,971,541 A | 10/1999 | Danker et al. |
| 5,980,040 A | 11/1999 | Xu et al. |
| 5,986,001 A | 11/1999 | Ingenito et al. |
| 6,010,219 A | 1/2000 | Stoyan |
| 6,030,974 A | 2/2000 | Schwartz et al. |
| 6,036,314 A | 3/2000 | Wolfson et al. |
| 6,036,688 A | 3/2000 | Edwards |
| 6,048,855 A | 4/2000 | De Lacharriere et al. |
| 6,055,990 A | 5/2000 | Thompson et al. |
| 6,075,066 A | 6/2000 | Matsuda et al. |
| 6,090,995 A | 7/2000 | Reich et al. |
| 6,092,898 A | 7/2000 | De Juan, Jr. |
| 6,099,121 A | 8/2000 | Chapman et al. |
| 6,143,315 A | 11/2000 | Wang et al. |
| 6,217,171 B1 | 4/2001 | Auten et al. |
| 6,244,709 B1 | 6/2001 | Vayntraub et al. |
| 6,248,788 B1 | 6/2001 | Robbins et al. |
| 6,325,509 B1 | 12/2001 | Hodur et al. |
| 6,340,229 B1 | 1/2002 | Lieberman et al. |
| 6,361,169 B1 | 3/2002 | Tung |
| 6,364,482 B1 | 4/2002 | Roffman et al. |
| 6,406,145 B1 | 6/2002 | Jubin |
| 6,454,800 B2 | 9/2002 | Dalton et al. |
| 6,474,814 B1 | 11/2002 | Griffin |
| 6,520,637 B2 | 2/2003 | Hodur et al. |
| 6,541,028 B1 | 4/2003 | Kuri-Harcuch et al. |
| 6,544,286 B1 | 4/2003 | Perez et al. |
| 6,551,307 B2 | 4/2003 | Peyman |
| 6,568,808 B2 | 5/2003 | Campin |
| 6,579,918 B1 | 6/2003 | Auten et al. |
| 6,593,370 B2 | 7/2003 | Tamura et al. |
| 6,607,522 B1 | 8/2003 | Hamblin et al. |
| 6,645,715 B1 | 11/2003 | Griffith et al. |
| 6,652,095 B2 | 11/2003 | Tung |
| 6,659,607 B2 | 12/2003 | Miyamura et al. |
| 6,689,165 B2 | 2/2004 | Jacob et al. |
| 6,702,807 B2 | 3/2004 | Peyman et al. |
| 6,726,322 B2 | 4/2004 | Andino et al. |
| 6,726,684 B1 | 4/2004 | Woloszko et al. |
| 6,779,888 B2 | 8/2004 | Marmo |
| 6,843,563 B2 | 1/2005 | Richardson |
| 6,849,671 B2 | 2/2005 | Steffen et al. |
| 6,880,558 B2 | 4/2005 | Perez |
| 6,918,904 B1 | 7/2005 | Peyman et al. |
| 6,951,894 B1 | 10/2005 | Nicolson et al. |
| 6,958,148 B1 | 10/2005 | Green et al. |
| 6,958,158 B2 | 10/2005 | Tenhuisen et al. |
| 7,004,953 B2 | 2/2006 | Pallikaris et al. |
| 7,018,039 B2 | 3/2006 | Legerton et al. |
| 7,025,455 B2 | 4/2006 | Roffman |
| 7,077,839 B2 | 7/2006 | Hamblin et al. |
| 7,080,905 B2 | 7/2006 | Marmo et al. |
| 7,097,301 B2 | 8/2006 | Legerton et al. |
| 7,104,648 B2 | 9/2006 | Dahi et al. |
| 7,150,529 B2 | 12/2006 | Legerton et al. |
| 7,163,292 B2 | 1/2007 | Dahi et al. |
| 7,193,124 B2 | 3/2007 | Coffee |
| 7,216,974 B2 | 5/2007 | Meyers et al. |
| 7,229,685 B2 | 6/2007 | Full et al. |
| 7,249,849 B2 | 7/2007 | Marmo et al. |
| 7,270,412 B2 | 9/2007 | Legerton et al. |
| 7,322,694 B2 | 1/2008 | Dahi et al. |
| 7,329,001 B2 | 2/2008 | Benrashid et al. |
| 7,338,160 B2 | 3/2008 | Lieberman et al. |
| 7,360,890 B2 | 4/2008 | Back |
| 7,377,637 B2 | 5/2008 | Legerton et al. |
| 7,401,922 B2 | 7/2008 | Legerton |
| 7,401,992 B1 | 7/2008 | Lin et al. |
| 7,404,638 B2 | 7/2008 | Miller et al. |
| 7,461,937 B2 | 12/2008 | Steffen et al. |
| 7,491,350 B2 | 2/2009 | Silvestrini |
| 7,530,689 B2 | 5/2009 | Berke |
| 7,537,339 B2 | 5/2009 | Legerton et al. |
| 7,543,936 B2 | 6/2009 | Legerton et al. |
| 7,559,649 B2 | 7/2009 | Cotie et al. |
| 7,585,074 B2 | 9/2009 | Dahi et al. |
| 7,594,725 B2 | 9/2009 | Legerton et al. |
| 7,628,810 B2 | 12/2009 | Christie et al. |
| 7,682,020 B2 | 3/2010 | Berke |
| 7,695,135 B1 | 4/2010 | Rosenthal |
| 7,699,465 B2 | 4/2010 | Dootjes et al. |
| 7,717,555 B2 | 5/2010 | Legerton et al. |
| 7,735,997 B2 | 6/2010 | Muckenhirn |
| 7,748,844 B2 | 7/2010 | Lai |
| 7,762,668 B2 | 7/2010 | Dai et al. |
| 7,828,432 B2 | 11/2010 | Meyers et al. |
| 7,859,769 B2 | 12/2010 | Zalevsky |
| 7,976,577 B2 | 7/2011 | Silvestrini |
| 7,984,988 B2 | 7/2011 | Berke |
| 8,137,344 B2 | 3/2012 | Jia et al. |
| 8,201,941 B2 | 6/2012 | Choo et al. |
| 8,459,793 B2 | 6/2013 | De Juan, Jr. et al. |
| 8,485,662 B2 | 7/2013 | Collins et al. |
| 8,591,025 B1 | 11/2013 | de Juan, Jr. |
| 8,678,584 B2 | 3/2014 | de Juan |
| 8,864,306 B2 | 10/2014 | De Juan et al. |
| 8,882,757 B2 | 11/2014 | Muller et al. |
| 8,926,096 B2 | 1/2015 | De Juan et al. |
| 9,107,773 B2 | 8/2015 | de Juan, Jr. |
| 9,125,735 B2 | 9/2015 | De Juan et al. |
| 9,241,837 B2 | 1/2016 | De Juan et al. |
| 9,341,864 B2 | 5/2016 | De Juan et al. |
| 9,395,558 B2 | 7/2016 | de Juan, Jr. |
| 9,423,632 B2 | 8/2016 | De Juan et al. |
| 9,465,233 B2 | 10/2016 | De Juan et al. |
| 9,498,385 B2 | 11/2016 | De Juan et al. |
| 9,740,025 B2 | 8/2017 | De Juan et al. |

(56) References Cited

U.S. PATENT DOCUMENTS

| | | |
|---|---|---|
| 9,740,026 B2 | 8/2017 | De Juan et al. |
| 9,810,921 B2 * | 11/2017 | De Juan, Jr. .......... A61F 9/0017 |
| 9,851,586 B2 | 12/2017 | De Juan et al. |
| 9,943,401 B2 | 4/2018 | De Juan et al. |
| 10,036,900 B2 | 7/2018 | De Juan et al. |
| 10,039,671 B2 | 8/2018 | De Juan et al. |
| 10,191,303 B2 | 1/2019 | De Juan et al. |
| 2001/0047203 A1 | 11/2001 | Dalton et al. |
| 2002/0095199 A1 | 7/2002 | West, Jr. et al. |
| 2002/0107567 A1 | 8/2002 | Terwee et al. |
| 2002/0151972 A1 | 10/2002 | Hughes et al. |
| 2002/0164484 A1 | 11/2002 | Jiang et al. |
| 2003/0144650 A1 * | 7/2003 | Smith .................... A61F 9/008 606/5 |
| 2003/0187515 A1 | 10/2003 | Hariri et al. |
| 2004/0015163 A1 | 1/2004 | Buysse |
| 2004/0037866 A1 | 2/2004 | Semertzides et al. |
| 2004/0048796 A1 | 3/2004 | Hariri et al. |
| 2004/0053442 A1 | 3/2004 | Akram et al. |
| 2004/0068933 A1 | 4/2004 | Nakamura et al. |
| 2004/0071272 A1 | 4/2004 | Mizuguchi et al. |
| 2004/0088050 A1 | 5/2004 | Norrby et al. |
| 2004/0121885 A1 | 6/2004 | Garcia-Rill et al. |
| 2004/0141150 A1 | 7/2004 | Roffman et al. |
| 2004/0143026 A1 | 7/2004 | Shah et al. |
| 2004/0166255 A1 | 8/2004 | Pierce et al. |
| 2004/0170666 A1 | 9/2004 | Keats et al. |
| 2004/0171878 A1 | 9/2004 | Kok et al. |
| 2004/0184158 A1 | 9/2004 | Shadduck |
| 2004/0194815 A1 | 10/2004 | Deiss et al. |
| 2004/0200320 A1 | 10/2004 | Knopp et al. |
| 2004/0208362 A1 | 10/2004 | Suzuki et al. |
| 2004/0211476 A1 | 10/2004 | Hager et al. |
| 2004/0212779 A1 | 10/2004 | Dahi et al. |
| 2005/0018130 A1 | 1/2005 | Dahi et al. |
| 2005/0028723 A1 | 2/2005 | Ancel et al. |
| 2005/0033420 A1 | 2/2005 | Christie et al. |
| 2005/0107775 A1 | 5/2005 | Huang et al. |
| 2005/0191365 A1 | 9/2005 | Creasey et al. |
| 2005/0213030 A1 | 9/2005 | Meyers et al. |
| 2005/0236236 A1 | 10/2005 | Farooq et al. |
| 2005/0238692 A1 | 10/2005 | Hughes et al. |
| 2005/0245367 A1 | 11/2005 | Horvath et al. |
| 2005/0246259 A1 | 11/2005 | Lavoie et al. |
| 2005/0259221 A1 | 11/2005 | Marmo |
| 2005/0288196 A1 | 12/2005 | Horn |
| 2006/0010219 A1 | 1/2006 | Saito et al. |
| 2006/0013050 A1 | 1/2006 | Fukuzumi et al. |
| 2006/0030974 A1 | 2/2006 | Tsukasaki et al. |
| 2006/0034807 A1 | 2/2006 | Griffith et al. |
| 2006/0036314 A1 | 2/2006 | Perez et al. |
| 2006/0048855 A1 | 3/2006 | Honkura et al. |
| 2006/0075066 A1 | 4/2006 | Farchmin et al. |
| 2006/0077581 A1 | 4/2006 | Schwiegerling |
| 2006/0083773 A1 | 4/2006 | Myung |
| 2006/0099121 A1 | 5/2006 | Doona et al. |
| 2006/0100617 A1 | 5/2006 | Boukhny |
| 2006/0132707 A1 | 6/2006 | Tung |
| 2006/0134170 A1 | 6/2006 | Griffith et al. |
| 2006/0152673 A1 | 7/2006 | Cotie et al. |
| 2006/0197909 A1 | 9/2006 | Legerton |
| 2006/0197910 A1 | 9/2006 | Legerton |
| 2006/0217171 A1 | 9/2006 | Roireau et al. |
| 2006/0235514 A1 | 10/2006 | Silvestrini |
| 2006/0238712 A1 | 10/2006 | Dahi |
| 2006/0241751 A1 * | 10/2006 | Marmo ................ A61F 9/0017 623/5.11 |
| 2006/0244709 A1 | 11/2006 | Lin et al. |
| 2006/0246113 A1 | 11/2006 | Griffith et al. |
| 2006/0248788 A1 | 11/2006 | Harris et al. |
| 2006/0250576 A1 | 11/2006 | Legerton et al. |
| 2006/0256283 A1 | 11/2006 | Legerton |
| 2006/0256284 A1 | 11/2006 | Dahi |
| 2006/0285071 A1 | 12/2006 | Erickson et al. |
| 2006/0285072 A1 | 12/2006 | Dahi et al. |
| 2006/0290882 A1 | 12/2006 | Meyers et al. |
| 2007/0002046 A1 | 1/2007 | Tanacs et al. |
| 2007/0013869 A1 | 1/2007 | Dahi |
| 2007/0014760 A1 | 1/2007 | Peyman |
| 2007/0018039 A1 | 1/2007 | Hillen et al. |
| 2007/0025455 A1 | 2/2007 | Greenwood et al. |
| 2007/0037898 A1 | 2/2007 | Phelan et al. |
| 2007/0046894 A1 | 3/2007 | Muckenhirn |
| 2007/0055222 A1 | 3/2007 | Hohla et al. |
| 2007/0080905 A1 | 4/2007 | Takahara et al. |
| 2007/0097301 A1 | 5/2007 | Yang et al. |
| 2007/0104648 A1 | 5/2007 | Shull et al. |
| 2007/0106394 A1 | 5/2007 | Chen |
| 2007/0129720 A1 | 6/2007 | Demarias et al. |
| 2007/0132948 A1 | 6/2007 | Evans |
| 2007/0135915 A1 | 6/2007 | Klima |
| 2007/0150529 A1 | 6/2007 | McCall et al. |
| 2007/0163292 A1 | 7/2007 | Weng et al. |
| 2007/0182920 A1 | 8/2007 | Back et al. |
| 2007/0193124 A1 | 8/2007 | Thompson et al. |
| 2007/0196454 A1 | 8/2007 | Stockman et al. |
| 2007/0216974 A1 | 9/2007 | Silverbrook et al. |
| 2007/0232755 A1 | 10/2007 | Matsushita et al. |
| 2007/0242216 A1 | 10/2007 | Dootjes et al. |
| 2007/0244559 A1 | 10/2007 | Shiuey |
| 2007/0249849 A1 | 10/2007 | Wiebe et al. |
| 2007/0270412 A1 | 11/2007 | Bell et al. |
| 2007/0273834 A1 | 11/2007 | Legerton |
| 2008/0039832 A1 | 2/2008 | Palanker et al. |
| 2008/0074611 A1 | 3/2008 | Meyers et al. |
| 2008/0100796 A1 | 5/2008 | Pruitt et al. |
| 2008/0201941 A1 | 8/2008 | Montena et al. |
| 2008/0243156 A1 | 10/2008 | John |
| 2008/0287915 A1 | 11/2008 | Rosenthal et al. |
| 2008/0291391 A1 | 11/2008 | Meyers et al. |
| 2009/0033864 A1 | 2/2009 | Shone et al. |
| 2009/0096987 A1 | 4/2009 | Lai et al. |
| 2009/0161826 A1 | 6/2009 | Gertner et al. |
| 2009/0161827 A1 | 6/2009 | Gertner et al. |
| 2009/0182312 A1 | 7/2009 | Gertner et al. |
| 2009/0209954 A1 | 8/2009 | Muller et al. |
| 2009/0216217 A1 | 8/2009 | Odrich et al. |
| 2009/0237612 A1 | 9/2009 | Cotie et al. |
| 2009/0244477 A1 | 10/2009 | Pugh et al. |
| 2009/0303434 A1 | 12/2009 | Tung |
| 2009/0303442 A1 | 12/2009 | Choo et al. |
| 2010/0036488 A1 | 2/2010 | De Juan, Jr. et al. |
| 2010/0060849 A1 | 3/2010 | Hibino |
| 2010/0128224 A1 | 5/2010 | Legerton |
| 2010/0145447 A1 | 6/2010 | Jia et al. |
| 2010/0157250 A1 | 6/2010 | Berke |
| 2010/0185192 A1 | 7/2010 | Muller et al. |
| 2010/0191178 A1 | 7/2010 | Ross et al. |
| 2010/0208196 A1 | 8/2010 | Benrashid et al. |
| 2010/0271589 A1 | 10/2010 | Legerton et al. |
| 2011/0034854 A1 | 2/2011 | Neuberger et al. |
| 2011/0071631 A1 | 3/2011 | Rosenthal |
| 2011/0081000 A1 | 4/2011 | Gertner et al. |
| 2011/0081001 A1 | 4/2011 | Gertner et al. |
| 2011/0190742 A1 | 8/2011 | Anisimov |
| 2011/0208300 A1 | 8/2011 | De Juan, Jr. et al. |
| 2012/0105804 A1 | 5/2012 | Legerton |
| 2012/0113386 A1 | 5/2012 | Back |
| 2012/0169994 A1 | 7/2012 | Matsushita et al. |
| 2012/0310133 A1 | 12/2012 | De Juan, Jr. et al. |
| 2012/0327362 A1 | 12/2012 | Doraiswamy et al. |
| 2013/0025606 A1 | 1/2013 | De Juan, Jr. et al. |
| 2013/0066283 A1 | 3/2013 | De Juan, Jr. et al. |
| 2013/0070200 A1 | 3/2013 | De Juan, Jr. et al. |
| 2013/0077044 A1 | 3/2013 | De Juan, Jr. et al. |
| 2013/0201442 A1 | 8/2013 | Back |
| 2013/0201443 A1 | 8/2013 | Back et al. |
| 2013/0201454 A1 | 8/2013 | Back |
| 2013/0208236 A1 | 8/2013 | McCabe et al. |
| 2013/0208237 A1 | 8/2013 | Hawke et al. |
| 2013/0222761 A1 | 8/2013 | Hansen et al. |
| 2013/0242255 A1 | 9/2013 | Caldarise et al. |
| 2013/0258276 A1 | 10/2013 | Hansen et al. |
| 2013/0278890 A1 | 10/2013 | de Juan et al. |

(56) References Cited

U.S. PATENT DOCUMENTS

| | | |
|---|---|---|
| 2013/0293832 A1 | 11/2013 | de Juan et al. |
| 2014/0028979 A1* | 1/2014 | De Juan, Jr. ......... A61B 3/1005 351/247 |
| 2014/0043588 A1 | 2/2014 | Grant et al. |
| 2014/0069438 A1 | 3/2014 | de Juan et al. |
| 2014/0069439 A1 | 3/2014 | de Juan et al. |
| 2014/0155800 A1 | 6/2014 | de Juan et al. |
| 2014/0251347 A1 | 9/2014 | de Juan et al. |
| 2014/0362338 A1 | 12/2014 | de Juan et al. |
| 2015/0055081 A1 | 2/2015 | de Juan et al. |
| 2015/0077701 A1 | 3/2015 | de Juan et al. |
| 2016/0067109 A1 | 3/2016 | de Juan et al. |
| 2016/0170233 A1 | 6/2016 | De Juan et al. |
| 2016/0223835 A1 | 8/2016 | de Juan et al. |
| 2016/0334640 A1 | 11/2016 | de Juan et al. |
| 2016/0370603 A1 | 12/2016 | De Juan et al. |
| 2017/0023800 A1 | 1/2017 | De Juan, Jr. et al. |
| 2017/0038604 A1 | 2/2017 | De Juan et al. |
| 2017/0131566 A1 | 5/2017 | De Juan, Jr. et al. |
| 2017/0315380 A1 | 11/2017 | De Juan, Jr. et al. |
| 2017/0315381 A1 | 11/2017 | De Juan, Jr. et al. |
| 2017/0340481 A1 | 11/2017 | Daxer |
| 2018/0000639 A1 | 1/2018 | Alster et al. |
| 2018/0193133 A1 | 7/2018 | De Juan et al. |
| 2018/0321511 A1 | 11/2018 | De Juan et al. |
| 2018/0344521 A1 | 12/2018 | Daxer |
| 2019/0353930 A1 | 11/2019 | De Juan, Jr. et al. |

FOREIGN PATENT DOCUMENTS

| | | | |
|---|---|---|---|
| DE | 3143839 | A1 | 5/1983 |
| EP | 0042679 | A2 | 12/1981 |
| EP | 0378512 | A2 | 7/1990 |
| EP | 0434205 | A2 | 6/1991 |
| EP | 0574352 | A1 | 12/1993 |
| EP | 0590772 | A1 | 4/1994 |
| EP | 0378512 | A3 | 2/1995 |
| EP | 0378512 | B1 | 2/1995 |
| EP | 0638416 | A1 | 2/1995 |
| EP | 0683416 | A1 | 11/1995 |
| EP | 0590772 | B1 | 4/1998 |
| EP | 0985157 | B1 | 12/1998 |
| EP | 0985157 | B1 | 10/2004 |
| EP | 1496388 | B1 | 1/2005 |
| EP | 1629317 | A2 | 3/2006 |
| EP | 1664907 | A1 | 6/2006 |
| FR | 2330025 | A1 | 5/1977 |
| GB | 2107895 | A | 5/1983 |
| JP | S52-78453 | B2 | 7/1977 |
| JP | S55101125 | U | 7/1980 |
| JP | S5727456 | Y2 | 6/1982 |
| JP | S5727457 | Y2 | 6/1982 |
| JP | 59-43931 | | 3/1984 |
| JP | 2661909 | B2 | 10/1997 |
| JP | H11151263 | A | 6/1999 |
| JP | H11249048 | A | 9/1999 |
| JP | 2003-107411 | A | 4/2003 |
| JP | 2004504105 | A | 2/2004 |
| JP | 2004510199 | A | 4/2004 |
| JP | 2009-098457 | | 5/2009 |
| WO | 199014083 | A1 | 11/1990 |
| WO | 199207617 | A1 | 5/1992 |
| WO | 199307840 | A1 | 4/1993 |
| WO | 199405225 | A1 | 3/1994 |
| WO | 94/29756 | A1 | 12/1994 |
| WO | 199513764 | A1 | 5/1995 |
| WO | 199515134 | A1 | 6/1995 |
| WO | 199627816 | A1 | 9/1996 |
| WO | 199719381 | A1 | 5/1997 |
| WO | 199803267 | A1 | 1/1998 |
| WO | 199854603 | A1 | 12/1998 |
| WO | 199930560 | A1 | 6/1999 |
| WO | 199943354 | A2 | 9/1999 |
| WO | 199943354 | A3 | 9/1999 |
| WO | 199946631 | A1 | 9/1999 |
| WO | 200009042 | A1 | 2/2000 |
| WO | 200168082 | A1 | 9/2001 |
| WO | 200206883 | A2 | 1/2002 |
| WO | 200210841 | A1 | 2/2002 |
| WO | 2002068008 | A1 | 9/2002 |
| WO | 2003097759 | A1 | 11/2003 |
| WO | 2004068196 | A1 | 8/2004 |
| WO | 2004097502 | A1 | 11/2004 |
| WO | 2004109368 | A2 | 12/2004 |
| WO | 2005079290 | A2 | 9/2005 |
| WO | 2005116729 | A2 | 12/2005 |
| WO | 2006026666 | A2 | 3/2006 |
| WO | 2006026666 | A3 | 3/2006 |
| WO | 2006121591 | A1 | 11/2006 |
| WO | 2006134649 | A1 | 12/2006 |
| WO | 2007002231 | A1 | 1/2007 |
| WO | 2007044513 | A1 | 4/2007 |
| WO | 2007053297 | A2 | 5/2007 |
| WO | 2007053297 | A3 | 5/2007 |
| WO | 2009065061 | A1 | 5/2009 |
| WO | 2009073213 | A1 | 6/2009 |
| WO | 2006113149 | A2 | 10/2009 |
| WO | 2006113149 | A3 | 10/2009 |
| WO | 2009145842 | A2 | 12/2009 |
| WO | WO-2009146151 | A2 | 12/2009 |
| WO | 2010051172 | A1 | 5/2010 |
| WO | 2010144317 | A1 | 12/2010 |
| WO | WO-2011004800 | A1 | 1/2011 |
| WO | 2011050327 | A1 | 4/2011 |
| WO | 2011050365 | A1 | 4/2011 |
| WO | 2012061160 | A1 | 5/2012 |
| WO | 2012149056 | A1 | 11/2012 |
| WO | 2013184239 | A1 | 12/2013 |
| WO | WO-2014043221 | A1 | 3/2014 |
| WO | WO-2014210186 | A2 | 12/2014 |
| WO | WO-2015069927 | A1 | 5/2015 |
| WO | WO-2015073718 | A1 | 5/2015 |
| WO | WO-2015116559 | A1 | 8/2015 |

OTHER PUBLICATIONS

Bausch & Lomb Inc., Boston® Materials & Solutions: Product Guide, 2009.

Bissen-Miyajima, Hiroko et al., "Role of the endothelial pump in flap adhesion after laser in situ keratomileusis," Journal of Cataract & Refractive Surgery, vol. 30, No. 9, pp. 1989-1992, Sep. 2004.

Schimmelpfenning, B. et al., "A technique for controlled sensory denervation of the rabbit cornea," Database Accession No. NLM7129102, Graefe's Archive for Clinical and Experimental Opthalmology, vol. 218, No. 6, pp. 287-293, Jun. 1982 (abstract only).

SynergEyes, Inc., "SynergEyes® A Practitioner Training," Mar. 2011, retrieved from the Internet at <http://www.fitsynergeyes.com/syn_a/synergeyesA_presentation.pdf>.

SynergEyes, Inc., "SynergEyes® A," package insert, P/N 70008 Rev. I, Oct. 2008.

SynergEyes®, Inc., Product Overview of CLEARKONE® and SYNERGEYES® PS, retrieved from the Internet at http://www.synergeyes.com/index.html on May 29, 2012.

Australian Examination Report for Application No. 2012249773, dated Jun. 23, 2016, 4 pages.

Canadian Examination Report for Application No. 2,816,031, dated Aug. 31, 2017, 3 pages.

Canadian Examination Report for Application No. 2,916,885, dated Jan. 24, 2017, 5 pages.

European Patent Application No. 10825787.4, Examination Report dated Aug. 12, 2014.

European Patent Application No. 10825787.4, Search Report dated Jun. 18, 2013.

European Patent Application No. 98936282.7, Examination Report dated Mar. 26, 2004.

Examination Search Report for European Application No. 10825813.8, dated Feb. 20, 2017, 7 pages.

(56) References Cited

OTHER PUBLICATIONS

International Application No. PCT/US2009/002166, International Preliminary Report on Patentability dated Oct. 5, 2010.
International Application No. PCT/US2009/002166, International Search Report and Written Opinion dated Nov. 19, 2009.
International Application No. PCT/US2010/053854, International Preliminary Report on Patentability dated Apr. 24, 2012.
International Application No. PCT/US2010/053854, International Search Report and Written Opinion dated Mar. 1, 2011.
International Application No. PCT/US2010/053975, International Preliminary Report on Patentability dated Apr. 24, 2012.
International Application No. PCT/US2010/053975, International Search Report and Written Opinion dated Feb. 11, 2011.
International Application No. PCT/US2011/057755, International Search Report dated Feb. 7, 2012.
International Application No. PCT/US2012/035050, International Search Report and Written Opinion dated Oct. 3, 2012.
International Application No. PCT/US2013/037219, International Search Report and Written Opinion dated Sep. 30, 2013.
International Application No. PCT/US2013/059244, International Search Report and Written Opinion dated Nov. 26, 2013.
International Application No. PCT/US2014/044136, International Search Report and Written Opinion dated Jan. 16, 2015.
International Application No. PCT/US2014/064391, International Search Report and Written Opinion dated Jan. 26, 2015.
International Application No. PCT/US2014/065543, International Search Report and Written Opinion dated Feb. 25, 2015.
International Application No. PCT/US2014/065543, International Preliminary Report in Patentability dated May 17, 2016.
International Application No. PCT/US2015/013006, International Search Report and Written Opinion dated Apr. 2, 2015.
Japanese Patent Application No. 2011-502997, Office Action dated Jun. 14, 2013.
Japanese Patent Application No. 2011-502997, Office Action dated Mar. 3, 2014.
Non-Final Office Action for U.S. Appl. No. 15/096,442, dated Dec. 28, 2016.
U.S. Appl. No. 12/384,659, Non-Final Office Action dated Jan. 21, 2016.
Non-Final Office Action for U.S. Appl. No. 12/384,659, dated May 30, 2017, 5 pages.
Non-Final Office Action for U.S. Appl. No. 13/456,168, dated Sep. 12, 2013.
Notice of Allowance for U.S. Appl. No. 13/456,168, dated May 30, 2014.
Final Office Action for U.S. Appl. No. 13/503,841, dated Nov. 26, 2014.
Non-Final Office Action for U.S. Appl. No. 13/503,841, dated Jun. 27, 2014.
Non-Final Office Action for U.S. Appl. No. 13/503,841, dated Nov. 16, 2015.
Final Office Action for U.S. Appl. No. 13/503,841, dated Jun. 9, 2016.
Non-Final Office Action for U.S. Appl. No. 13/503,841, dated Mar. 1, 2017, 12 pages.
Final Office Action for U.S. Appl. No. 13/503,842, dated Aug. 13, 2014.
Non-Final Office Action for U.S. Appl. No. 13/503,842, dated Apr. 3, 2014.
Non-Final Office Action for U.S. Appl. No. 13/503,842, dated Nov. 25, 2015.
Notice of Allowance for U.S. Appl. No. 13/503,842, dated Jul. 11, 2016.
Final Office Action for U.S. Appl. No. 13/555,056, dated Sep. 5, 2014.
Non-Final Office Action for U.S. Appl. No. 13/555,056, dated Mar. 28, 2014.
Notice of Allowance for U.S. Appl. No. 13/615,111, dated Apr. 23, 2013.
Notice of Allowance for U.S. Appl. No. 13/715,917, dated Aug. 1, 2013.
Notice of Allowance for U.S. Appl. No. 13/865,780, dated Mar. 28, 2016.
Non-Final Office Action for U.S. Appl. No. 13/885,135, dated Nov. 18, 2014.
Notice of Allowance for U.S. Appl. No. 13/885,135, dated Mar. 16, 2016.
Non-Final Office Action for U.S. Appl. No. 15/184,922, dated Jun. 2, 2017, 22 pages.
Non-Final Office Action for U.S. Appl. No. 13/894,176, dated Aug. 5, 2013.
Notice of Allowance for U.S. Appl. No. 13/894,176, dated Feb. 26, 2014.
Notice of Allowance for U.S. Appl. No. 13/928,077, dated Jan. 15, 2014.
Non-Final Office Action for U.S. Appl. No. 14/061,311, dated Apr. 21, 2016.
Final Office Action for U.S. Appl. No. 14/061,311, dated Mar. 9, 2017.
Non-Final Office Action for U.S. Appl. No. 14/286,605, dated Dec. 18, 2014.
Final Office Action for U.S. Appl. No. 14/468,075, dated Apr. 1, 2016.
Non-Final Office Action for U.S. Appl. No. 14/532,707, dated Feb. 25, 2016.
Notice of Allowance for U.S. Appl. No. 14/532,707, dated Jun. 8, 2016.
Non-Final Office Action for U.S. Appl. No. 14/532,732, dated Apr. 11, 2016.
Final Office Action for U.S. Appl. No. 14/532,732, dated Oct. 3, 2016.
Notice of Allowance for U.S. Appl. No. 14/539,698, dated Jan. 21, 2016.
Non-Final Office Action for U.S. Appl. No. 14/468,075, dated Nov. 7, 2016.
Non-Final Office Action for U.S. Appl. No. 14/793,965, dated Dec. 31, 2015.
Non-Final Office Action for U.S. Appl. No. 14/966,918, dated Nov. 18, 2016.
Non-Final Office Action for U.S. Appl. No. 14/173,516, dated Feb. 8, 2017.
Non-Final Office Action for U.S. Appl. No. 15/253,183, dated Nov. 3, 2017.
Extended European Search Report for EP Application No. 17183160.5, dated Sep. 12, 2017, 6 pages.
JP2011502997 English translation of Japanese Office Action dated Jun. 14, 2013.
Muller et al. Architecture of human corneal nerves. Invest Ophthalmol Vis Sci. 38:985-994 (1997).
PCT/US2013/033567 International Search Report dated Mar. 4, 2014.
Sorbara et al. Metrics of the normal cornea: anterior segment imaging with the Visante OCT. Clin Exp Optom 93(3):150-156 (2010).
U.S. Appl. No. 12/384,659 Office Action dated Nov. 4, 2016.
U.S. Appl. No. 12/897,131 Office Action dated Jan. 24, 2013.
U.S. Appl. No. 12/897,131 Office Action dated Jul. 5, 2012.
U.S. Appl. No. 12/897,131 Office Action dated Sep. 9, 2014.
U.S. Appl. No. 13/865,780 Office Action dated Nov. 6, 2015.
U.S. Appl. No. 13/885,135 Office Action dated Jun. 11, 2015.
U.S. Appl. No. 13/928,077 Office Action dated Oct. 22, 2013.
U.S. Appl. No. 14/173,516 Office Action dated Apr. 3, 2019.
U.S. Appl. No. 14/468,075 Office Action dated Nov. 5, 2015.
U.S. Appl. No. 14/539,698 Office Action dated Oct. 9, 2015.
U.S. Appl. No. 15/184,922 Office Action dated Mar. 30, 2018.
U.S. Appl. No. 15/209,511 Office Action dated Apr. 30, 2018.
U.S. Appl. No. 15/209,511 Office Action dated Jan. 3, 2019.
U.S. Appl. No. 15/221,942 Office Action dated Feb. 1, 2018.
U.S. Appl. No. 15/289,793 Office Action dated Jan. 22, 2019.
U.S. Appl. No. 15/652,855 Office Action dated Aug. 9, 2018.
U.S. Appl. No. 15/652,855 Office Action dated Mar. 1, 2019.
U.S. Appl. No. 15/654,344 Office Action dated Mar. 22, 2019.

(56) References Cited

OTHER PUBLICATIONS

U.S. Appl. No. 15/695,889 Office Action dated Sep. 18, 2018.
U.S. Appl. No. 15/807,985 Office Action dated Feb. 5, 2019.
U.S. Appl. No. 15/917,071 Office Action dated Sep. 7, 2018.
Co-pending U.S. Appl. No. 16/559,479, filed Sep. 3, 2019.
U.S. Appl. No. 15/209,511 Office Action dated Aug. 5, 2019.
U.S. Appl. No. 15/684,010 Office Action dated Aug. 12, 2019.

* cited by examiner

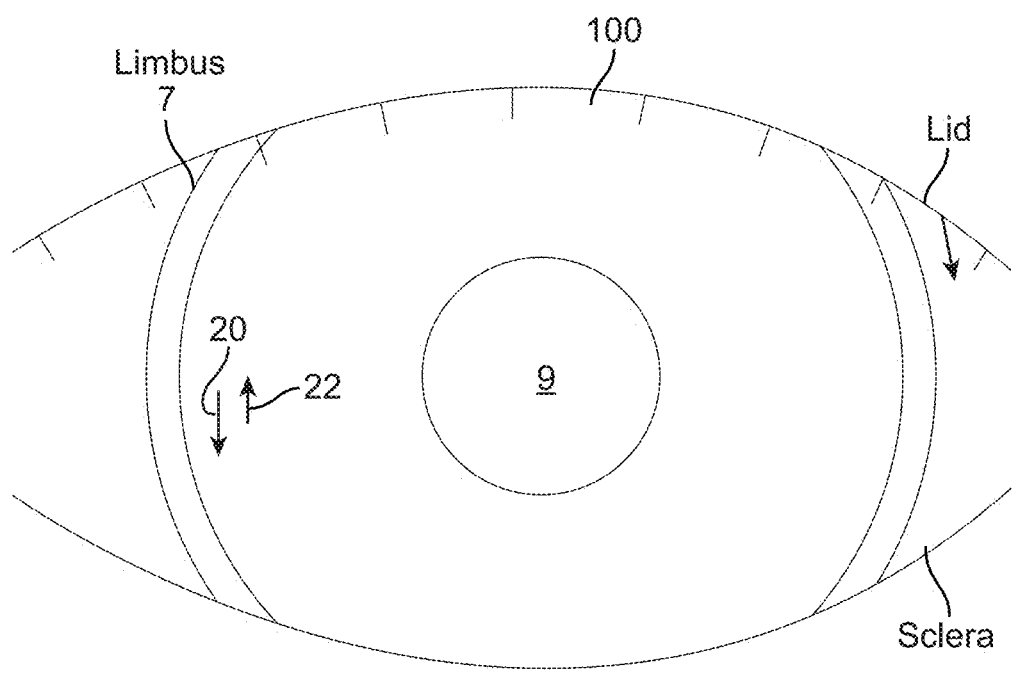
FIG. 1A1

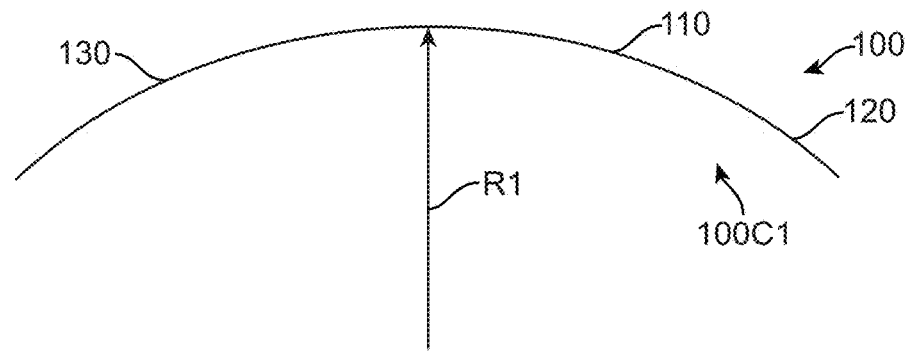
FIG. 1B1
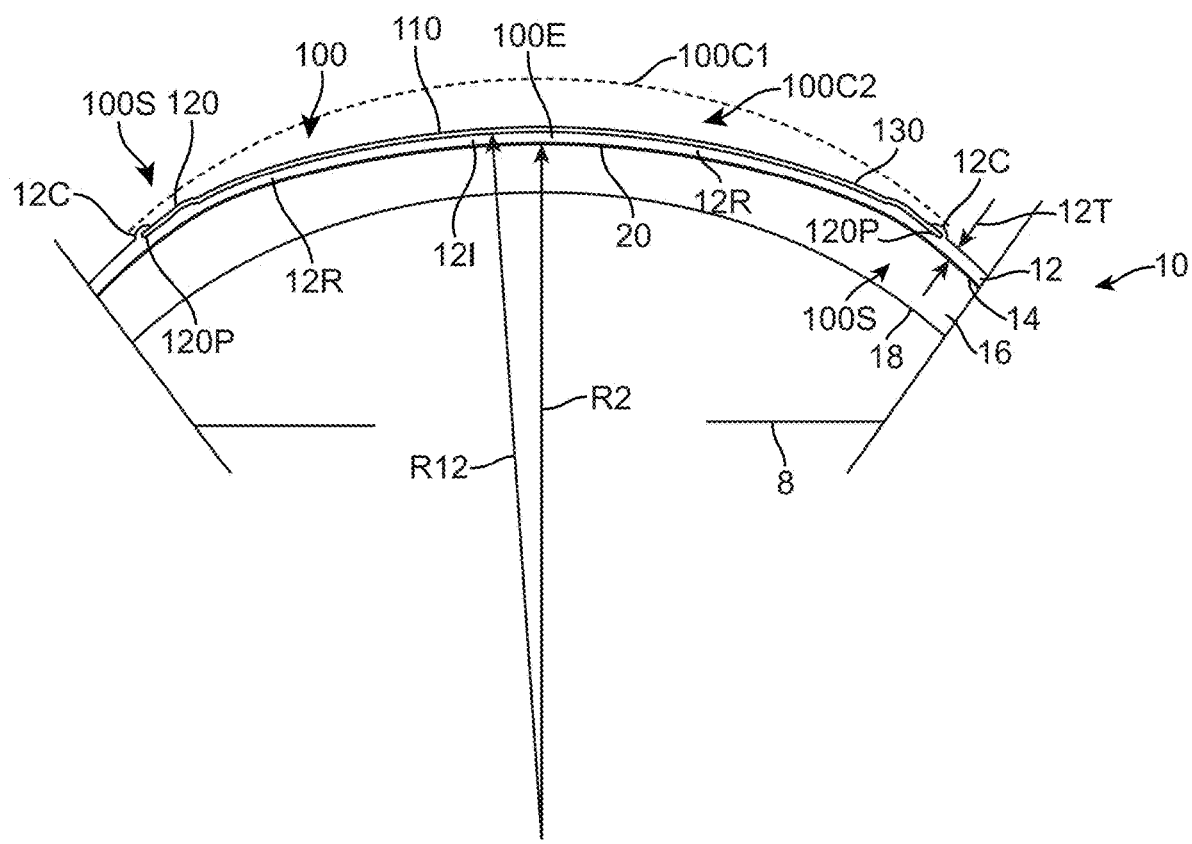
FIG. 1B2

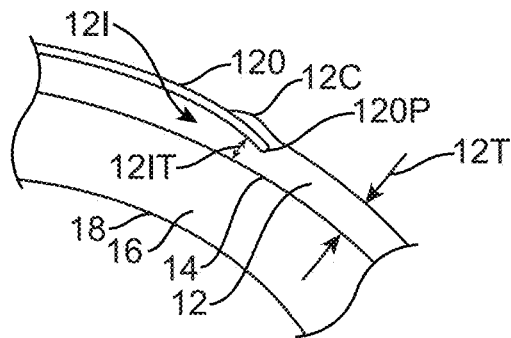
FIG. 1B2A
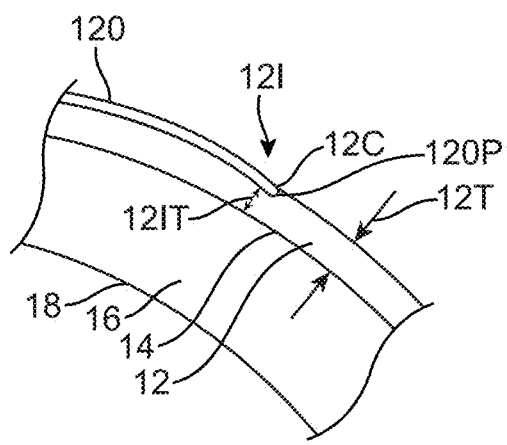
FIG. 1B2B

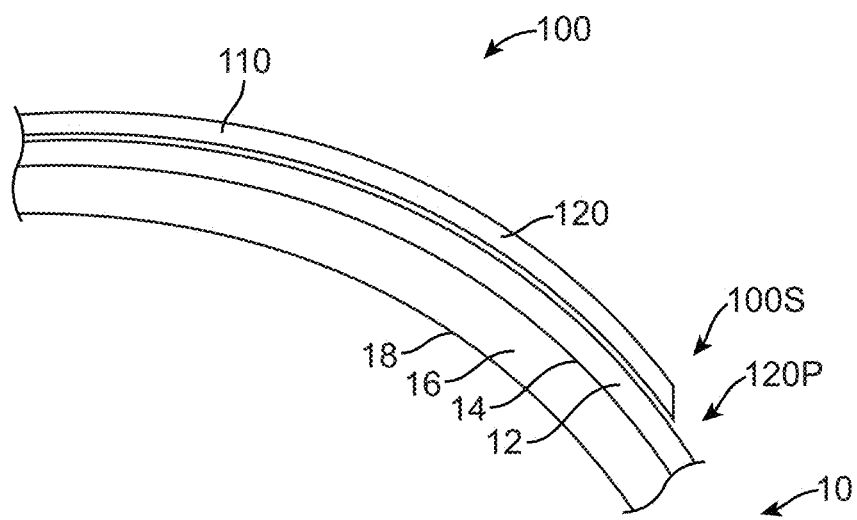
FIG. 1B2C

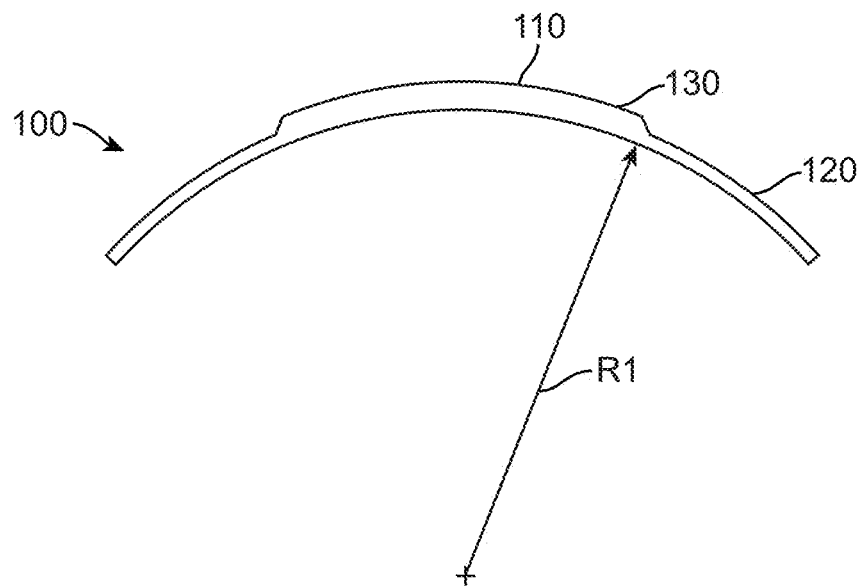
FIG. 1C
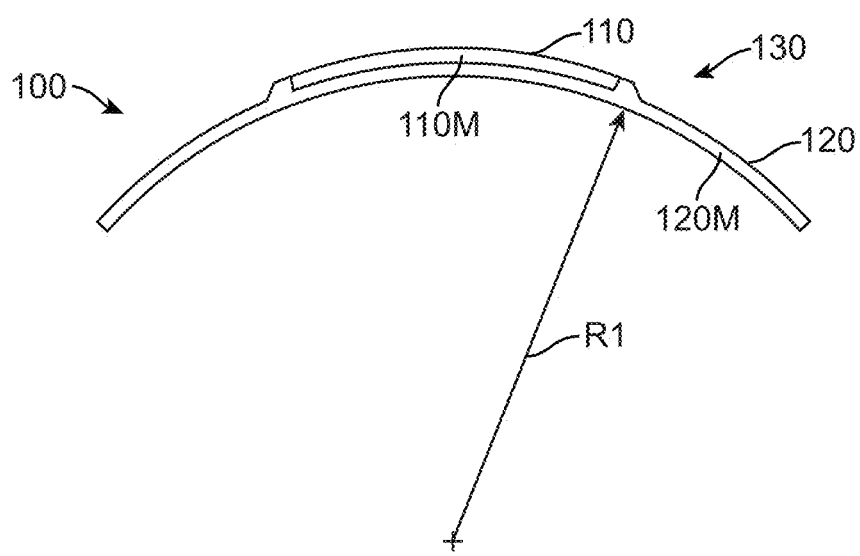
FIG. 1C1

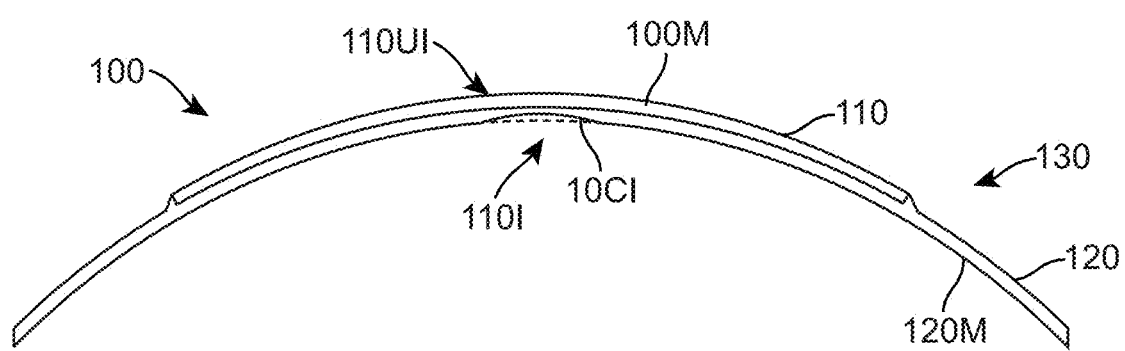
FIG. 1C1A

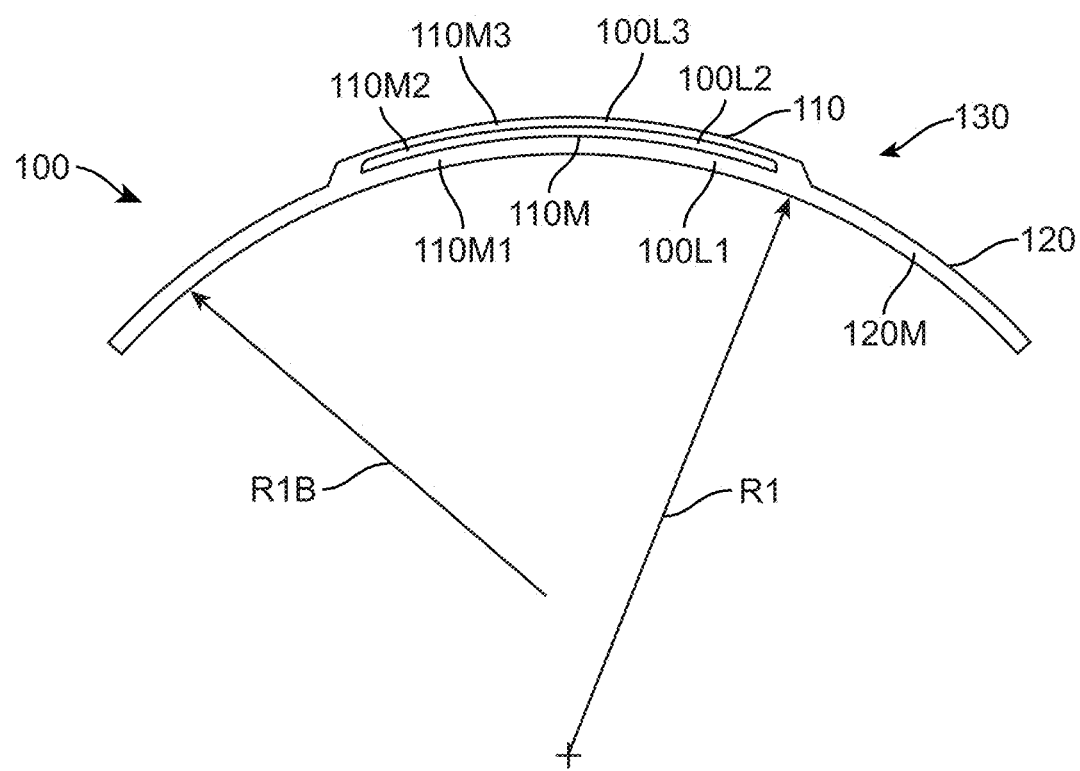
FIG. 1C2

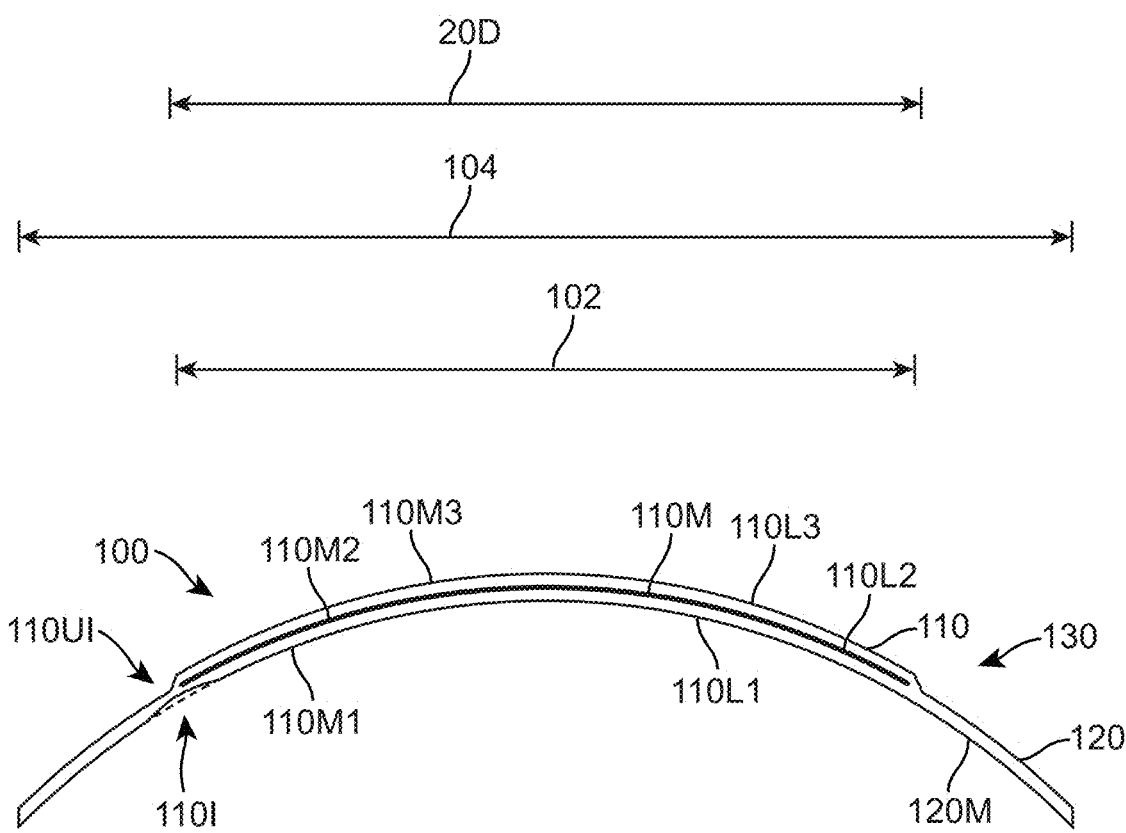
FIG. 1C2A

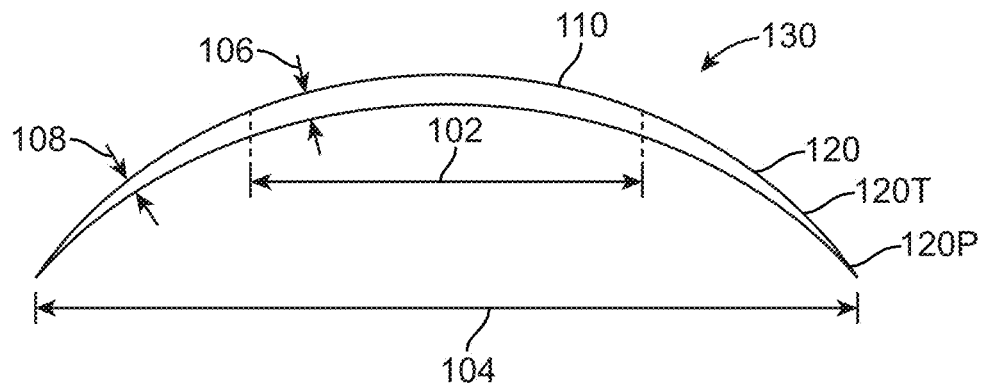
FIG. 1G
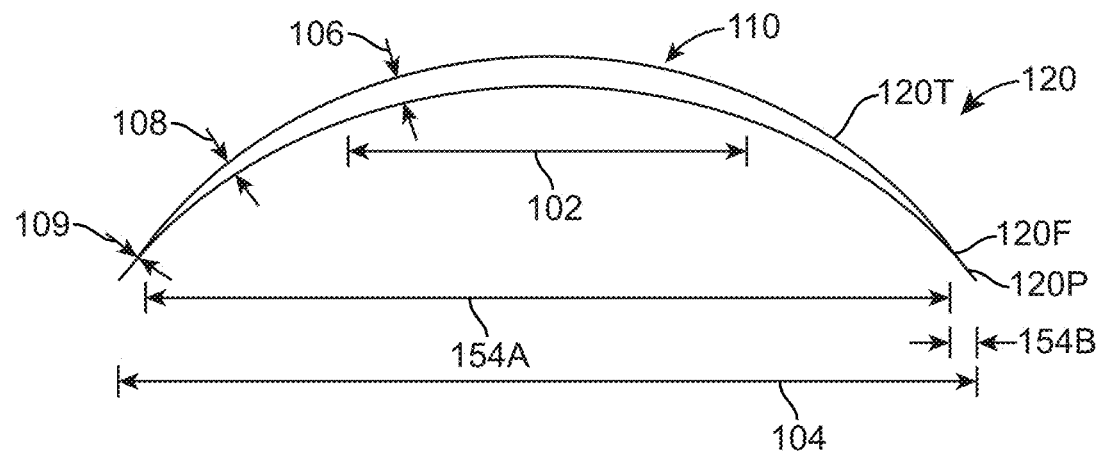
FIG. 1G1

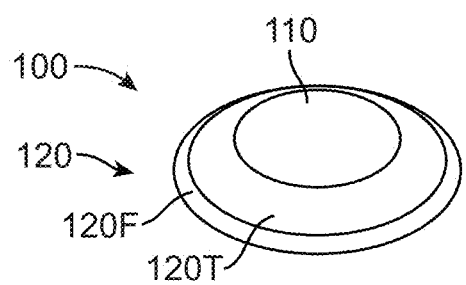
FIG. 1G1A
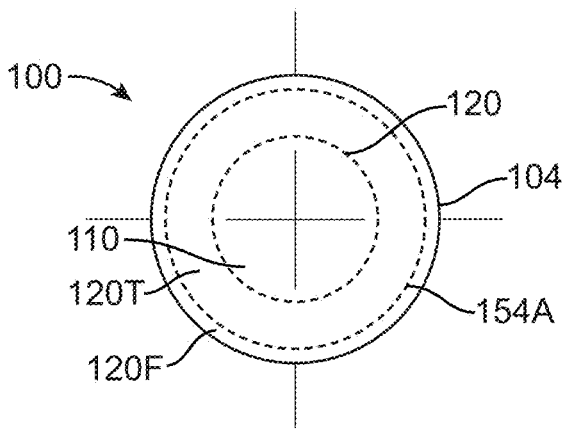
FIG. 1G1B
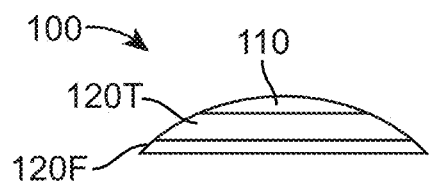
FIG. 1G1C
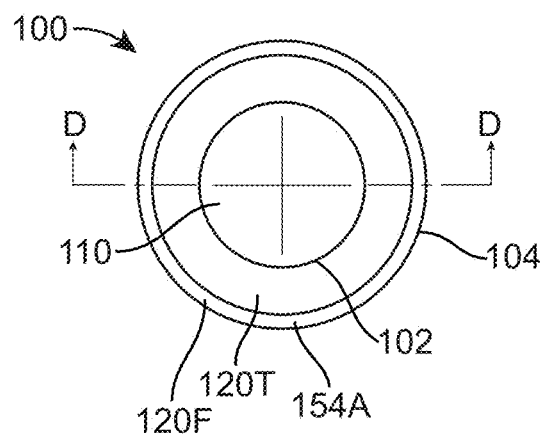
FIG. 1G1D

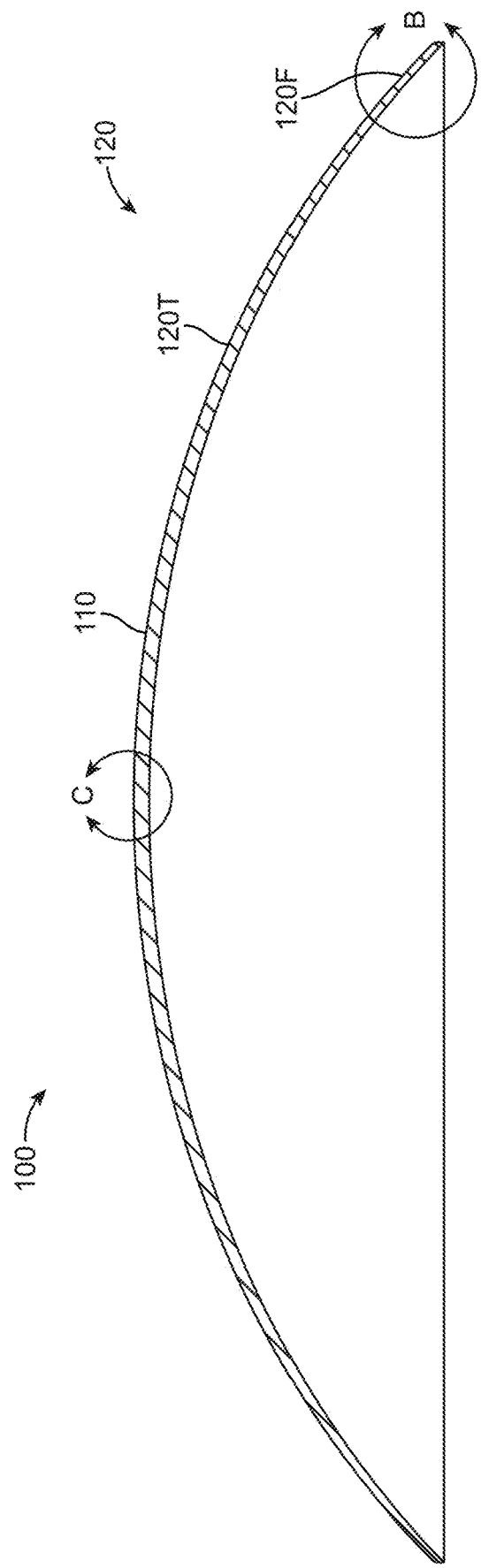
FIG. 1G1E

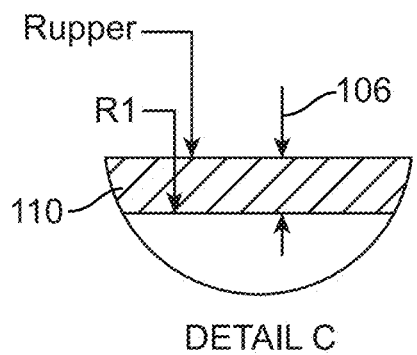
FIG. 1G1F
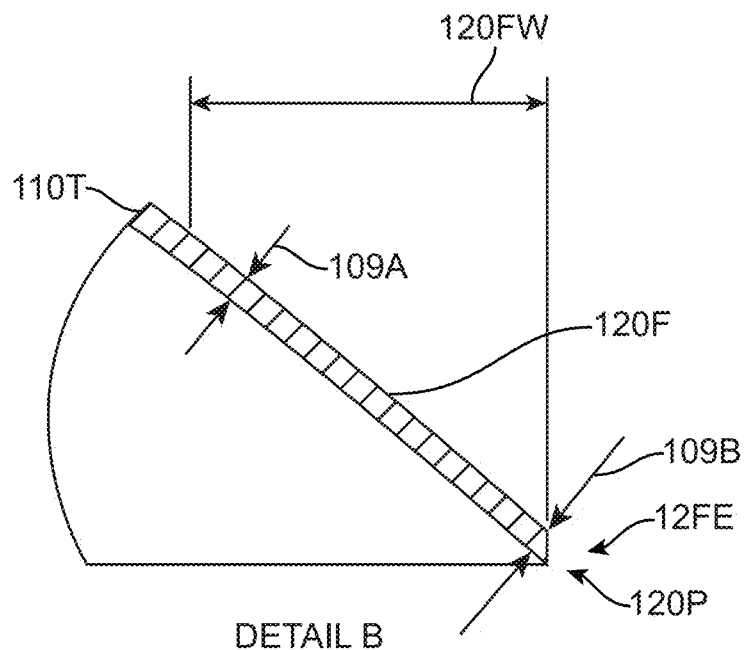
FIG. 1G1G

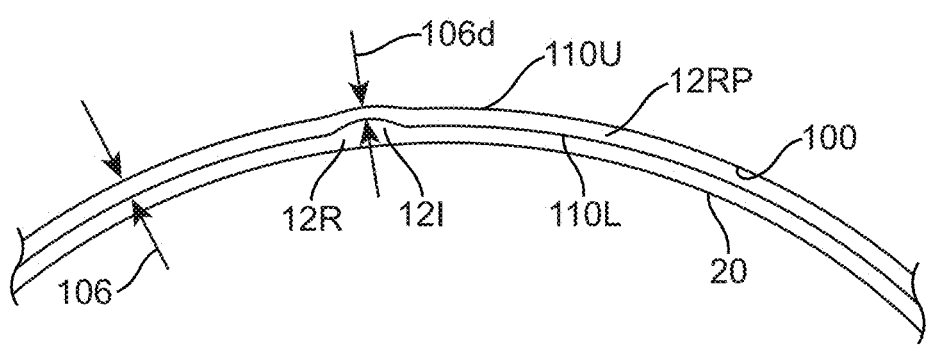
FIG. 1H1

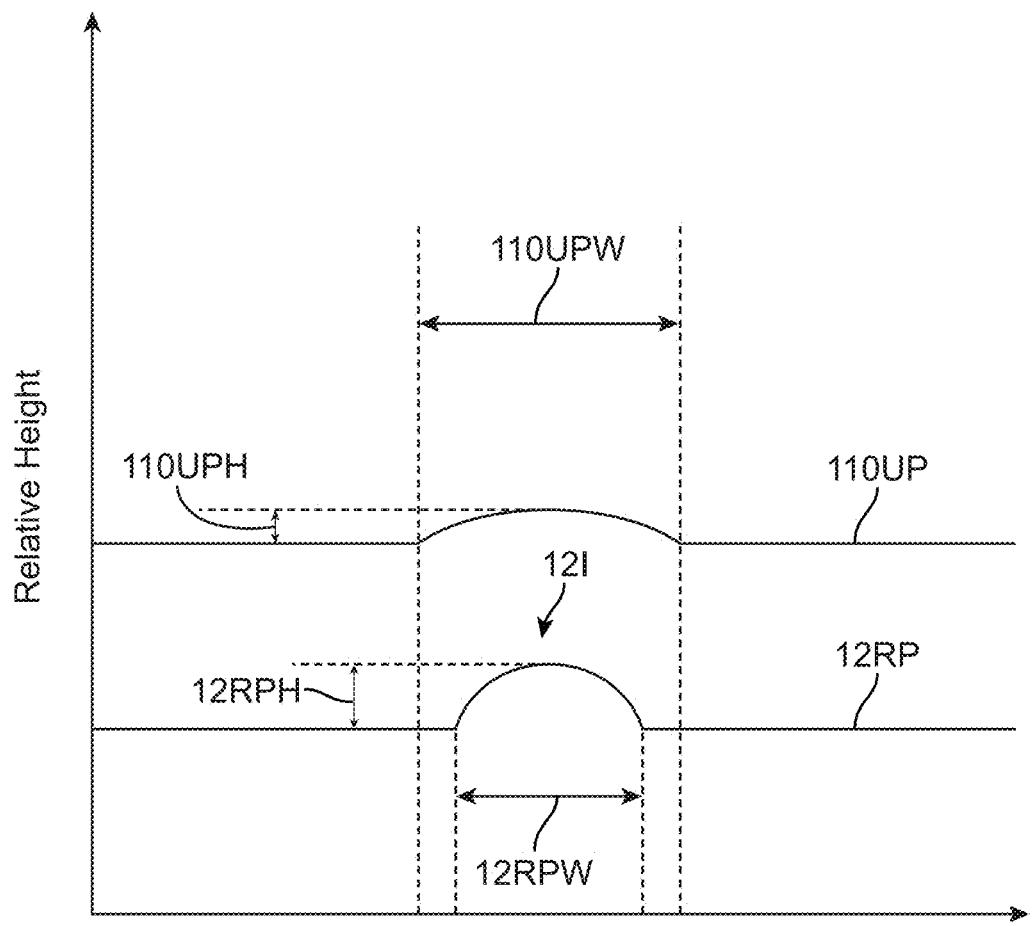
FIG. 1H2

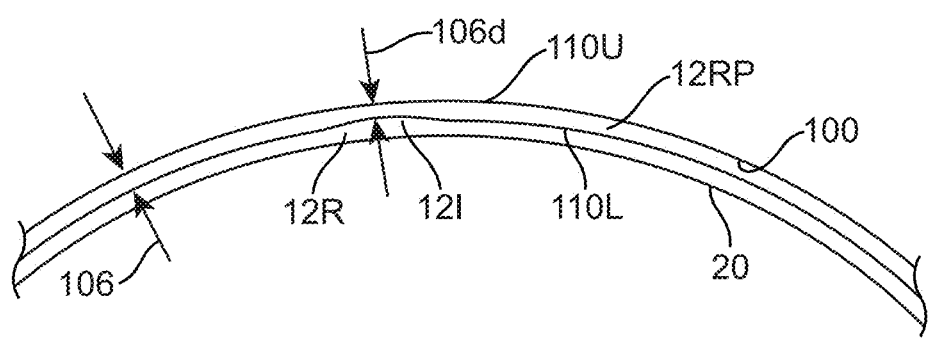
FIG. 1I1

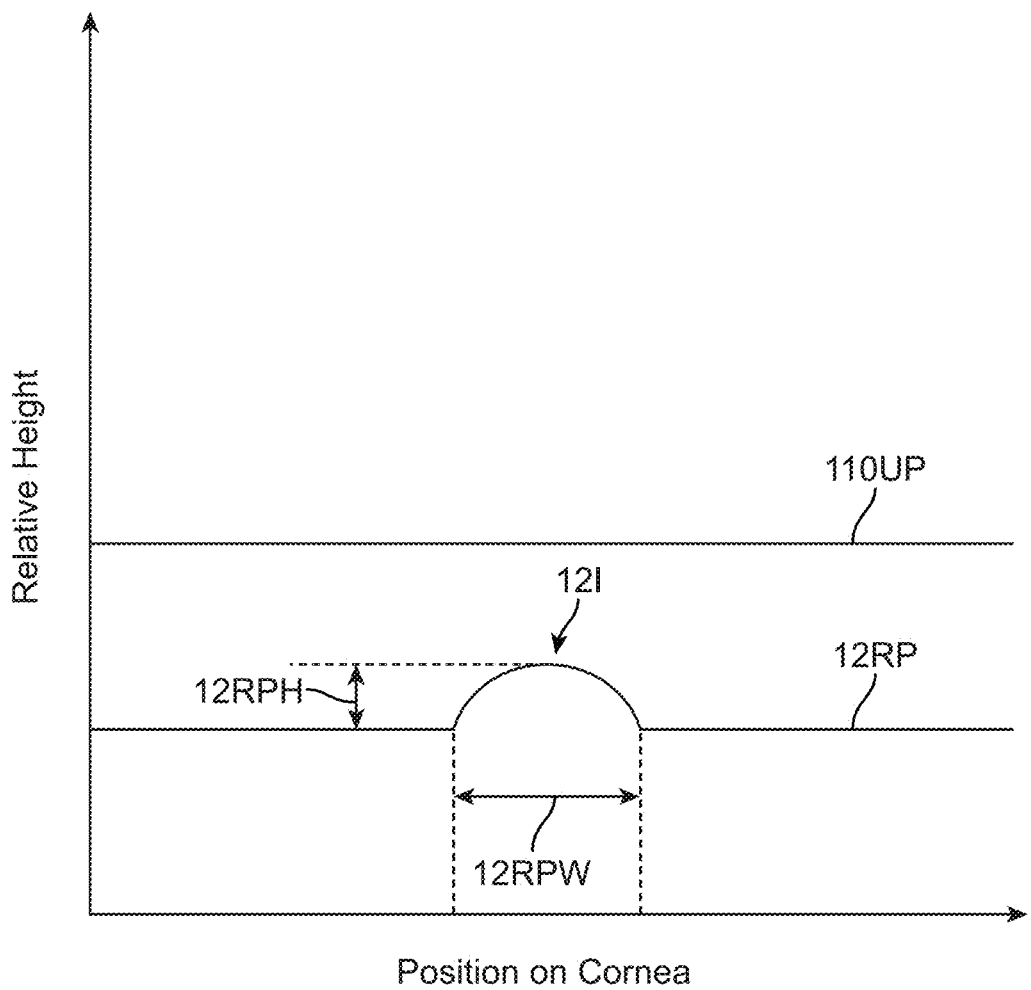
FIG. 1I2
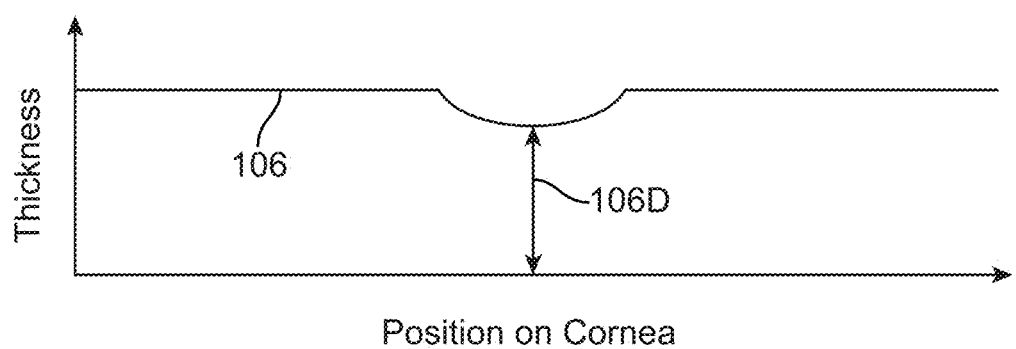
FIG. 1I3

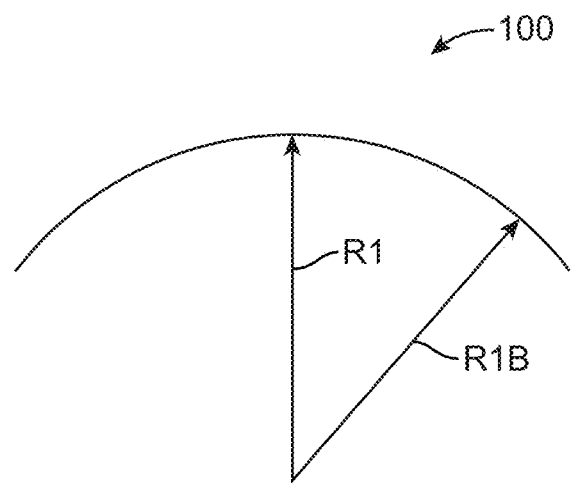
FIG. 1J1
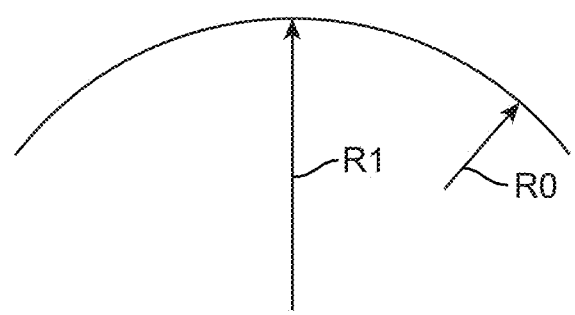
FIG. 1J2

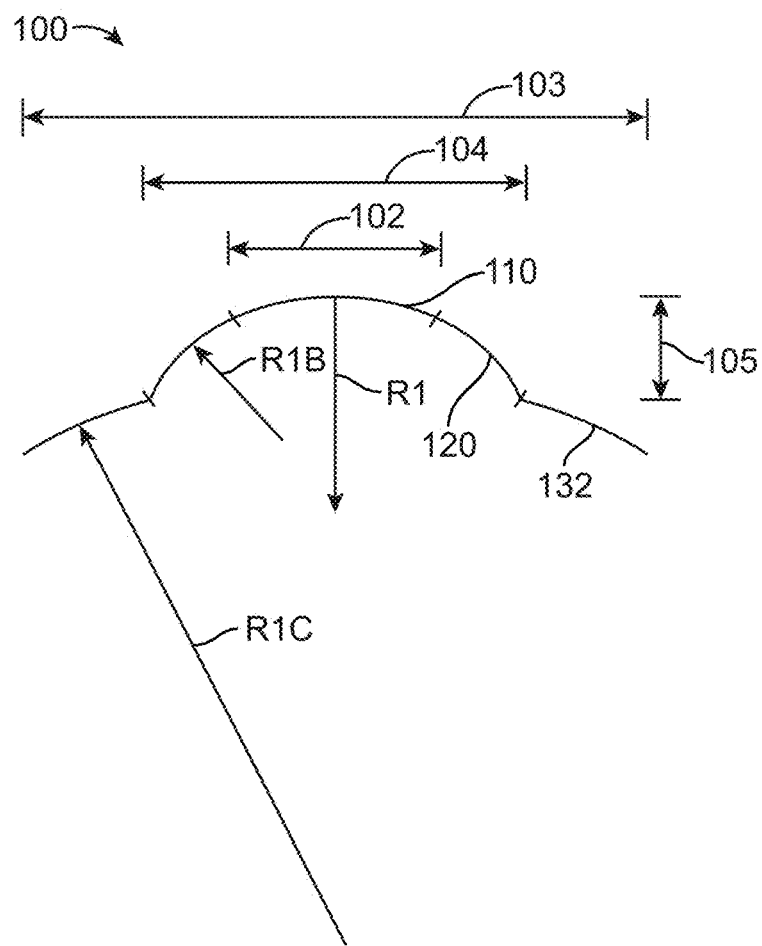
FIG. 1J3
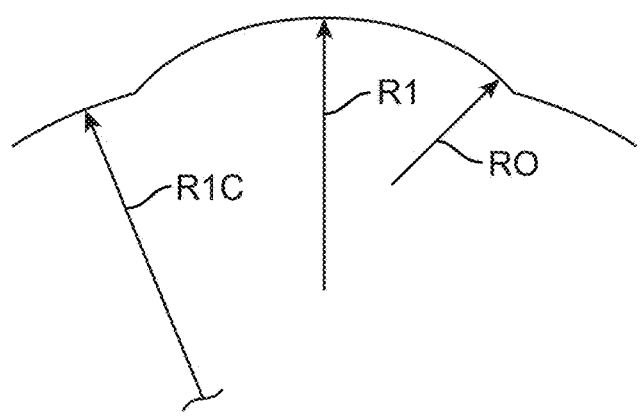
FIG. 1J4

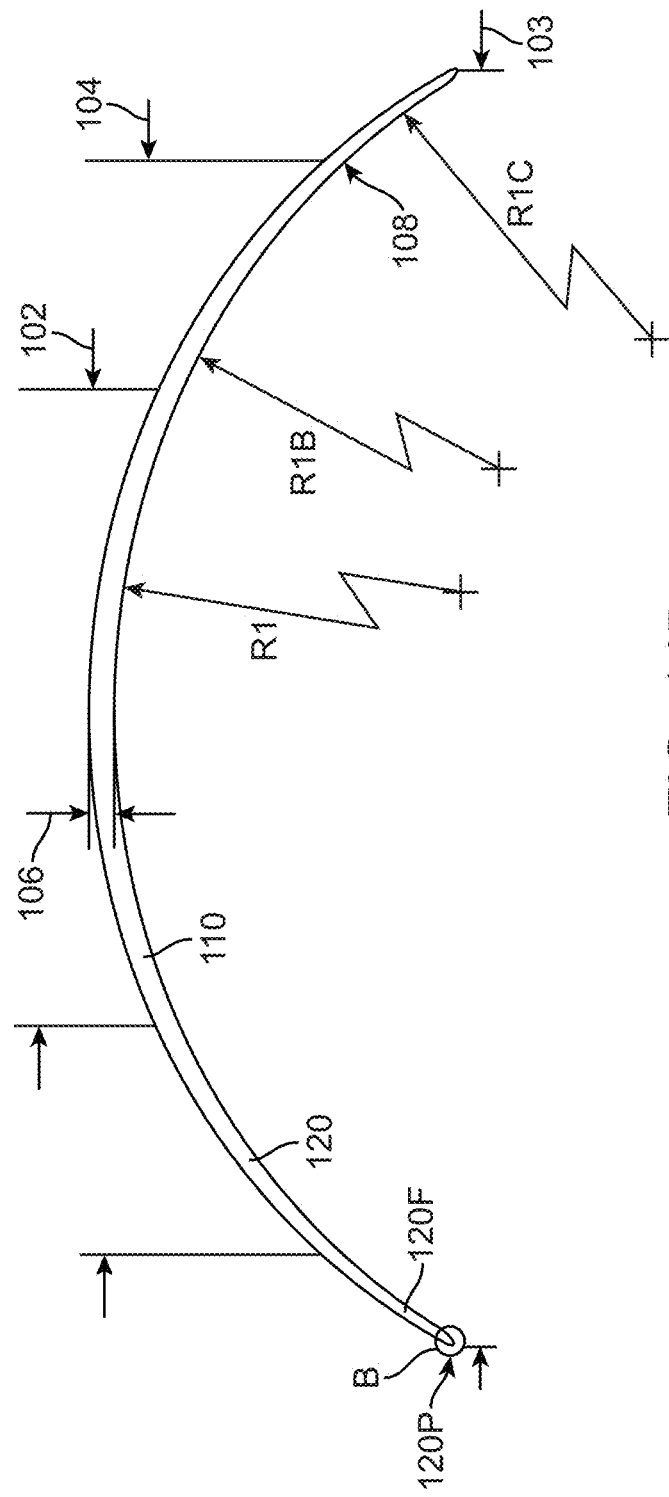
FIG. 1J5

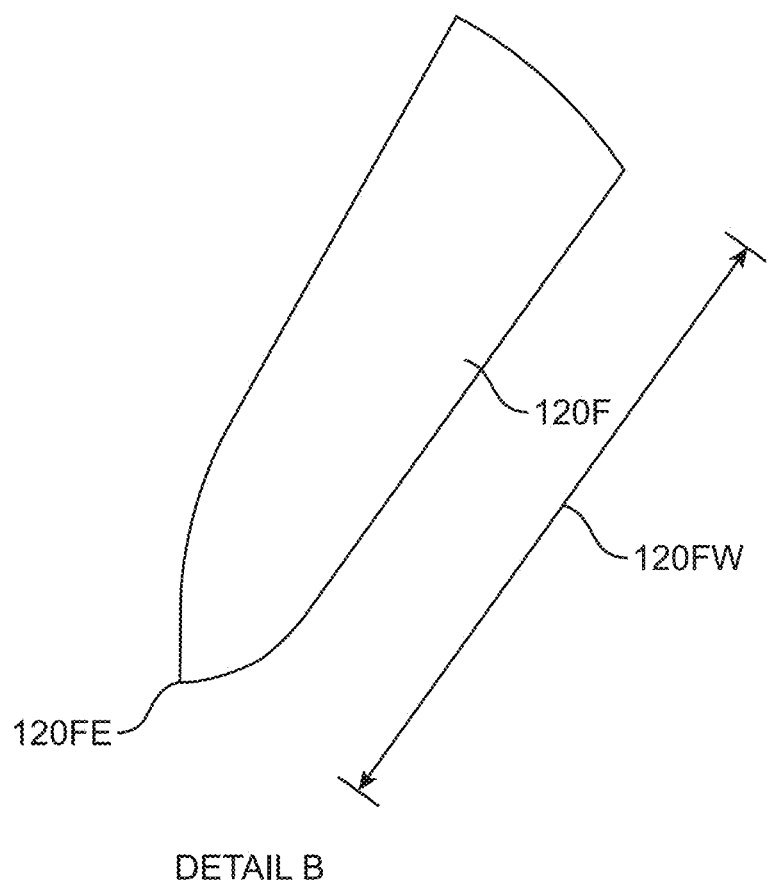
FIG. 1J6

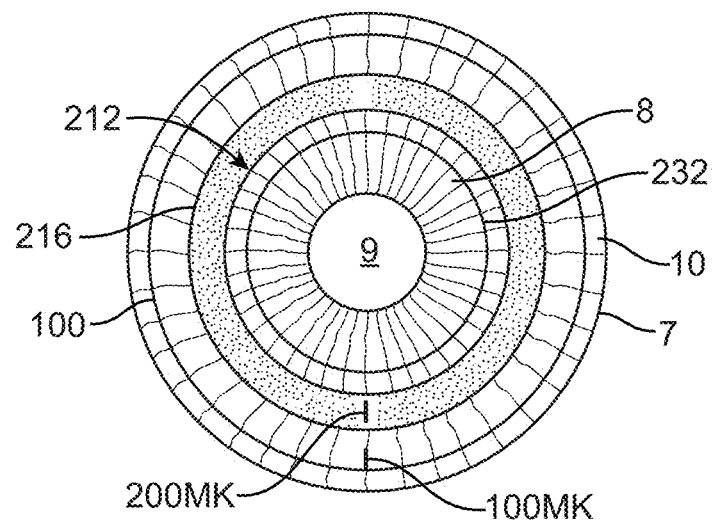
FIG. 2A1
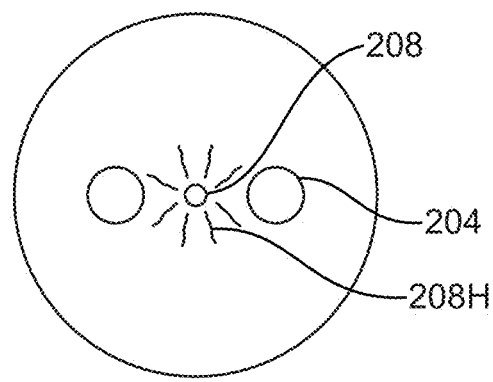
FIG. 2A2

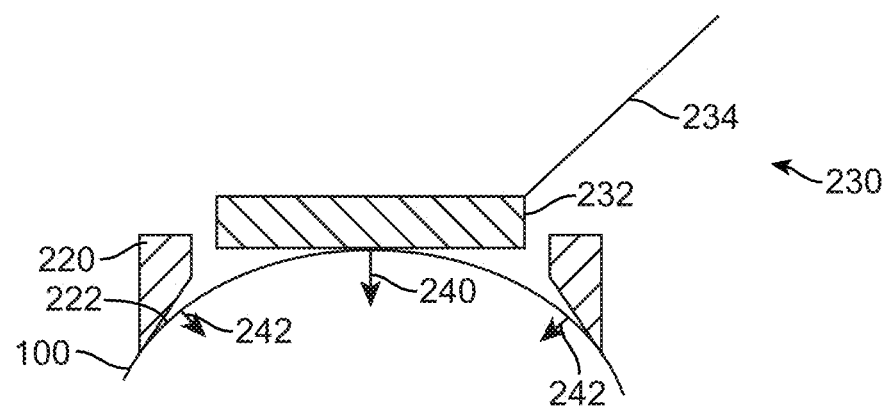
FIG. 2C
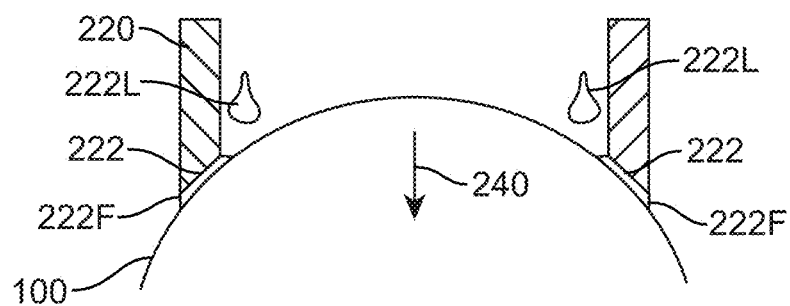
FIG. 2C1

FIG. 2D1

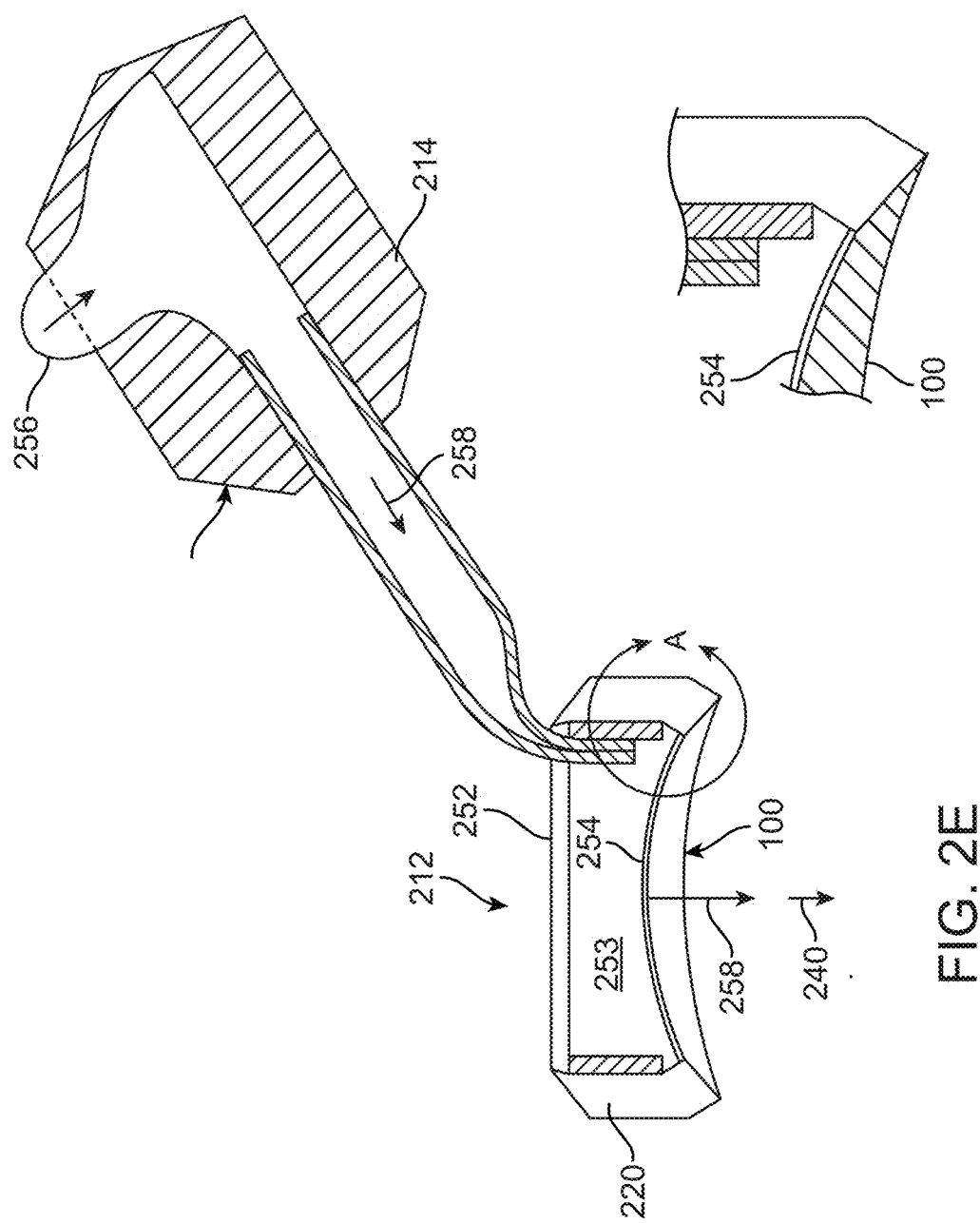

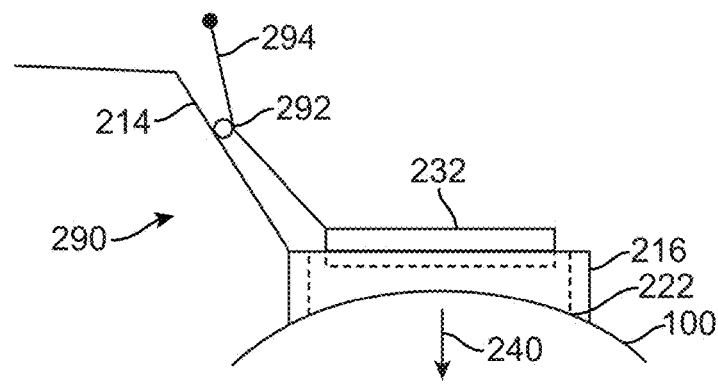
FIG. 2J
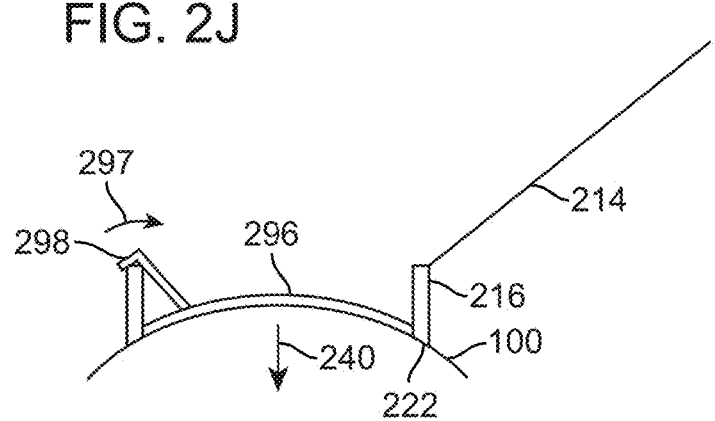
FIG. 2K1
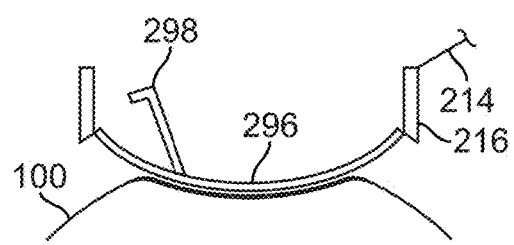
FIG. 2K3
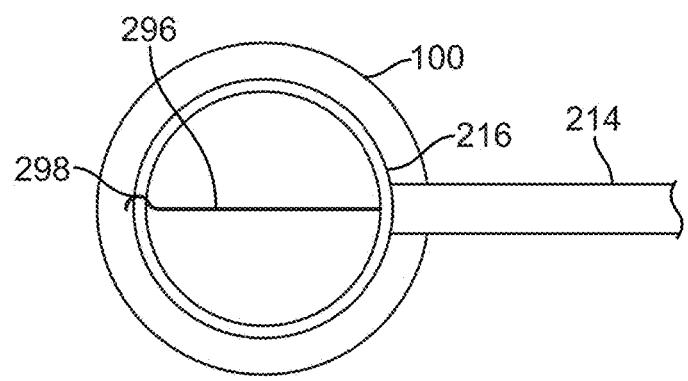
FIG. 2K2

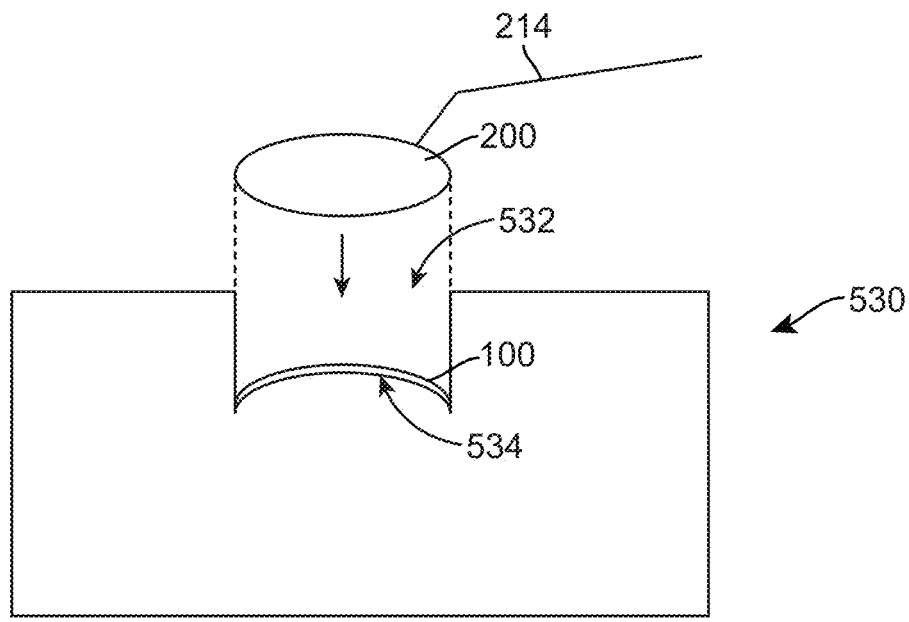
FIG. 5B1
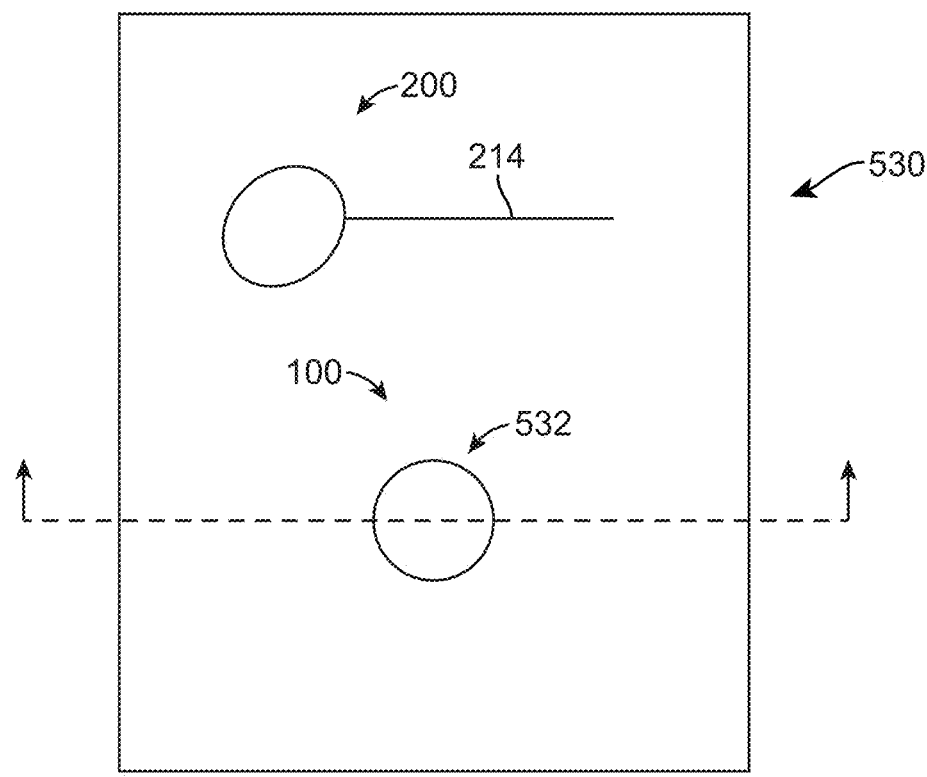
FIG. 5B2

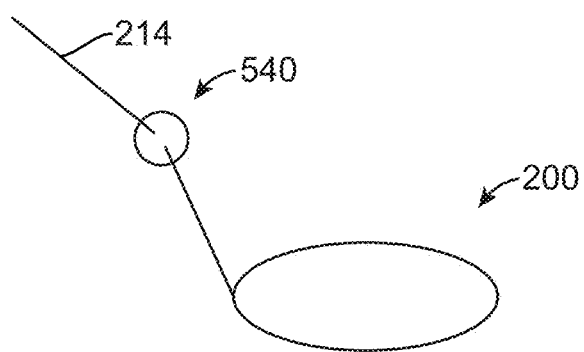
FIG. 5B3

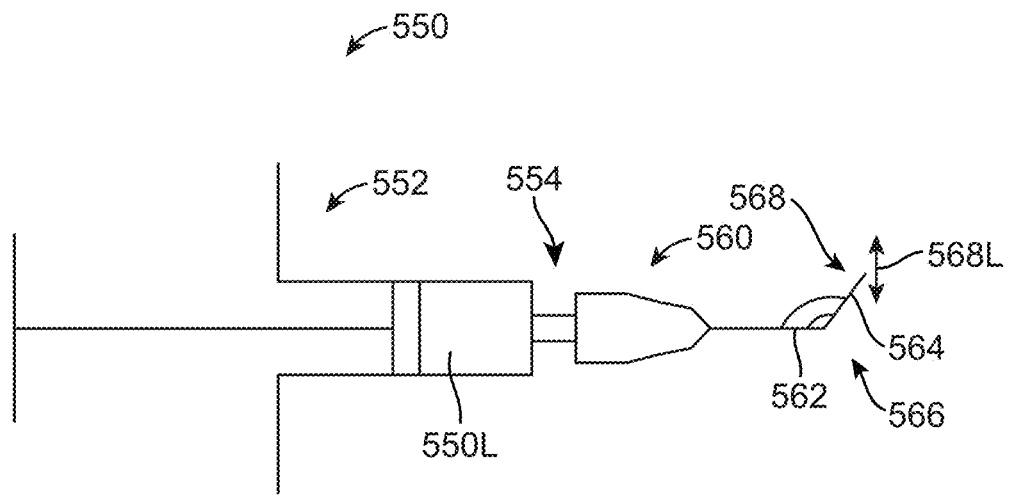
FIG. 5C1
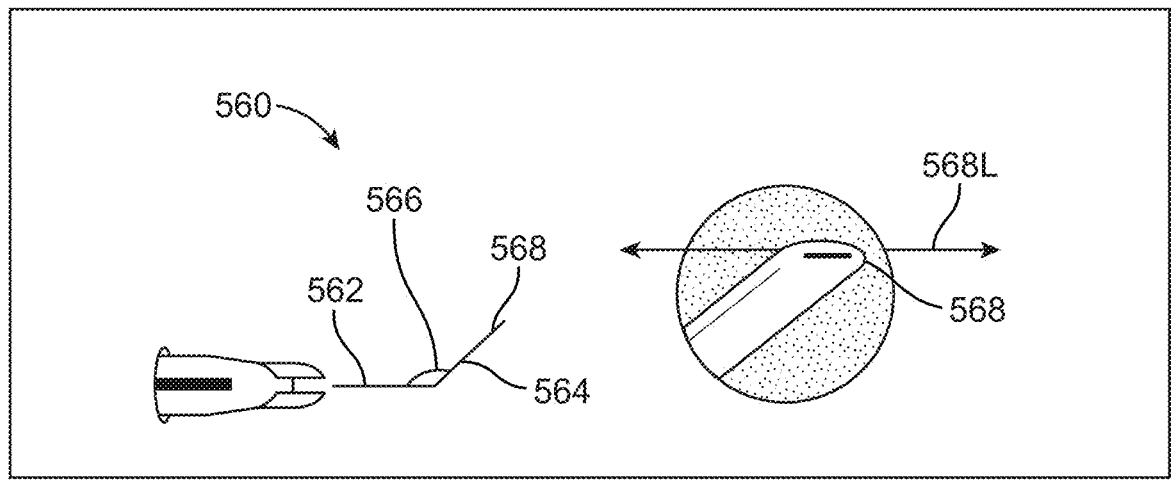
FIG. 5C2

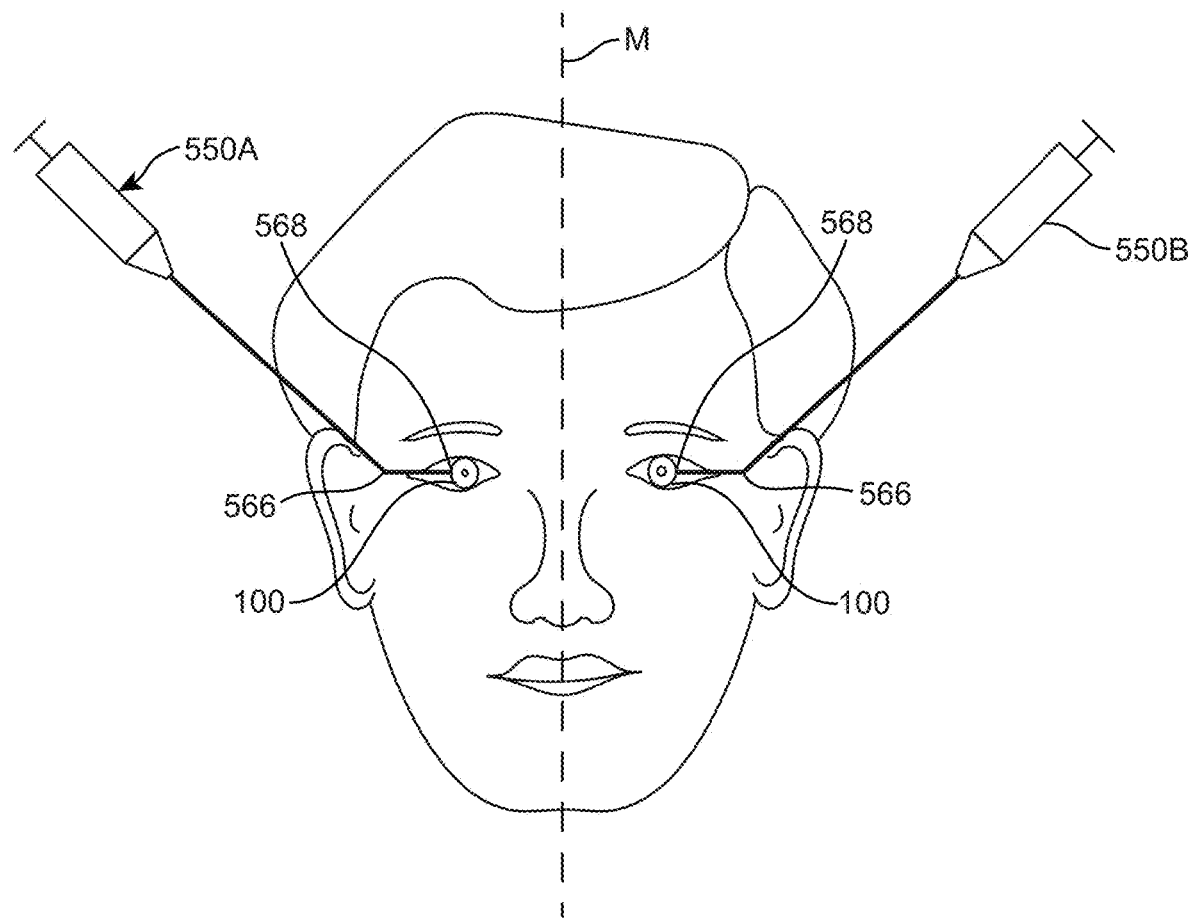
FIG. 5C3
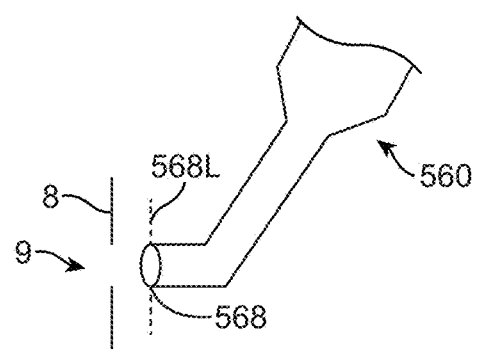
FIG. 5C4

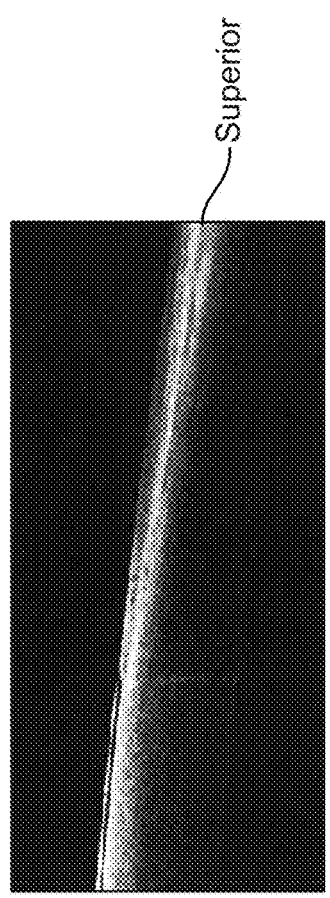
FIG. 11A1A
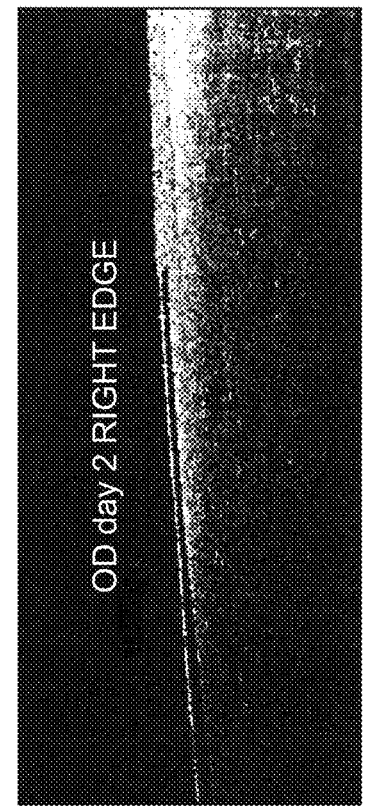
FIG. 11A1C
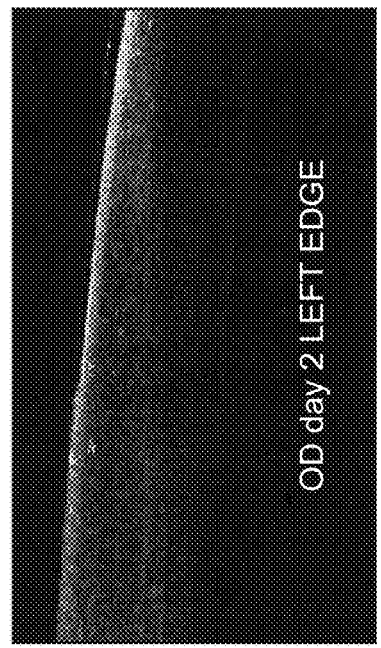
FIG. 11A1B
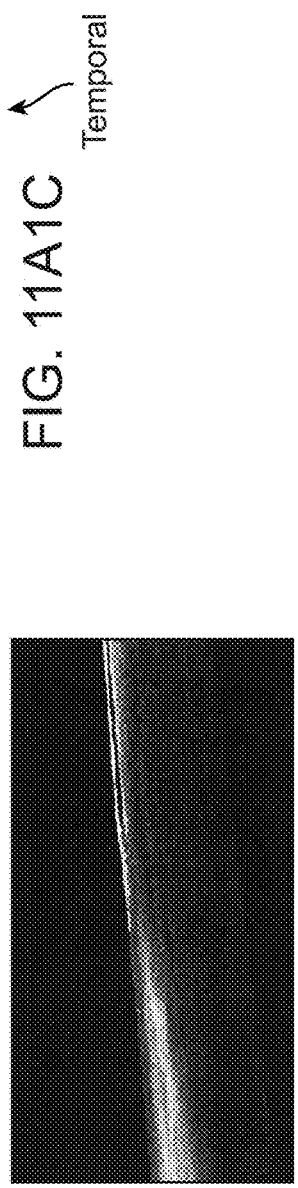
FIG. 11A1D

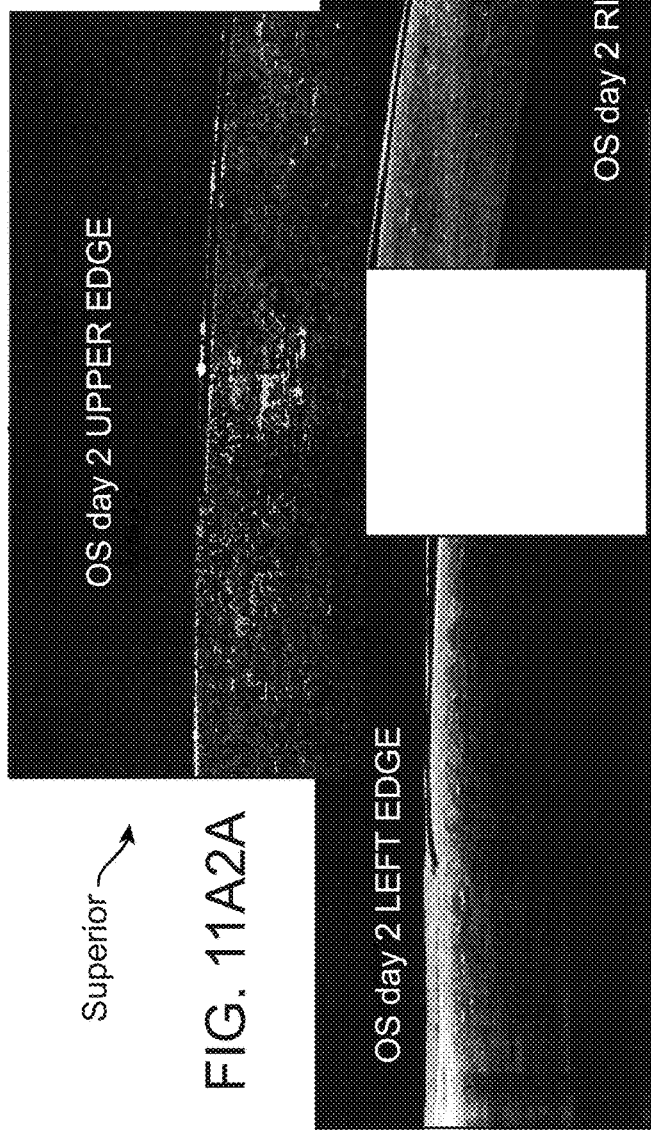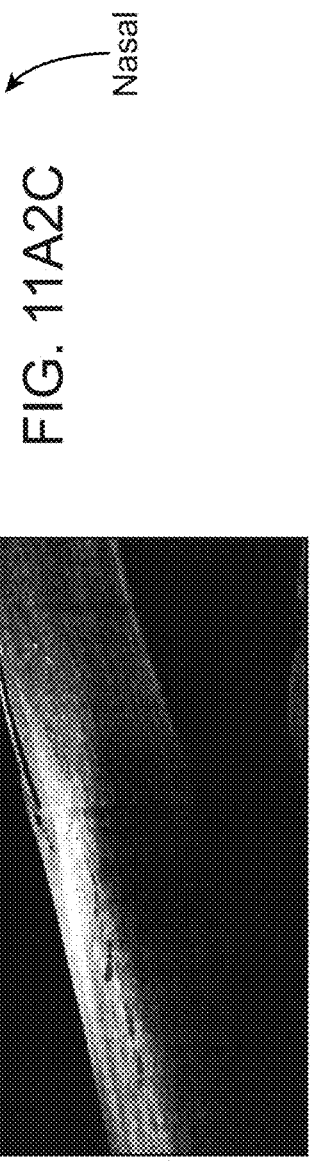

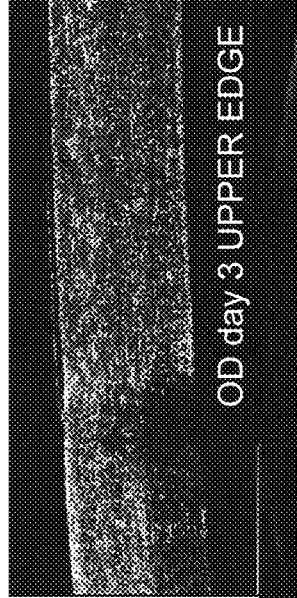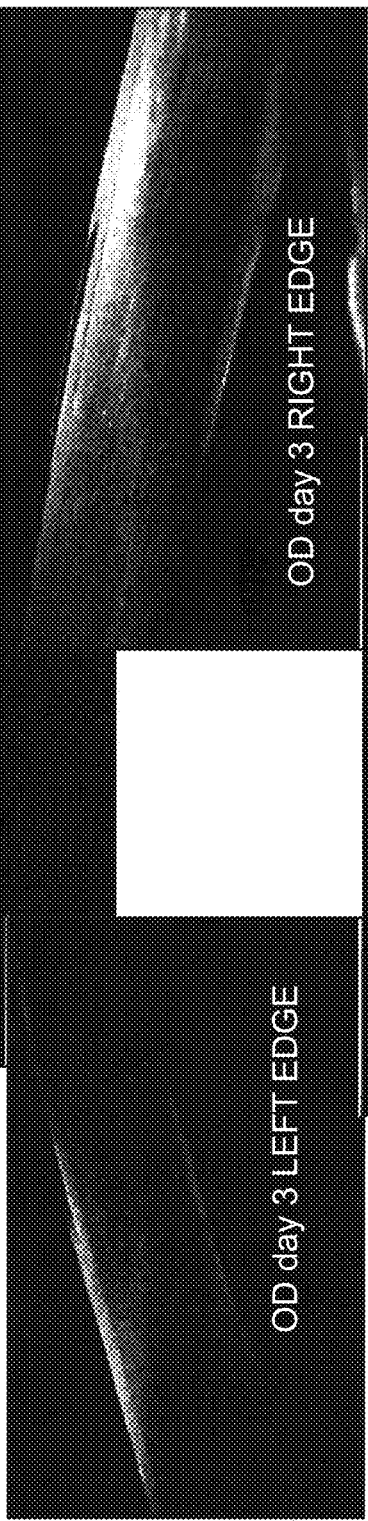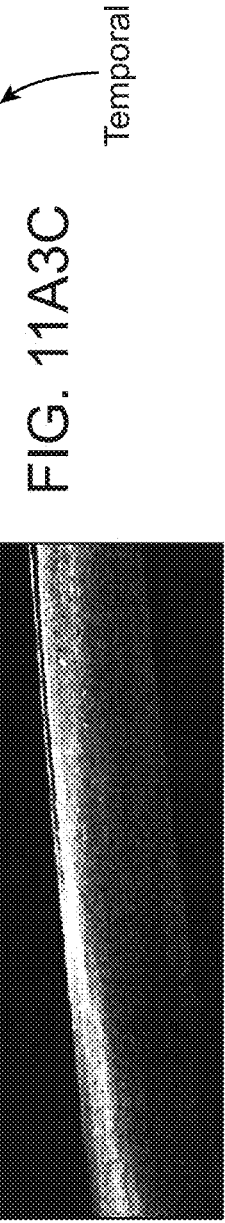
FIG. 11A3A  FIG. 11A3B  FIG. 11A3C  FIG. 11A3D

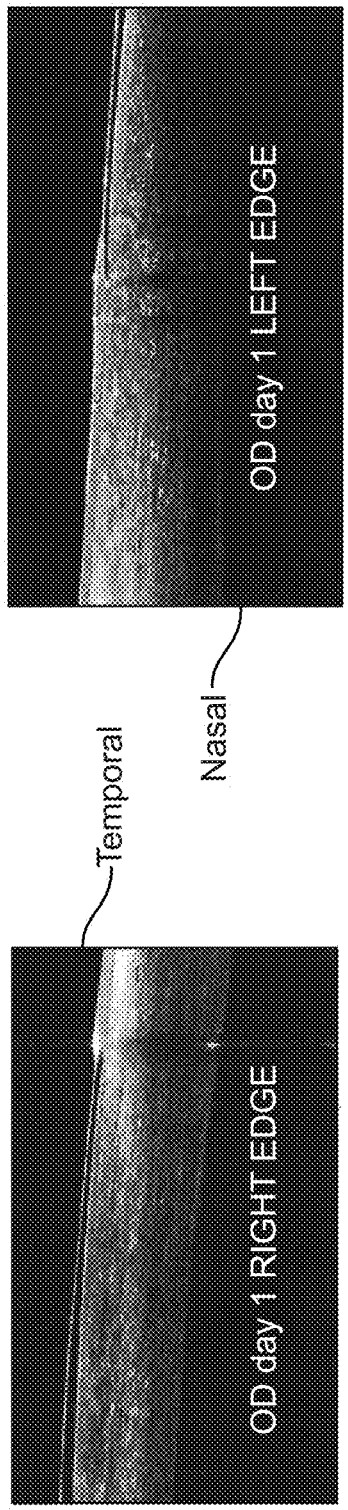
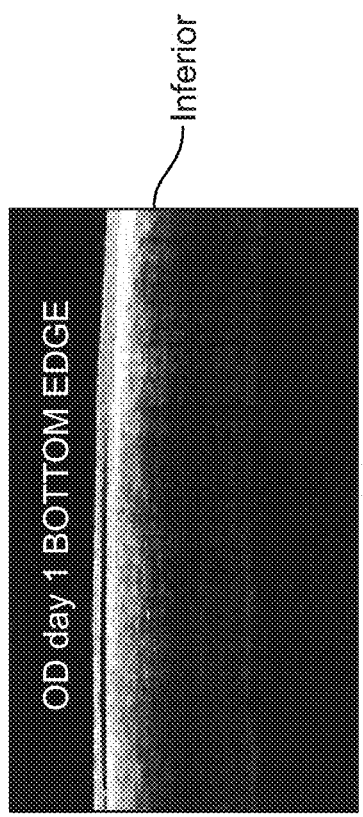
FIG. 12A1B
FIG. 12A1C
FIG. 12A1A

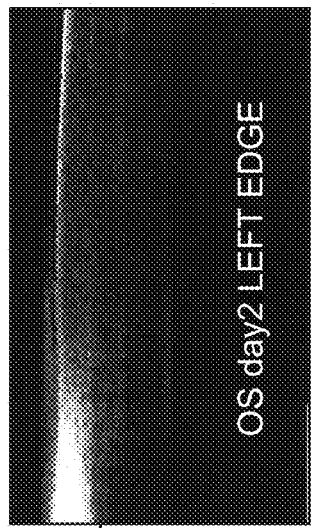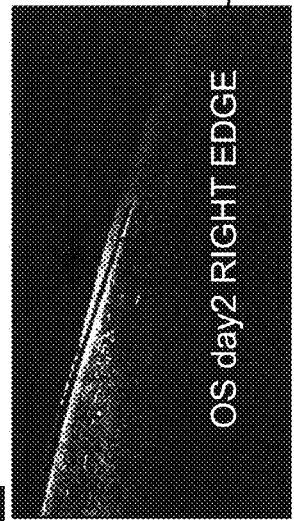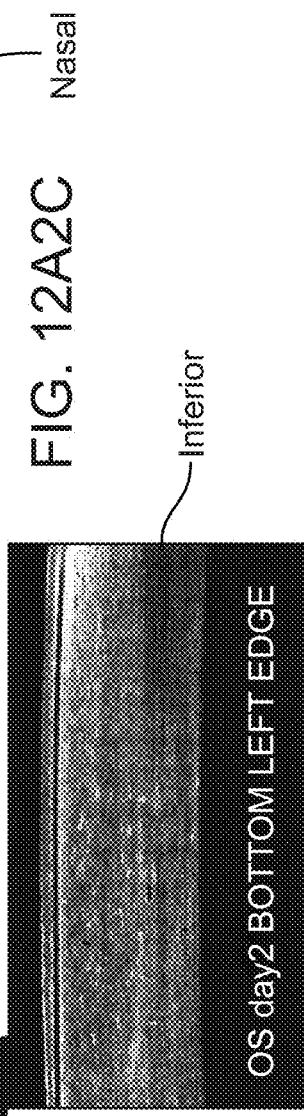
FIG. 12A2A
FIG. 12A2B
FIG. 12A2C
FIG. 12A2D

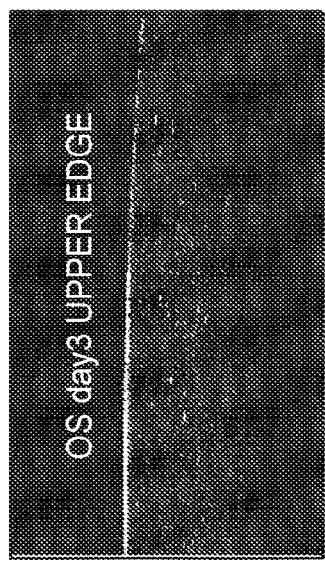
FIG. 12A3A
FIG. 12A3C
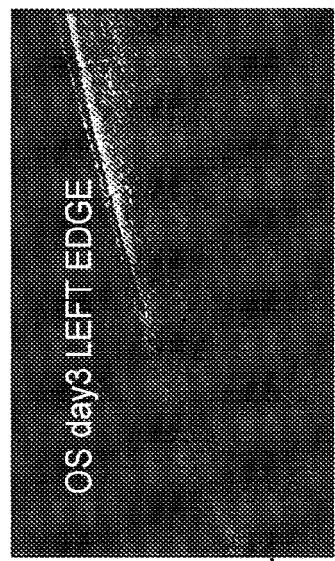
FIG. 12A3B
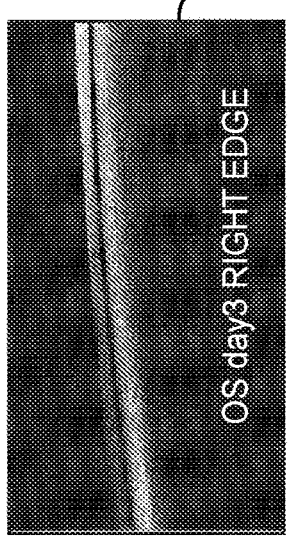
FIG. 12A3 D

CONFORMABLE THERAPEUTIC SHIELD FOR VISION AND PAIN

CROSS-REFERENCES TO RELATED APPLICATIONS

This application is a continuation of U.S. application Ser. No. 14/966,918, filed on Dec. 11, 2015, now allowed, which is a divisional of U.S. application Ser. No. 14/286,605, filed on May 23, 2014, issued as U.S. Pat. No. 9,241,837, which is a continuation of U.S. application Ser. No. 13/894,176, filed on May 14, 2013, issued as U.S. Pat. No. 8,926,096, which is a continuation application of U.S. application Ser. No. 13/503,842, filed on Dec. 4, 2012, issued as U.S. Pat. No. 9,498,385, which entered the U.S. National Phase from International Application No. PCT/US2010/053975, filed on Oct. 25, 2010, which claims the benefit under 35 U.S.C. § 119(e) of U.S. Provisional Application No. 61/322,206 filed on Apr. 8, 2010 and U.S. Provisional Application No. 61/279,613 filed on Oct. 23, 2009, each of which is incorporated by reference in its entirety.

BACKGROUND OF THE INVENTION

The present invention is generally directed to visual rehabilitation and treatment of pain for patients with epithelial defects on the cornea of the eye. Although specific reference is made to epithelial defects following photorefractive keratectomy, embodiments of the present invention can be used to treat epithelial defects from other causes, for example corneal abrasions, trauma, keratoconus, penetrating keratoplasty and dystrophies.

The eye includes several tissues that allow patients to see. The cornea of the eye is an anterior tissue of the eye that is clear in healthy eyes and refracts light so as to form an image on the retina. The retina is a posterior tissue of the eye that senses light from the image formed thereon and transmits signals from the image to the brain. The cornea includes an outer layer of tissue, the epithelium, which protects the underlying tissues of the cornea, such as Bowman's membrane, the stroma and nerve fibers that extend into the stroma and Bowman's. The healthy eye includes a tear film disposed over the epithelium. The tear film can smooth small irregularities of the epithelium so as to provide an optically smooth surface. The tear film is shaped substantially by the shape of the underlying epithelium, stroma, and Bowman's membrane, if present. The tear film comprises a liquid that is mostly water and does include additional components, such as mucoids and lipids. The many nerve fibers of the cornea provide sensation to promote blinking that can cover the cornea with the tear film. The never fibers also sense pain so that one will normally avoid trauma to the cornea and also avoid direct contact of an object to the cornea so as to protect this important tissue.

In the healthy cornea, the proper amount of hydration of the cornea, sometimes referred to as dehydration of the cornea, is maintained such that the cornea remains clear. The cornea includes a posterior endothelial layer that pumps water from the cornea into the adjacent anterior chamber. The epithelium minimizes flow of water from the tear liquid into the cornea, such that the corneal stroma can be maintained with the proper amount of hydration with endothelial pumping. The endothelial pumping of water from the cornea to maintain the proper hydration and thickness of the eye is often referred to as deturgescence.

In patients with epithelial defects, the barrier function of the epithelium is compromised, such that water can enter the cornea through the epithelial defect so as to cause swelling of the corneal stroma. As a result, excessive hydration of the cornea may occur in eyes with epithelial defects. In some instances, excessive hydration that swells the corneal stroma can result in light scattering, or haze, such that an image seen by a patient is degraded. The scattering of light by the corneal stroma can be seen with a slit lamp examination to diagnose the patient, and is sometimes referred to as corneal haze. In addition to potentially causing excess hydration of the cornea, an epithelial defect can expose the nerve fibers of the cornea such that the patient feels pain.

Several known techniques exist to treat corneal epithelial defects, including bandage therapeutic lenses, non-steroidal anti-inflammatories (hereinafter NSAIDS), steroids, antibiotics and analgesics. These known techniques may be somewhat effective in reducing symptoms associated with the epithelial defect. However, many of these known techniques may not provide a barrier to water entry into the corneal stroma, such that the cornea may swell with water and may affect patient vision in at least some instances. For example, a bandage therapeutic lens may be placed over the epithelial defect to cover and protect the corneal tissues under the defect, such as the corneal stroma and nerve fibers. However, in at least some instances the bandage therapeutic lens may not prevent water of the tear from leaking through the epithelial defect into the stroma. Also, a bandage therapeutic lens may slide over the epithelial defect when positioned on the eye in at least some instances, potentially decreasing the therapeutic benefit when the lens slides along the delicate underlying tissue, for example when a patient blinks.

Work in relation to embodiments of the present invention suggests that at least some of the known therapeutic bandage lenses used to treat epithelial defects may actually contribute to corneal edema and pain in at least some instances. At least some of the current bandage lenses may provide less oxygen than would be ideal, and decreased oxygen to the cornea may be related pain and corneal edema in at least some instances. Also, in at least some instances, bandage lenses may be fit loosely on the cornea, such that water can go around the bandage lens and may penetrate the stroma through the epithelial defect.

As the post-ablation cornea may have a complex shape, many of the prior commercially available lenses may not fit the ablated cornea as well as would be ideal, and in at least some instances fitting of lenses can be time consuming and awkward. Commercially available contact lenses having a rigid central RGP portion and a soft peripheral skirt can be difficult and/or time consuming to fit to the ablated cornea and may not fit very well in at least some instances. The ablated cornea may comprise an abrupt change in curvature near the edge of the ablation, and in at least some instances it can be difficult to fit such lenses near the edge of the ablation. Also, at least some of the commercially available contact lenses may not be suitable for extended wear and may be removed each day which can be awkward for a patient.

Although anesthetics such as lidocaine and proparacaine may reduce pain, the overuse of these treatments can delay regeneration of the epithelial tissue over the defect, such that the defect may last longer. Consequently many people with epithelial defects may feel pain and have degraded vision while the epithelial defect heals.

Many people elect to undergo laser vision correction surgery to treat refractive error of the eye, such as near sightedness. With one form of this surgery known as photorefractive keratectomy (hereinafter "PRK"), a large area of the epithelium is removed, for example a 6 to 9 mm area.

Following ablation of the underlying tissues such as the corneal stroma and/or Bowman's membrane, the epithelium grows back over the ablated zone and the de-epithelialized area to cover the area where the epithelium was removed. This re-growth of the epithelium can take three to four days, and at least some of the patients who undergo this surgery may feel pain. In addition, the epithelium may be somewhat irregular while growing back over the corneal stroma, and the irregularities may degrade patient vision in at least some instances. Further, work in relation to embodiments of the present invention suggests that anterior stromal edema, ablated surface irregularities and necrotic cells in the ablated surface area may decrease vision in some instances. Therefore, improved treatment of epithelial defects may result in improved patient comfort and vision following PRK, and possibly other surgeries that remove the corneal epithelium.

In light of the above, it would be desirable to provide improved treatments for epithelial defects of the cornea, such as epithelial defects following PRK. Ideally, these treatments would avoid at least some of the deficiencies of known techniques while providing improved patient comfort and/or vision while the epithelial defect heals.

BRIEF SUMMARY OF THE INVENTION

Embodiments of the present invention provide an improved covering to treat an eye having an epithelial defect, for example an epithelial defect subsequent to refractive surgery such as PRK. The covering can improve regeneration of the epithelium, such that the epithelium can regenerate smoothly and rapidly. The covering may be configured in many ways to encourage regeneration of the epithelium, can resist movement when placed on the eye, and may seal the cornea to restore deturgescence, so as decrease irregularities of the cornea and improve vision. The covering may comprise an inner portion having a modulus and a thickness so as to conform at least partially to the ablated stromal surface and so as to smooth irregularities of the epithelium and ablated stroma, such that the patient can receive the optical benefit of the ablation. The covering may comprise an outer portion that can contact the epithelium or the conjunctiva so as to resist movement and in many embodiments so as to seal the covering to decrease swelling of the cornea. The outer portion can be configured in many ways to contact the cornea or the conjunctiva so as to resist movement and in many embodiments seal the cornea. The outer portion may extend to at least an outer portion of the cornea and may extend to at least the limbus and beyond the cornea so as to contact the conjunctiva and couple to the sclera so as to resist movement.

The inner portion of the covering can be configured in many ways so as to conform at least partially to an ablated stromal surface so as to correct vision. As the inner portion can conform at least partially to the ablated surface, the patient can receive the benefit of the ablation profile that corrects vision. The conformable inner portion may have at least some rigidity so as to smooth the epithelium such that the epithelium regenerates rapidly and is guided with the covering so as to form a smooth layer for vision. The inner portion may comprise a modulus and a thickness corresponding to an amount of rigidity so as to provide pressure on the cornea and smooth irregularities when the inner portion is deflected and conforms at least partially to the cornea. The inner portion may comprise an amount of rigidity within a range from about $1 \times 10^{-4}$ Pa*m$^3$ to about $5 \times 10^{-4}$ Pa*m$^3$ so as to deflect and conform at least partially to the ablated cornea and smooth an inner portion of the ablation with pressure when deflected. The inner portion may comprise a modulus within a range from about 1 MPa to 35 MPa, for example from 4 MPa to about 20 MPa, and may conform at least partially to the ablated surface and smooth corneal irregularities such as stromal and epithelial irregularities. The covering having the inner portion configured to conform at least partially to the ablated stroma can fit many sizes and shapes of the cornea very effectively such that the covering can be easier for a practitioner to fit to the patient and provide a better fit. The inner portion can provide an environment to promote epithelial regeneration and guide regeneration of the epithelium along the covering and ablated surface. The covering may comprise a material having high oxygen permeability, for example silicone, with a wettable coating disposed on at least an upper surface of the covering to inhibit coupling of the covering the eyelid and improve adherence of the covering to the epithelium or the conjunctiva.

In a first aspect, embodiments of the present invention provide, a covering to treat an eye of a patient, in which the eye has an epithelium with a defect and an ablated stroma. The covering comprises an inner portion comprising an inner rigidity to contact the stroma, and an outer portion comprising an outer rigidity to define an enclosure with the inner portion and the ablated stroma to promote growth of the epithelium.

In many embodiments, the enclosure provides an environment to promote growth of the epithelium over the defect within about 2 days of ablation.

In many embodiments, the enclosure comprises a terrarium to promote growth of the epithelium over a defect. For example, the enclosure may comprise a terrarium to promote growth of the epithelium over a defect at least about 6 mm across within about 2 days of a PRK ablation.

In many embodiments, the enclosure comprises a chamber to promote growth of the epithelium over the defect within about 2 days of ablation.

In many embodiments, the inner portion comprises an oxygen permeability Dk parameter of at least about 300. For example, the inner portion may comprise an oxygen permeability Dk parameter of at least about 400, for example, at least about 450.

In many embodiments, the inner portion comprises a wettable surface on at least an upper surface and wherein the inner portion comprises an oxygen permeability Dk parameter of at least about 300. The inner portion may comprise a wettable surface on at least an upper surface, and the inner portion may comprise an oxygen permeability Dk parameter of at least about 400. The inner portion may comprises a wettable surface on at least an upper surface and the inner portion may comprise an oxygen permeability Dk parameter of at least about 450.

In many embodiments, the outer rigidity comprises a rigidity to indent the epithelium when the outer portion is adhered to the cornea.

In many embodiments, the outer rigidity comprises a rigidity to conform to a boundary of the epithelium with the epithelial defect and to indent the epithelium.

In many embodiments, the outer portion comprises a perimeter and wherein the outer rigidity comprises a rigidity to conform to a boundary of the epithelium inward of the perimeter and to indent the epithelium with at least a portion of the perimeter.

In many embodiments, the outer portion comprises a perimeter and wherein the outer rigidity comprises a rigidity to cover at least a portion of the perimeter with the epithelium when the covering is adhered to the cornea. The at least the portion of the perimeter may correspond to an inferior portion of the epithelium disposed at an inferior location of the cornea. The at least the portion of the perimeter may comprise the inferior portion of the epithelium and a superior portion of the epithelium, and the at least the portion of the epithelium may extend over the perimeter a greater distance on the inferior portion of the covering than a superior portion of the covering.

In many embodiments, the outer portion comprises a modulus to remodel the epithelium with an indentation and retain at least a portion of the perimeter of the covering at least partially within the indentation.

In many embodiments, the covering comprises a modulus within a range from about 4 to 20 MPa such that the covering conforms at least partially to an ablated stroma when positioned on the cornea and inhibits irregularities. The covering comprising the can inhibit the irregularities in many ways, for example by providing a guide to epithelial growth such that the epithelium grows smoothly, for example by sealing the cornea to decrease swelling such as central islands, and for example, smoothing of the irregularities.

In many embodiments, the covering comprises a modulus within a range from about 4 to 20 MPa such that the covering conforms at least partially to an ablated stroma when positioned on the cornea and smoothes irregularities.

In many embodiments, the covering comprises an inner portion having an amount of rigidity within a range from about $1 \times 10-4$ to about $5 \times 10-3$ (Pa*m^3) such that the covering conforms at least partially to an ablated stroma and smoothes epithelium when positioned on the cornea and inhibits irregularities. The range can be from about $2 \times 10-4$ to about $4 \times 10-3$ (Pa*m^3).

In many embodiments, the covering comprises an inner portion having a thickness and a modulus such that a first area the covering about 3 mm across deflects about 5 um in response a first pressure when the first pressure is within a first range from about 200 Pa to about 920 Pa, and a second area of the inner portion of the covering deflects about 5 um in response to a second pressure when the second pressure is within a second range from about 25 Pa to about 120 Pa. The second area may comprise the first area. The first range can be from about 365 Pa to about 740 Pa the second range can be from about 45 Pa to about 95 Pa.

In another aspect, embodiments of the present invention provide a method of treating an eye of a patient, the eye having an epithelium with a defect and an ablated stroma, the method comprising:
providing a covering, wherein the covering contacts the ablated stroma and the epithelium around the defect to define an enclosure to promote growth of the epithelium over the ablated stroma.

In another aspect, embodiments of the present invention provide a covering to treat an eye of a patient, the eye having an epithelium with a defect and an ablated stroma, the covering comprising:
an inner portion comprising an inner rigidity to contact the stroma;
an outer portion comprising an outer rigidity to define a guide with the inner portion and the ablated stroma to promote growth of the epithelium along the guide when the outer portion is adhered to the stroma.

In another aspect, embodiments of the present invention provide a covering to treat an eye of a patient, the eye having an epithelium with a defect and an ablated stroma, the covering comprising:
an inner portion comprising an inner rigidity to contact the stroma to correct vision;
an outer portion comprising an outer rigidity to define an enclosure with the inner portion and the ablated stroma to promote growth of the epithelium.

In another aspect, embodiments of the present invention provide a covering to treat an eye of a patient, the eye having an epithelium with a defect, the covering comprising:
an inner portion which covers the defect;
an outer portion comprising a perimeter and a modulus to form an indentation in the epithelium when the epithelium regenerates to cover the defect.

In another aspect, embodiments of the present invention provide a method of treating an eye of a patient, the eye having an epithelium with a defect, the method comprising:
positioning a covering on the cornea to cover the defect, the covering comprising an outer portion comprising a perimeter and a modulus, wherein the covering forms an indentation in the epithelium when the epithelium regenerates to cover the defect.

In another aspect, embodiments of the present invention provide a covering to treat an eye of a patient, the eye having an epithelium with an irregularity on a ablated stroma, the covering comprises a conformable inner portion to cover the irregularity, and the inner portion comprises an upper surface. The irregularity comprising an irregularity profile, and an outer portion is configured to adhere to the epithelium. The upper surface profile corresponds to a profile of the ablated stroma to correct vision and smooth the irregularity when the outer portion adheres to the epithelium.

In many embodiments, the irregularities profile comprises spatial frequencies and the upper surface profile comprises spatial frequencies, and wherein the inner portion comprises a low pass filter such that the upper surface profile spatial frequencies are lower than the spatial frequencies of the irregularity profile to correct vision.

In many embodiments, the inner portion comprises a stretchable material to stretch across the irregularities of the epithelium and smooth irregularities transferred from the irregularity profile in contact with the lower surface to the upper surface profile when the outer portion is adhered to the epithelium. The inner portion may comprise a stretchable material having a thickness profile that smoothes irregularities of the epithelium when the covering is positioned on the cornea. The inner portion may comprises a compressible material to conform to the irregularities of the epithelium with a lower surface and smooth irregularities transferred from the irregularity profile in contact with the lower surface to the upper surface profile when the outer portion is adhered to the epithelium.

In another aspect, embodiments of the present invention provide a method treating an eye of a patient, the eye having an epithelium with an irregularity on a ablated stroma. A covering is provided that comprises a conformable inner portion to cover the irregularity and an outer portion to adhere to the epithelium. The inner portion comprises an upper surface, and the irregularity comprising an irregularity profile. The inner portion is placed over the ablated stroma, and the outer portion adheres to the epithelium and the inner portion conforms to a profile of the ablated stroma to correct vision and smooth the irregularity when the outer portion adheres to the epithelium.

In many embodiments, the irregularities profile comprises spatial frequencies and the upper surface profile comprises spatial frequencies. The inner portion comprises a low pass filter such that the upper surface profile spatial frequencies are lower than the spatial frequencies of the irregularity profile to correct vision.

In many embodiments, the inner portion comprises a compressible material to conform to the irregularities of the epithelium with a lower surface and smooth irregularities transferred from the irregularity profile in contact with the lower surface to the upper surface profile when the outer portion is adhered to the epithelium.

In another aspect, embodiments of the present invention provide a covering to treat an eye of a patient, the eye having an epithelium with a defect. The covering comprises an inner portion to cover the defect, and an outer portion comprising an outer rigidity. The outer portion comprises a superior portion to contact the epithelium superiorly with a superior rigidity and an inferior portion to contact the epithelium inferiorly with an inferior rigidity on the patient, in which the inferior rigidity is less than the superior rigidity.

In many embodiments, the superior portion comprises a superior thickness and the inferior portion comprises an inferior thickness less than the superior thickness. The covering may comprise a single piece of material formed with a mold.

In many embodiments, the superior portion comprises a superior hardness and the inferior portion comprises an inferior hardness less than the superior hardness. The covering may comprise a superior material having a superior hardness and an inferior material having the inferior hardness.

In many embodiments, the covering comprises a marking to align the superior portion superiorly on the patient and the inferior portion inferiorly on the patient.

In many embodiments, the covering is adhered to an applicator and the applicator comprises a marking to align the superior portion superiorly on the patient and the inferior portion inferiorly on the patient.

In another aspect, embodiments of the present invention provide a method of treating an eye of a patient, the eye having an epithelium with a defect. A covering is provided with an outer portion comprising an outer rigidity, the outer portion comprising a superior portion to contact the epithelium superiorly with a first rigidity and an inferior portion to contact the epithelium inferiorly with an second rigidity on the patient, and the first rigidity greater than the second rigidity.

In many embodiments, the inferior portion is aligned with an inferior portion of the eye and the superior portion is aligned with a superior portion of the eye when the covering is positioned on the eye.

In another aspect, embodiments of the present invention provide a covering to treat an eye of a patient, the eye having an epithelium and a stroma, the covering comprises a conformable inner portion comprising a first rigidity to conform to the stroma and guide regeneration of the epithelium, and a conformable outer portion comprising a second rigidity to conform to the epithelium.

In many embodiments, the inner portion comprises a first configuration prior to placement on the cornea and a second configuration when placed on the eye, the second configuration different from the first configuration and conforming substantially to an ablated stromal surface of the cornea.

In many embodiments, the second rigidity is less than the first rigidity.

In many embodiments, the second rigidity is greater than the first rigidity. The outer portion may comprises an annular rim disposed around the inner portion.

In many embodiments, the first rigidity of the inner portion is greater than a rigidity of the epithelium and less than a rigidity of a corneal stroma such that the inner portion smoothes the epithelium when said inner portion conforms to the stroma.

In many embodiments, the epithelium comprises an epithelial rigidity, and the eye comprises a stroma comprising a stromal rigidity greater than the epithelial rigidity. The inner portion comprises a rigidity greater than the epithelial rigidity and less than the stromal rigidity such that the inner portion smoothes the epithelium when the inner portion conforms to the stroma.

In many embodiments, the epithelium comprises an epithelial hardness, and the eye comprises a stroma comprising a stromal hardness greater than the epithelial hardness and wherein the inner portion comprises a hardness greater than the epithelial hardness and less than the stromal hardness such that the inner portion smoothes the epithelium and conforms to the stroma.

In many embodiments, the epithelium comprises an epithelial hardness, and the eye comprises a Bowman's membrane comprising a Bowman's membrane hardness greater than the epithelial hardness. The inner portion comprises a hardness greater than the epithelial hardness and less than the Bowman's membrane hardness such that the inner portion smoothes the epithelium and conforms to the Bowman's membrane.

In many embodiments, the epithelium comprises an epithelial hardness and wherein the eye comprises a stroma comprising a stromal hardness greater than the epithelial hardness and wherein the outer portion comprises a hardness less than the epithelial hardness and less than the stromal hardness such that the outer portion conforms to the epithelium.

In many embodiments, the inner portion comprises silicone and the outer portion comprises silicone. The inner portion may comprise at least one of a silica or resin filler. For example, the inner portion may comprise the resin. The at least the inner portion may comprise an optically clear material comprising silicone and resin.

In many embodiments, at least the inner portion comprises an optically clear material comprising silicone having an index of refraction within a range from about 1.4 to about 1.5.

In many embodiments, the outer portion comprises at least one of silica or resin filler. For example, the outer portion comprises silicone and resin In many embodiments, the inner portion comprises a thickness within a range from about 50 um to about 250 um.

In many embodiments, outer portion comprises a thickness within a range from about 10 um to about 60 um.

In many embodiments, a wettable coating is disposed over at least one of an upper surface or a lower surface of the covering. The wettable coating may comprise a lubricious coating. The wettable coating may comprise a contact angle of no more than about 80 degrees. The wettable coating may comprise a contact angle of no more than about 60 degrees.

In many embodiments, the lower surface may comprise a hydrophobic material, and the lower surface may comprise the inner portion and the outer portion.

In many embodiments, the at least the outer portion comprises a lower surface composed of a sticky, tacky, hydrophobic material.

In many embodiments, the inner portion comprises the lower surface composed of the sticky, tacky, hydrophobic material.

In many embodiments, an upper surface comprises wettable coating extending over at least the inner portion. The wettable coating comprises polyethylene glycol (PEG). The PEG coating can be disposed on a Parylene™ coating.

In many embodiments, the wettable coating comprises a plasma coating. The plasma coating may comprise a luminous chemical vapor deposition (LCVD) film. The plasma coating may comprise at least one of a hydrocarbon, for example CH4, O2 or fluorine containing hydrocarbon, for example CF4

In many embodiments, plasma coating comprises a polyethylene glycol (PEG) coating.

In many embodiments, wettable coating comprises 2-hydroxyethylmethacrylate (HEMA). The HEMA can be disposed on a Parylene™ coating.

In many embodiments, the wettable coating comprises N-vinylpyrrolidone (NVP). The NVP can be disposed on a Parylene™ coating.

In many embodiments, inner portion is affixed to outer portion. The inner portion may comprise a first silicone and the outer portion may comprise a second silicone, and the first silicone of the inner portion can be affixed to the second silicone of the outer portion.

In many embodiments, the covering comprises a single piece.

In many embodiments, the covering comprises a single piece of material formed in a mold.

In many embodiments, an intermediate portion is disposed between the inner portion and the outer portion, the intermediate portion comprising a taper extending from inner portion to outer portion. The taper may comprise a radial width within a range from about 0.5 mm to about 2.0 mm In many embodiments, the outer portion comprises an annular flange extending circumferentially around the inner portion and wherein the outer portion extends radially comprises a radial width within a range from about 0.05 mm to about 1.2 mm In many embodiments, the inner portion comprises a distance across within a range from about 3 to about 8 mm.

In many embodiments, the outer portion comprises a distance across within a range from about 6 to about 12 mm.

In many embodiments, the covering comprises a lower surface disposed on a lower side to contact the eye extending along the inner portion and the outer portion and wherein the lower surface comprises at least one of a spherical surface, a bi-curve surface or an aspheric surface.

In many embodiments, the inner portion of the covering comprises an optical power of no more than about +/−1 D to correct vision of the patient when the inner portion conforms to the ablated surface and smoothes the epithelium.

In another aspect, embodiments of the present invention provide a covering to treat an eye of a patient, the eye having an epithelium. The covering comprises an inner portion comprising an inner first rigidity to smooth the epithelium. An outer portion comprises an outer second rigidity. A conformable intermediate portion is disposed between the inner portion and the outer portion. The conformable intermediate portion comprises a third rigidity to conform to the epithelium, and the third rigidity is less than the first rigidity and the second rigidity.

In many embodiments, the outer second rigidity is greater than the inner first rigidity.

In many embodiments, the outer second rigidity is no more than the inner first rigidity.

In many embodiments, the inner portion comprises a first material to smooth the epithelium and the intermediate portion comprises a soft material to conform to the epithelium. The outer portion may comprise the soft material. The outer portion may comprise the first material. The first material may comprise a rigid material having a Shore A durometer hardness parameter of at least about 60, and the second material may comprise a soft material having Shore A durometer hardness parameter of no more than about 70.

In many embodiments, the first material comprises a first silicone comprising a first hardness and the soft material comprises a second silicone having a second hardness less than the first hardness.

In many embodiments, the inner portion comprises an inner first thickness, the outer portion comprising an outer second thickness, the middle portion comprising a third thickness, and the third thickness is less than the inner first thickness and the outer second thickness.

In many embodiments, the inner portion comprises a first material to smooth the epithelium and the intermediate portion comprises the first material to conform to the epithelium.

In many embodiments, the covering comprises a single piece of material formed from a mold.

In another aspect, embodiments of the present invention provide a covering to treat an eye of a patient, the eye having an epithelium. The covering comprises an inner portion comprising an optical surface. An outer portion comprises an outer perimeter, and the outer perimeter comprises a chamfer to contact the epithelium to seal the cornea.

In another aspect, embodiments of the present invention provide a method of treating an eye of a patient, the eye having an epithelium and a stroma. A covering is placed over the eye. The covering comprises a conformable inner portion comprising a first rigidity and a conformable outer portion comprising a second rigidity, and the conformable inner portion conforms to the stroma and smoothes the epithelium and the outer portion conforms to the epithelium.

In another aspect, embodiments of the present invention provide a method of treating an eye of a patient, the eye having an epithelium and an ablated stromal surface. A covering is placed over the eye, and the covering comprise a conformable inner portion comprising a first rigidity and a conformable outer portion comprising a second rigidity. The conformable inner portion conforms to the ablated surface and smoothes the epithelium, and the outer portion comprising the second rigidity conforms to the epithelium.

In many embodiments, the inner portion of the covering comprises an optical power of no more than about +/−1 D to correct vision of the patient when the inner portion conforms to the ablated surface and smooth the epithelium.

In many embodiments, the inner portion of the covering comprises a substantially uniform thickness to correct vision of the patient when the inner portion conforms to the ablated surface and smooth the epithelium.

In many embodiments, the inner portion comprises a first configuration prior to placement on the cornea and a second configuration when placed on the eye, the second configuration different from the first configuration.

In another aspect, embodiments of the present invention provide a method of manufacturing a therapeutic covering. An inner component is positioned in a mold. A flowable material is injected into the mold to contact the inner component along at least a periphery of the inner component. The flowable material is cured to form the covering. The covering is removed from the mold.

In many embodiments, the first component comprises an optically transparent material.

In many embodiments, the first component comprises an optically transparent material comprising silicone and resin.

In many embodiments, the flowable material comprises silicone.

In many embodiments, the flowable material comprises resin.

In many embodiments, at least an upper side of the covering is coated with a wettable material.

In many embodiments, the covering is placed in a container. The covering can be dried prior to placement in the container. The covering can be sealed in the container in a substantially dry configuration.

In many embodiments, the covering is connected to an applicator and placed in the container in a substantially dry configuration.

In many embodiments, a solvent is evaporated to adhere the covering to the applicator. The solvent may comprises an alcohol, for example.

In another aspect, embodiments of the present invention provide a method of placing a covering on a cornea of an eye having an epithelium with a defect. A dry covering is provided, the covering having a configuration for placement on the eye. The cornea is dried to remove at least some liquid from the cornea. The dry covering is advanced in the configuration toward the eye to contact the epithelium and cover the defect with the dry covering.

In many embodiments, the dry covering is advanced with an applicator adhered to the covering in an expanded configuration.

In many embodiments, covering comprises an outer portion having a lower surface that sticks to the epithelium of the dry eye.

In many embodiments, the lower surface of the outer portion comprises a hydrophobic sticky tacky surface.

In many embodiments, the eye is exposed to a gas to dry the eye.

In many embodiments, the epithelial defect comprises a debridement.

In many embodiments, the epithelial defect comprises a debridement and wherein the eye comprises an ablated stroma within the debridement. The covering can contact the ablated stroma and the epithelium without a liquid disposed between the covering and the epithelium.

In many embodiments, a liquid is not disposed between the covering and epithelium when the covering contacts the epithelium.

In many embodiments, the covering is positioned substantially uniformly on the dried eye.

In many embodiments, the covering is positioned substantially uniformly on the dried eye with an applicator.

In another aspect, embodiments of the present invention provide an applicator to position a covering on an eye. The applicator comprises a support having a surface to contact at least a peripheral portion of the covering to stick to the covering.

In many embodiments, the surface comprises a curved surface. The curved surface may stick to the covering when the curved surface and the at least the peripheral portion each comprise a dry surface without a liquid disposed therebetween. The curved surface may comprise a sticky tacky surface when dry to hold the covering and a slippery surface when wet to release the covering. The curved surface can be configured to adhere to the covering with block adhesion and release the covering in response to peeling of the covering from the curved surface.

In many embodiments, the curved surface comprises silicone.

In many embodiments, the curved surface comprises a wettable coating.

In many embodiments, the support comprises an annular ring having the curved lower surface disposed on a lower side of the ring and inclined to contact the peripheral portion of the covering.

In many embodiments, the support defines an opening sized for a surgeon to view at least a pupil of the eye when the covering is positioned on the eye.

In many embodiments, a handle is affixed to the support for placement on the covering when the handle is grasped by a surgeon.

In many embodiments, the support comprises foam coupled to the covering to position the covering on the eye and to release the covering when the covering is positioned on the eye.

In another aspect, embodiments of the present invention provide an applicator to position a covering on an eye. The applicator comprises a support having a curved surface to contact at least a peripheral portion of the covering. The curved surfaces adheres to the covering when dry and releases the covering when wet.

In another aspect, embodiments of the present invention provide an applicator to position a covering on an eye of a patient. The applicator comprises a support comprising a rigid first component and a second component movable relative to the rigid first component to position the covering on the eye, and the movable component comprises at least a portion viewable therethrough.

In many embodiments, the at least the portion is viewable therethrough from the eye on a first side of the support to an object on a second side of the support opposite the first side when the support and the covering are positioned in front of the eye to place the covering on the eye.

In many embodiments, the at least the portion is viewable therethrough from an operating microscope positioned on the second side of the support to a tissue structure of the eye disposed on the first side when the support and the covering are positioned in front of the eye to place the covering on the eye.

In many embodiments, the rigid component comprises a window. The window of the rigid component may comprise an opening defined with the rigid component and sized to receive the movable component. The at least the portion comprises a window disposed within the window of the support.

In many embodiments, the at least the portion comprises a window composed of a transparent material.

In many embodiments, the at least the portion comprises an inner opening defined with an outer portion of the movable second component.

In many embodiments, the support comprises a first configuration to carry the covering and a second configuration to release the covering. The movable component can urge the covering toward the eye when the support transitions from the first configuration to the second configuration. The movable component peels the covering from the support when the support transitions from the first configuration to the second configuration.

In many embodiments, the movable component comprises a thin transparent flexible sheet coupled to the rigid component to urge the covering toward the eye.

In many embodiments, the rigid component and the movable component define a chamber to urge the covering onto the eye when fluid is passed into the chamber.

In many embodiments, the movable component comprises a popper.

In many embodiments, the movable component comprises an optically transparent material sized to fit within the rigid component to urge the covering toward the eye. The rigid first component may comprise an annulus having an inner diameter, and the movable second component may comprise a disc having a diameter sized to fit within the inner diameter. The movable component can be coupled to the shield to urge the shield toward the eye.

In many embodiments, support comprises a single piece of material formed from a mold, the rigid component comprising the material and the movable component comprising the material wherein the rigid component comprises a thickness greater than the movable component such that a shape of the rigid component is retained substantially when the movable component flexes.

In another aspect, embodiments of the present invention provide a applicator to position a covering on an eye of a patient. The applicator comprises a rigid first component to carry the covering with an outer portion of the covering and position the covering on the eye. A second component is movable relative to the rigid first component to contact an inner portion of the covering and separate the covering from the first rigid component when the covering is positioned on the eye. The movable component may comprise at least a portion viewable therethrough.

In many embodiments, the rigid first component comprises an opening sized to receive second component.

In many embodiments, the rigid first component comprises an opening sized to receive second component.

In many embodiments, the rigid first component comprises a lower inclined surface to stick to the covering at the outer portion, and the second component comprises a lower surface to contact the inner portion of the covering and peel the covering from the lower inclined surface when the second component moves toward the eye.

In many embodiments, a handle is connected to the rigid first component and a structure extending between the handle and the movable component to urge the movable component toward the eye when the handle is grasped by a user.

In another aspect, embodiments of the present invention provide an applicator to position a covering on a cornea of an eye of a patient. The applicator comprises a handle, and a first component to carry the covering and position the covering on the cornea of the eye. A rigid second component is rigidly coupled to the handle and the first component to fix the eye when the covering is positioned on the eye with the first component.

In many embodiments, the first component comprises a first annular portion to couple to the covering and position the covering on the eye, and the second component comprises a fixation ring to fix the eye.

In another aspect, embodiments of the present invention provide an applicator to position a covering on a cornea of an eye of a patient. The applicator comprises a handle, and a first component to carry the covering and position the covering on the cornea of the eye. The applicator comprises a second component to de-enervate the eye with at least one of a substance or cooling when the covering positioned on the cornea with the handle.

In another aspect, embodiments of the present invention provide an applicator to position a covering on a cornea of on an eye of a patient. The apparatus comprises a handle to position the covering on the eye. At least two contact pads to contact the covering are coupled to the handle, in which each pad comprises a lower surface to couple to the covering, and the at least two pads are separated by a distance. The apparatus comprises at least two extensions, in which each extension is coupled to one of the pads and extends between said pad and the handle, and the at least two extensions are inclined relative to the pads and separated such that the patient can view an object when the covering is placed on the eye with the pads separated by the distance.

In many embodiments, the lower surface of each pad comprises an inclined surface, and the extensions are configured to separate to release the covering when the covering is positioned on the cornea.

In many embodiments, the inclined lower surface of each pad is configured to adhere to the covering with block adhesion to carry the covering prior to placement and wherein the extensions are configured to separate the pads along a path to peel the covering away from the covering away from the pads when the pads separate to release the covering.

In many embodiments, each contact pad comprises a roller configured to roll outward along the covering when the pad is pressed toward the eye with the handle.

In many embodiments, each contact pad comprises a concave roller rotationally coupled to said extension to roll outward along the covering when the pad is pressed toward the eye with the handle and the extension.

In another aspect, embodiments of the present invention provide an apparatus to cover an eye. The apparatus comprises a dry covering having an upper surface. A support having a lower surface is coupled to the upper surface to position the covering on the eye and release the covering when the covering is positioned on the eye.

In many embodiments, the lower surface is coupled to an outer portion of the covering to release the covering.

In many embodiments, the lower surface is coupled to an outer portion of the covering with block adhesion to release the covering in response to peeling of the covering from the support.

In many embodiments, the lower surface comprises a non-wettable surface in contact with the dry covering.

In many embodiments, the lower surface comprises a wettable surface coating in contact with the dry covering.

In many embodiments, the dry covering comprises a non-wettable surface in contact with the lower surface.

In many embodiments, the dry covering comprises a wettable surface in contact with the lower surface.

In many embodiments, the lower surface comprises a wettable coating.

In many embodiments, the lower surface extends along a curve to define an opening, and the lower surface comprises an inclined angle along the curve hold the covering for placement on the eye. The dry covering can be adhered to the lower surface and wherein the lower surface releases the covering when wet. The support comprises silicone and the covering comprises silicone. The silicone of the support can contact the silicone of the covering to adhere the covering to the support.

In many embodiments, the covering comprises an upper surface comprising a wettable coating disposed thereon, and the wettable coating of the covering sticks to the lower surface of the support. The wettable coating on the upper surface of the covering can separates from the lower curved surface when wet. The lower surface may comprise a hydrophobic material in contact with the wettable coating on the upper surface of the covering to release the lower curved surface when wet.

In many embodiments, the lower surface comprises a wettable material in contact with the wettable coating on the upper surface of the covering to adhere the lower curved surface to the upper surface when dry and to release the upper surface when wet.

In many embodiments, the dry covering comprises an optically transparent surface having an optical power of no more than about +/−1 D.

In another aspect, embodiments of the present invention provide an method of placing a covering on a cornea of an eye having an epithelium with a defect. A fixation light is provided to a patient to view with the eye. The covering is positioned over the eye of the patient and separated from the cornea of the eye, and the patient views the fixation light when the covering is positioned over the eye and separated from the cornea. The covering is advanced toward the eye to contact and cover the defect when the patient views the fixation light.

In many embodiments, the patient fixates on the fixation light to stabilize the eye when the covering is advanced toward the eye. A surgeon can view the eye through an operating microscope to align the covering with the eye when the covering is advanced toward the eye.

In many embodiments, the covering comprises at least a portion viewable therethrough and wherein the patient fixates on the fixation light with light from the fixation light transmitted through the at least the portion when the covering is advanced toward the eye. The covering may comprise a dry optically transparent covering having an optical power of no more than about +1-1 D when positioned in front of the eye. The at least the portion may comprise a dry anterior surface without a liquid disposed thereon and a dry posterior surface without a liquid disposed thereon and wherein the patient views the fixation target through the dry anterior surface and the dry posterior surface.

In many embodiments, the surgeon views a structure of the eye through the at least the portion to align the covering with the eye when the covering is advanced toward the eye. The structure of the eye may comprise at least one of the epithelial defect, an iris of the eye, a pupil or a limbus of the eye.

In many embodiments, the covering is advanced toward the eye with an applicator coupled to the covering. The applicator may comprise a window, and the patient can views the fixation light through the window when the applicator is advanced toward the eye. The covering can be released from the applicator when the covering is positioned in contact with the cornea.

In many embodiments, the applicator holds the covering in a substantially expanded configuration for placement on the cornea when the covering is advanced toward the eye.

In another aspect, embodiments of the present invention provide a method of removing a covering from an eye. A covering is provided positioned over a regenerated epithelium of the eye. An elongate structure is positioned having a lumen disposed therein, and the lumen extends to an opening on the distal end and the opening is positioned under the covering. A liquid is injected through the opening positioned under the covering so as to separate the covering from the regenerated epithelium along a lower surface of the covering.

In many embodiments, the opening comprises a cross sectional size having a maximum distance across extending a first direction and wherein the first direction is aligned substantially with a lower surface of the covering to inject the liquid along the lower surface of the covering to separate the covering from the regenerated epithelium.

In another aspect, embodiments of the present invention provide a method of removing a covering from an eye having an epithelium and ablated stroma. the covering is provided positioned over a regenerated epithelium substantially covering the ablated stroma. An elongate structure is positioned having a lumen disposed therein. The lumen extends to an opening on the distal end. A liquid is injected to deliver the liquid to a distal end through the opening and under the covering to separate the covering from the regenerated epithelium along a lower surface of the covering.

In another aspect, embodiments of the present invention provide an apparatus to remove covering from an eye. The apparatus comprises an elongate structure having a proximate portion and a distal portion. The elongate structure has a lumen disposed therein to deliver a liquid to a distal end of the distal portion. The lumen extends to an opening on the distal end, and the opening has a sectional size with a first longer dimension across extending in a first direction and a second smaller distance across extending in a second direction. An elongate support extends in an elongate direction, and the elongate support is attached to the proximal portion of the elongate structure and graspable by a user to position the distal end under the covering to align the maximum distance across a lower surface of the covering when the handle is positioned near a temple of the patient.

In another aspect, embodiments of the present invention provide an apparatus to remove a covering from an eye. The apparatus comprises an elongate structure having a lumen disposed therein to deliver a liquid to a distal end, wherein the lumen extends to an opening on the distal end. The opening has a cross sectional size with a first longer dimension across extending in a first direction and a smaller dimension across extending in a second direction. An elongate support extends in an elongate direction, the elongate support graspable by a user to position the distal end under a temporally disposed portion of a perimeter of the covering when the handle is positioned near a temple of the patient. The elongate structure comprises a bend between the support and the distal end and wherein the maximum distance across is aligned with the temporally disposed portion of the perimeter of the covering when the handle is positioned near the temple.

In another aspect, embodiments of the present invention provide a method of treating an eye of a patient following PRK surgery, the eye having an epithelium with a defect and an ablated stroma. A covering is placed over the ablated stroma to cover the epithelial defect and couple to the cornea so as to improve to at least about 20/40 between 24 hours to 72 hours post-op and wherein the patient without the placed covering would have vision of less than about 20/40 between 24 to 72 hours post-op.

In many embodiments, the vision is improved to at least about 20/30 between 24 hours to 72 hours post-op and wherein the patient without the placed covering would have vision of less than about 20/30 between 24 to 72 hours post-op.

In many embodiments, the vision is improved to at least about 20/25 between 24 to 72 hours post-op and wherein the patient without the placed covering would have vision of less than about 20/25 between 24 to 72 hours post-op.

In many embodiments, the vision is improved to at least about 20/20 between 24 hours to 72 hours post-op and wherein the patient without the placed covering would have vision of less than about 20/30 between 24 to 72 hours post-op.

In another aspect, embodiments of the present invention provide a method of treating an eye of any of a population of patients following PRK surgery, the population of PRK patients having at least about 40% of patients seeing 20/40 or better between 24 to 72 hours post-op. The eye has an epithelium with a defect and a successfully ablated stroma.

A covering is placed over the ablated stroma to cover the epithelial defect and improve vision such that the patient is a member of the population.

In many embodiments, the population of patients has at least about 60% of patients seeing 20/40 or better between 24 to 72 hours post-op.

In many embodiments, the population of patients has at least about 80% of patients seeing 20/40 or better between 24 to 72 hours post-op.

In many embodiments, the population of patients has at least about 90% of patients seeing 20/40 or better between 24 to 72 hours post-op.

In another aspect, embodiments of the present invention provide a covering to treat an eye of a patient following PRK surgery, the eye having an epithelium with a defect and an ablated stroma. The covering comprises a curved body to couple to the cornea and cover the ablated stroma and the epithelial defect so as to improve vision to at least about 20/40 between 24 to 72 hours post-op, and the eye without the covering would have vision of less than 20/40 between 24 to 72 hours post-op.

In many embodiments, the vision is improved to at least about 20/30 between 24 hours to 72 hours post-op and wherein the patient without the placed covering would have vision of less than about 20/30 between 24 to 72 hours post-op.

In many embodiments, the vision is improved to at least about 20/25 between 24 to 72 hours post-op and wherein the patient without the placed covering would have vision of less than about 20/25 between 24 to 72 hours post-op.

In many embodiments, the vision is improved to at least about 20/20 between 24 hours to 72 hours post-op and wherein the patient without the placed covering would have vision of less than about 20/30 between 24 to 72 hours post-op.

In another aspect, embodiments of the present invention provide a covering to treat an eye of a patient following PRK surgery, the PRK surgery comprising epithelial removal from a region of the cornea of the eye and ablation of stroma of the cornea underlying the region such that the eye, with an appropriate standard contact lens disposed on the cornea and without the treatment, would have visual acuity of worse than 20/40 throughout the period between 24 to 72 hours after the PRK surgery. The covering comprises a curved body with a concave surface receiving the cornea so as to cover the ablated stroma and a convex surface over which an eyelid passes without dislodging the curved body from the cornea during blinking of the eye. The curved body is transparent and engagement of the curved body against the cornea mitigating the epithelial removal so as to improve the visual acuity of the eye therethrough to at least about 20/40 between 24 to 72 hours after the PRK surgery.

In many embodiments, the vision is improved to at least about 20/30 between 24 hours to 72 hours post-op and wherein the patient without the placed covering would have vision of less than about 20/30 between 24 to 72 hours post-op.

In many embodiments, the vision is improved to at least about 20/25 between 24 to 72 hours post-op and wherein the patient without the placed covering would have vision of less than about 20/25 between 24 to 72 hours post-op.

In many embodiments, the vision is improved to at least about 20/20 between 24 hours to 72 hours post-op and wherein the patient without the placed covering would have vision of less than about 20/30 between 24 to 72 hours post-op.

In another aspect, embodiments of the present invention provide a covering to treat an eye of any of a population of patients following PRK surgery, the population having at least about 40% of patients seeing 20/40 or better between 24 to 72 hours post-op, the eye having an epithelium with a defect and a successfully ablated stroma. The covering comprises a curved body to couple to the cornea and cover the ablated stroma and epithelial defect such that the patient is a member of the population.

In another aspect, embodiments of the present invention provide a covering to treat an eye of a patient following PRK surgery, the patient included within a population of PRK patients receiving PRK surgery, each PRK surgery comprising epithelial removal from a region of the cornea of the associated eye and ablation of stroma of the cornea underlying the region, the epithelial removal degrading short-term visual acuities of the eyes after the PRK. The covering comprises a curved body with a concave surface receiving the cornea so as to cover the ablated stroma and a convex surface over which an eyelid passes without dislodging the curved body from the cornea during blinking of the eye, the curved body being transparent and mitigating the short-term visual acuity degradation when disposed on the eye. The mitigation is sufficient that 40% of the eyes of the patients of the population would have visual acuities of at least about 20/40 between 24 to 72 hours after the PRK surgery.

In many embodiments, the population of patients has at least about 60% of patients seeing 20/40 or better between 24 to 72 hours post-op.

In many embodiments, the population of patients has at least about 80% of patients seeing 20/40 or better between 24 to 72 hours post-op.

In many embodiments, the population of patients has at least about 90% of patients seeing 20/40 or better between 24 to 72 hours post-op.

In another aspect, embodiments of the present invention provide a covering to treat an eye of a patient. The covering comprises a curved body to fit they eye. The body has a modulus within a range from about 4 MPa (Mega Pascal's) to about 20 MPa.

In many embodiments, the body comprises an elastomer. The elastomer may comprise silicone polymer formed with one or more of vinyl polymerization, peroxide polymerization or hydrosilation.

In many embodiments, the body comprises contact lens having a central lens portion having a center stiffness of at least about 2 psi*mm2 coupled to an outer lenticular junction portion having a lenticular junction stiffness of at least about 5 psi*mm2.

In many embodiments, the body comprises an amount of water within a range from about 0 to 35% and wherein the body comprises a Dk of 100 or more. The body may comprise silicone comprising one or more of silicone elastomer or silicone hydrogel. The range of water can be from about 0 to 10% and the Dk is 100 or more. The body may comprise the silicone elastomer and the range of water is from about 0 to 5% and the Dk is 100 or more.

In many embodiments, the body comprises the silicone hydrogel and the silicone hydrogel comprises a low ion permeability and the range of water is from about 5% to about 35% and the Dk is 100 or more. The low ion permeability may comprise an Ionoton Ion Permeability Coefficient of no more than about 0.25×10−3 cm2/sec. The low ion permeability may comprise an Ionoton Ion Permeability Coefficient of no more than about 0.08×10−3 cm2/sec. The low ion permeability may comprise an Ionoton Ion Permeability Coefficient of no more than about 2.6×10−6 mm2/min. The low ion permeability may comprise an Ionoton Ion Permeability Coefficient of no more than about $1.5 \times 10^{-6}$ mm2/min.

In many embodiments, the body comprises a wettable surface having a tear break up time of no less than about five seconds when placed on the eye. The wettable surface may comprise a coating of one or more of luminous chemical vapor deposition (LCVD), hydrogel, 2-hydroxyethylmethacrylate (HEMA), methacrylic acid (MA), methyl methacrylate (MMA), N,N-dimethylacrylamide (DMA); N-vinyl pyrrolidone (NVP), phosphorylcholine (PC), poly vinyl alcohol (PVA) or polyvinyl pyrrolidone (PVP), tris-(trimethylsiloxysilyl) propylvinyl carbamate (TPVC); N-carboxyvinyl ester (NCVE); silicone hydrogel, poly[dimethylsiloxyl]di[silylbutanol]bis[vinyl carbamate] (PBVC); silicate, plasma treated silicone hydrogel, plasma coating producing glassy islands, 25 nm plasma coating with high refractive index.

In many embodiments, wettable surface comprises the material of the body. The material of the body and surface may comprise hydrogel. The material of the body comprises an optically clear silicone elastomer comprising silicate, and the silicone elastomer may comprise silicate treated with plasma to generate the wettable surface.

In many embodiments, the wettable surface comprises hydrogel and the body comprises silicone elastomer and wherein the hydrogel is disposed silicone elastomer.

In many embodiments, the body comprises an inner portion and an outer portion, wherein the inner portion comprises a lower surface having a first radius of curvature to fit an ablated region of a cornea of the eye and the outer portion comprises a lower surface having a second radius of curvature to fit an unablated region of the cornea of the eye.

In many embodiments, the body comprises a lower surface having an oblate shape to fit an ablated region of a cornea of the eye and to fit an unablated region of the cornea.

In many embodiments, the body comprises a first curved portion, a second curved portion, and a third curved portion, wherein the first curved comprises a first lower surface having a first radius of curvature to fit an ablated region of a cornea the eye, the second curved portion comprising a second lower surface having a second radius of curvature to fit an unablated region of the cornea of the eye, the third curved portion comprising a third lower surface having a third radius of curvature to fit a sclera of the eye.

In many embodiments, the second radius of curvature to fit the unablated cornea is less than the third radius of curvature to fit the sclera.

In many embodiments, the curved body comprises an inner portion to seal the cornea and an outer portion having fenestrations extending through a thickness of the body to pass a medicament to treat pain when the lens is adhered to the cornea.

In another aspect, embodiments provide a method of treating an eye an eye of a patient. A covering comprising a curved body is placed on the cornea of the eye. The body has a modulus within a range from about 4 MPa (Mega Pascal's) to about 20 MPa.

In many embodiments, the eye comprises an epithelium and an ablated stroma and wherein covering adheres to the epithelium and conforms at least partially to the ablated stroma to improve the vision of the patient. The covering may inhibit irregularities of one or more of the epithelium or the ablated stroma when the covering conforms at least partially to the ablated stroma. For example, the covering may smooth irregularities of the cornea.

In another aspect, embodiments provide a covering to treat an eye of a patient. The covering comprises a curved body to fit the eye. The body comprises an inner portion and an outer portion. The inner portion has an amount of rigidity within a range from about $1 \times 10E-4$ to about $5 \times 10E-4$ Pa*m^3 (Pascal*meters cubed), the outer portion has an amount of rigidity less than the inner portion. The range can be from about $2 \times 10E-4$ to about $4 \times 10E-4$ Pa*m^3 (Pascal*meters cubed).

In many embodiments, the inner portion comprises a first layer of a first material and a second layer of a second material, the first material comprising a soft material having a modulus within a range from about 0.1 to about 5 MPa, the second material having a modulus within a range from about 5 to about 1900 MPa.

In many embodiments, the inner portion comprises a third layer of a third material having a third modulus within a range from about 0.1 to about 5 MPa.

In many embodiments, the first material comprises a first silicone and the second material and the third material comprise a second silicone, the first silicone comprising a first modulus within a first range from about 5 to 35 MPa, the second silicone comprising a modulus from about 0.1 to 5 MPa.

In many embodiments, the inner portion comprises an RGP material and the outer portion and the third portion comprise a hydrogel.

In many embodiments, the inner portion comprises a first curved portion and the outer portion comprises a second curved portion and a third curved portion. The first curved portion comprises a first lower surface having a first radius of curvature to fit an ablated region of a cornea the eye. The second curved portion comprises a second lower surface having a second radius of curvature to fit an unablated region of the cornea of the eye. The third curved portion comprises a third lower surface having a third radius of curvature to fit a sclera of the eye.

In many embodiments, the first radius of curvature comprises an apical radius of curvature and the second radius of curvature corresponds to a conic constant.

In many embodiments, the third radius of curvature comprises no more than about 10 mm and a modulus of no more than about 5 MPa and a thickness of no more than about 200 um so as to stretch substantially and resist movement of the inner portion when placed on the sclera.

In many embodiments, the third radius of curvature comprises no more than about 9 mm and an amount of rigidity of no more than about 4E-5 Pa*m^3 so as to stretch substantially for comfort and resist movement of the inner portion when placed on the sclera.

In many embodiments, the third curved portion comprises a maximum dimension across within a range from about 12 to 16 mm to contact the conjunctiva and couple to the sclera of the eye.

In many embodiments, the range is from about 14 to 16 mm to resist movement of the inner portion when the third curved portion is placed on the conjunctiva and coupled to the sclera.

BRIEF DESCRIPTION OF THE DRAWINGS

FIG. 1-1A shows an ablated eye immediately following refractive surgery resulting in an epithelial defect, suitable for incorporation in accordance with embodiments of the present invention;

FIG. 1-1B shows an ablated eye about 1 day following refractive surgery resulting in an epithelial defect, suitable for incorporation in accordance with embodiments of the present invention:

FIG. 1-1C shows an ablated eye when the epithelium has regenerated following refractive surgery resulting in an increased epithelial thickness centrally at about 3 days, suitable for incorporation in accordance with embodiments of the present invention:

FIG. 1-2A shows a covering positioned on an eye having an epithelial defect, in which the covering abuts the cornea to seal the cornea, in accordance with embodiments of the present invention:

FIG. 1-2B shows a smooth layer of regenerated epithelium substantially cover an ablated profile, in accordance with embodiments of the present invention;

FIG. 1A shows a covering positioned on an eye having an epithelial defect, in which an outer portion of the covering abuts and conforms at least partially to the cornea to seal the cornea, in accordance with embodiments of the present invention:

FIG. 1A1 shows a covering positioned on an eye and blinking of the eye, in accordance with embodiments of the present invention:

FIG. 1B1 shows a covering sized to seal a cornea, in accordance with embodiments of the present invention:

FIG. 1B2 shows the covering conforming to ablated stromal tissue and guiding regeneration of the epithelium over the ablated stroma, so as to promote vision, in accordance with embodiments of the present invention;

FIG. 1B2A shows a covering forming an indentation in the epithelium such that the epithelium extends over at least a portion of the perimeter of the covering, in accordance with embodiments of the present invention;

FIG. 1B2B shows a covering forming an indentation in the epithelium, in accordance with embodiments of the present invention:

FIG. 1B2C shows a covering abutting the cornea to seal the cornea without forming a substantial indentation in the epithelium, in accordance with embodiments of the present invention:

FIG. 1C shows a covering comprising a single piece of material having an inner thickness greater than an outer thickness, in accordance with embodiments of the present invention;

FIG. 1C1 shows a covering as in FIGS. 1-2A to 1B2 having an inner portion comprising an inner thickness and an inner material and an outer portion comprising an outer thickness and an outer material, in which the inner thickness is greater than the outer thickness, in accordance with embodiments of the present invention;

FIG. 1C1A shows a covering as in FIG. 1C1 adhered to the cornea with a smooth upper surface and a lower surface conforming to irregularity of the cornea comprising a central island of the stroma, in accordance with embodiments of the present invention;

FIG. 1C2 shows a covering as in FIGS. 1-2A to 1B2 having an inner portion comprising an inner thickness and an inner material and an outer portion comprising an outer thickness and an outer material, in which the inner thickness is greater than the outer thickness and the outer material extends around the inner material, in accordance with embodiments of the present invention;

FIG. 1C2A shows a covering as in FIG. 1C1 adhered to the cornea with a smooth upper surface and a lower surface conforming to irregularity of the cornea near the edge of the ablation, in accordance with embodiments of the present invention;

FIG. 1G shows a covering comprising an inner portion and an outer portion comprising a taper, in accordance with embodiments of the present invention;

FIG. 1G1 shows a covering comprising an inner portion and an outer portion comprising a taper and an outer rim of substantially uniform thickness peripheral to the taper, in accordance with embodiments of the present invention;

FIGS. 1G1A to 1G1G show a covering as in FIG. 1G1 and dimensions suitable for use with experiments, clinical studies and patient treatment in accordance with embodiments;

FIG. 1H1 shows spatial frequency and elevation smoothing of an epithelial irregularity transferred to a front surface of a covering as in FIG. 1-2A, in accordance with embodiments.

FIG. 1H2 shows spatial frequency and elevation smoothing of the epithelial irregularity with a plot of height relative to a reference sphere for the upper surface of the covering and the upper surface of the irregularity;

FIG. 1I1 shows inhibition of transfer of an epithelial irregularity to a front surface of a covering, in accordance with embodiments.

FIG. 1I2 shows elevation smoothing of the epithelial irregularity with a plot of height relative to a reference sphere for the upper surface of the covering and the upper surface of the irregularity;

FIG. 1I3 shows a thickness profile of the covering as in FIG. 1I2 so as to smooth the front surface of the covering, in accordance with embodiments of the present invention;

FIG. 1J1 shows a covering having a bicurve profile to fit an ablated cornea, in accordance with embodiments of the present invention;

FIG. 1J2 shows a covering having an oblate profile to fit an ablated cornea, in accordance with embodiments of the present invention;

FIG. 1J3 shows a covering having a tricurve profile to fit sclera and an ablated cornea, in accordance with embodiments of the present invention;

FIG. 1J4 shows a covering having a curved profile to fit sclera and an oblate profile to fit ablated cornea, in accordance with embodiments of the present invention;

FIG. 1J5 shows a covering having a tricurve profile to fit sclera and an ablated cornea similar to FIG. 1J3, in accordance with embodiments of the present invention;

FIG. 1J6 shows a tapered edge of the covering having a tricurve profile to fit sclera and an ablated cornea as in FIG. 1J5;

FIG. 2A shows surgical placement of a covering on an eye having an epithelial defect with an applicator, in accordance with embodiments of the present invention:

FIG. 2A1 shows a surgeon's view of the eye through the applicator as in FIG. 2A;

FIG. 2A2 shows a patient's view of a fixation light through the applicator as in FIG. 2A;

FIG. 2B shows a covering coupled to an applicator for placement on a cornea as in FIG. 2A, in accordance with embodiments of the present invention;

FIG. 2C shows an applicator coupled to a covering with block adhesion and peeling of the covering from the applicator with a movable component, in accordance with embodiments of the present invention;

FIG. 2C1 shows an applicator coupled to a covering with foam to adhere the covering to the applicator when dry and application of a liquid to release the covering from the applicator when wet, in accordance with embodiments of the present invention;

FIG. 2D1 shows a covering coupled to an applicator with adhesion, in accordance with embodiments of the present invention;

FIG. 2E shows an applicator comprising a rigid component and a flexible component, in accordance with embodiments of the present invention;

FIG. 2E1 shows coupling of a covering to an applicator as in FIG. 2E, in accordance with embodiments of the present invention;

FIG. 2J shows an applicator and a covering with the applicator comprising a hinge to release the covering, in accordance with embodiments of the present invention;

FIGS. 2K1 and 2K2 show side and top views, respectively, of an applicator and a covering with the applicator comprising a compressed structure that is released so as to deliver the covering to the cornea, in accordance with embodiments of the present invention;

FIG. 2K3 shows the applicator as in FIGS. 2K1 and 2K2 in a released configuration to deliver the covering to the cornea, in accordance with embodiments of the present invention;

FIGS. 5B1 and 5B2 shows an apparatus 530 comprising covering 100 and an applicator 200 stored in a sterile compartment of a container, in which the container comprises a support surface 534 with the covering 100 disposed thereon in a channel 532 sized to receive the applicator 200. The channel 532 can guide the applicator onto the covering when the covering is advanced in the channel to couple to the applicator. The covering can be positioned on the cornea with the applicator.

FIG. 5B3 shows an applicator with a support coupled to a handle with a joint disposed between the support and the handle to move the handle when the support is coupled to the eye, in accordance with embodiments of the present invention;

FIG. 5C1 shows an apparatus comprising a removal tool, in accordance with embodiments of the present invention;

FIG. 5C2 shows the distal portion comprising the tip of the removal tool as in FIG. 5C1.

FIG. 5C3 shows the apparatus of FIG. 5C1 aligned with the patient;

FIG. 5C4 shows the long dimension 568L of the cross section of the opening of tip 568 aligned substantially with a plane of the pupil and a peripheral temporal portion of the covering when the handle is positioned near the temple of the patient;

FIG. 6 shows a mold to form a covering and comprising a solid an inner component placed therein prior to injection of a flowable material, in accordance with embodiments of the present invention;

FIGS. 11A1A to 11A1D show OCT images of portions of the soft covering from, respectively, the superior portion of the covering, the nasal portion of the covering, the temporal portion of the covering and the inferior portion of the covering at 48 hours post-op on the right eye (OD);

FIGS. 11A2A to 11A2D show OCT images of portions of the soft covering from, respectively, the superior portion of the covering, the nasal portion of the covering, the temporal portion of the covering and the inferior portion of the covering at 48 hours post-op on the left eye (OS);

FIGS. 11A3A to 11A3D show OCT images of portions of the soft covering from, respectively, the superior portion of the covering, the nasal portion of the covering, the temporal portion of the covering and the inferior portion of the covering at 72 hours post-op on the right eye (OD);

FIGS. 12A1A to 12A1C show OCT images of portions of the rigid covering from, respectively, the temporal portion of the covering, the nasal portion of the covering and the inferior portion of the covering at 24 hours post-op on the right eye (OD);

FIGS. 12A2A to 12A2D show OCT images of portions of the rigid covering from, respectively, the superior portion of the covering, the temporal portion of the covering, the nasal portion of the covering and the inferior portion of the covering at 48 hours post-op for on the left eye (OS); and FIGS. 12A3A to 12A3D show OCT images of portions of the rigid covering from, respectively, the superior portion of the covering, the temporal portion of the covering, the nasal portion of the covering and the inferior portion of the covering at 72 hours post-op on the left eye (OS).

DETAILED DESCRIPTION OF THE INVENTION

Figure 1:
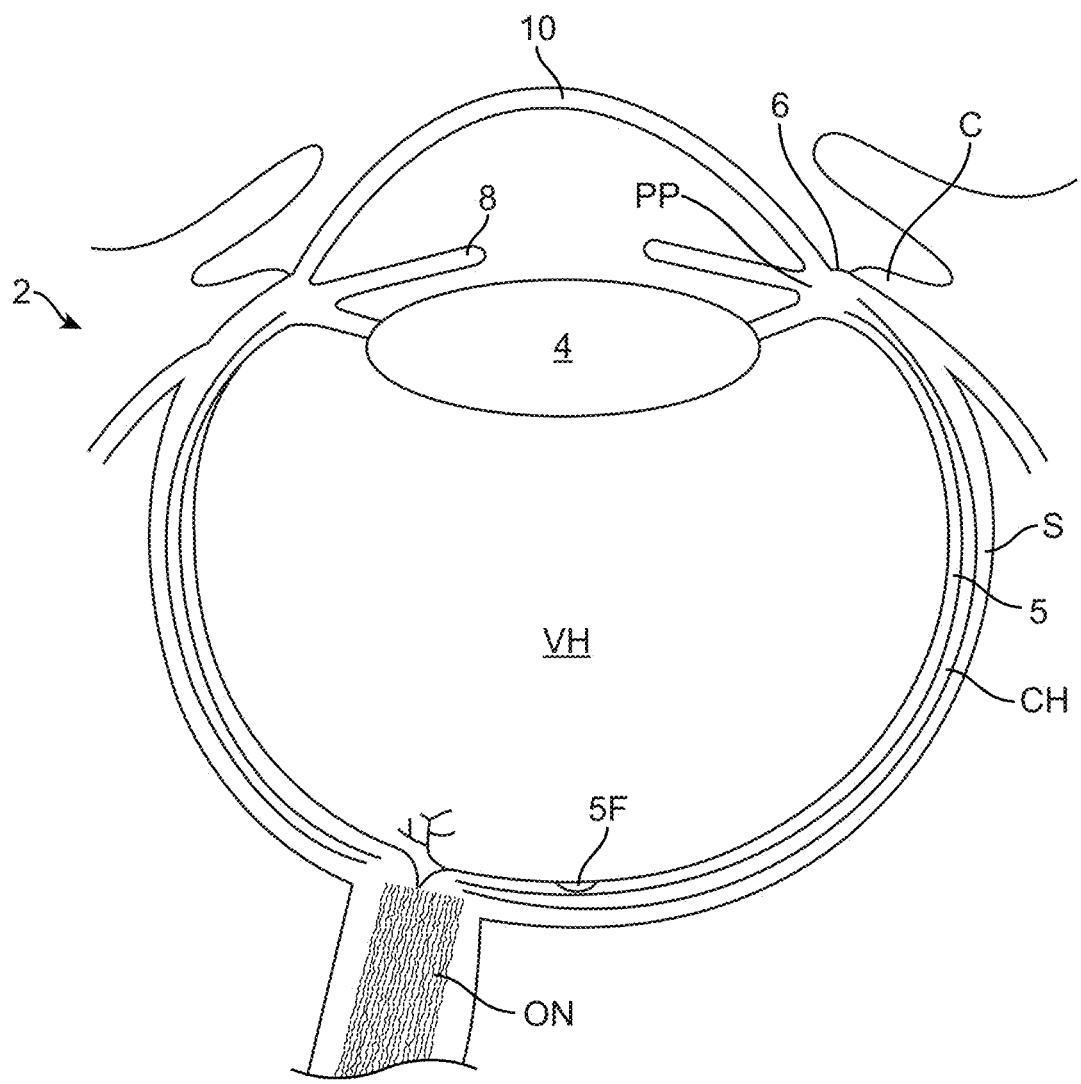
FIG. 1 shows an eye suitable for incorporation of the covering as described herein, in accordance with embodiments of the present invention.

Embodiments of the present invention as described herein can be combined with the therapeutic covering device for pain management and vision as described in U.S. patent application Ser. No. 12/384,659, filed Apr. 6, 2009, entitled "Therapeutic Device for Pain Management and Vision", the full disclosure of which is incorporated herein by reference and suitable for combination in accordance with some embodiments of the present invention as described herein.

The embodiments described herein can be used to treat eyes in many ways with a covering. Although specific reference is made to treating epithelial defects of the eye, the covering described herein can be used for long term vision correction with extended wear contact lenses that inhibit swelling of the cornea when the covering is positioned on the eye for an extended period.

The coverings as described herein can seal the cornea, so as to restore deturgescence of the cornea to decrease pain and improve vision. The covering can be configured in many ways to seal the cornea, and the covering comprises a substantially oxygen permeability to promote growth of the epithelium and to guide the growth of the epithelium such that the epithelium regenerates smoothly for patient vision. The restoration of the deturgescence of the cornea can decrease irregularities of the cornea such as ablated stromal irregularities, for example central islands. The sealing of the cornea with the environment to promote epithelial regeneration can result in improved epithelial smoothness and an improved profile of the ablated stromal surface under the regenerating epithelium.

In many embodiments, the covering comprises an at least partially conformable portion, such that the at least partially conformable portion can one or more of match or grossly approximate the corrected corneal curvature to as to provide vision of at least about 20/30, and such that the at least partially conformable portion substantially does not conform to the corneal irregularities caused by epithelial healing and edema, such as irregularities of the epithelium and central islands that may appear post-ablation in ablated eye.

In many embodiments, the at least partially conformable portion of the covering can be configured so as to conform at least partially to the epithelium when the covering is positioned on the epithelium so as to deflect the epithelium. The epithelium can conform to the covering so as to seal the covering, for example with deformation of the epithelium such as with one or more of indentation or overgrowth of the epithelium around a perimeter of the covering.

In many embodiments, the curvature of the covering can match substantially the profile of the ablated region, so as to provide visions of at least about 20/30 when positioned on the cornea.

As used herein, mathematical equations and scientific notation can be used to values in many ways understood by a person of ordinary skill in the art, for example so as to express data in accordance with notations used in many commercially available spreadsheets such as Excel™ commercially available from Microsoft. As used herein the symbol "E" can be used to express an exponent in base 10, such that 1E1 equals about 10, 2E1 equals about 20, and 4E2 equals about 400. As used herein the symbol "^" can be used to express an exponent, such that A^B equals $A^B$. Units can be expressed in many ways and as would be understood by a person of ordinary skill in the art, for example "m" as meters, "Pa" as the Pascal unit for pressure, "MPa" as Mega Pascal.

FIG. 1 shows an eye 2 suitable for incorporation of the covering 100 as described herein. The eye has a cornea 10 and a lens 4 configured to form an image on the retina 5, and the image can form on a fovea 5F corresponding to high visual acuity. The cornea can extend to a limbus 6 of the eye, and the limbus can connect to a sclera S of the eye. The eye 2 has a pars plana PP located near limbus 6. A conjunctiva C of the eye can be disposed over the sclera. The lens can accommodate to focus on an object seen by the patient. The eye has an iris 8 that defines a pupil 9 that may expand and contract in response to light. The eye also comprises a choroid CH disposed the between the sclera 7 and the retina 5. The eye has a vitreous humor VH extending between the lens and the retina. The retina 5 senses light of the image and converts the light image to neural pulses that are processed and transmitted along an optic nerve ON to the brain of the patient.

Figures 1, 1A:
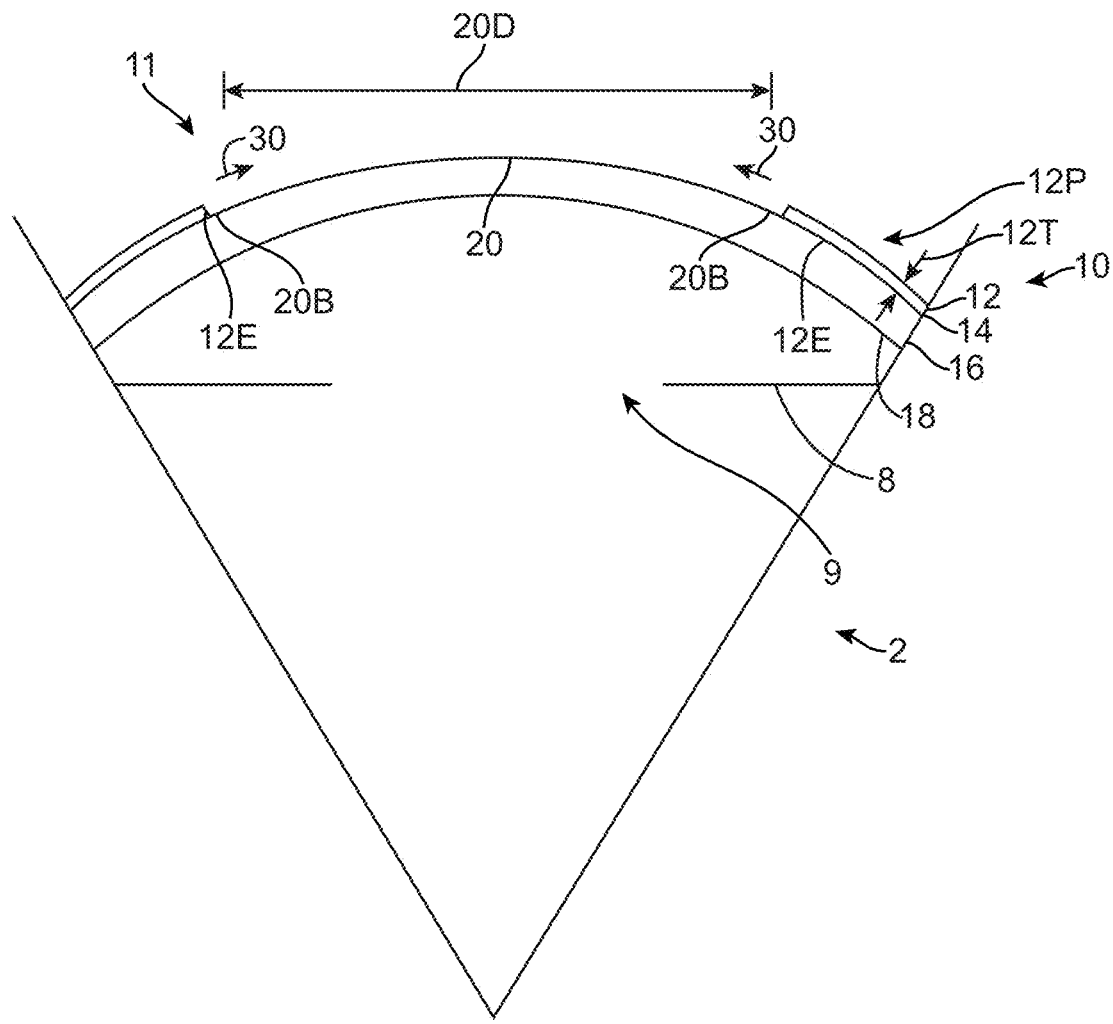

FIG. 1-1A shows an ablated eye immediately following refractive surgery, for example PRK surgery resulting in an epithelial defect. The eye 2 comprises an iris 8 that defines a pupil 9, through which light passes such that the patient can see. Cornea 10 includes an epithelium 12 disposed over a stroma 16. The epithelium 12 comprises a thickness 12T that can be about 50 um. A tear liquid covers the anterior surface of epithelium 12. In at least humans, primates and some birds, a Bowman's membrane 14 is disposed between epithelium 12 and stroma 16. Bowman's membrane 14 comprises an acellular substantially collagenous tissue with a thickness of about 5 to 10 microns. Stroma 16 comprises a substantially collagenous tissue with keratocytes disposed therein. In some animals, Bowman's membrane may be absent and the epithelium may be disposed adjacent to the stromal layer. An endothelium 18 is disposed under stroma 16. Endothelium 18 comprises a layer of cells that pump water from cornea 10 toward iris 8. Tear liquid also covers surfaces of the cornea that are exposed by the epithelial defect, such as an exposed surface of Bowman's membrane and an exposed stromal surface.

In a normal healthy eye, epithelium 12 is disposed across cornea 10 and is a protective layer. Epithelium 12 covers nerves of the cornea and minimizes the flow of water from the tear film of the eye to into the stroma. Epithelium 12 in most human patients can be about 40 to 60 microns thick, for example about 50 microns. When epithelium 12 is intact, endothelium 18 can pump water from stroma 16 and maintain hydration in the cornea at a proper level. The mechanism by which the stroma of the cornea remains properly hydrated can be referred to as deturgescence. Deturgescence of the cornea can be important because excess hydration of the cornea can result in swelling of the cornea and light scattering, or haze, that can degrade vision. The total thickness of normal cornea 10 from endothelium 18 to tear liquid in most human patients can be from about 400 to 600 microns. A healthy cornea with normal hydration comprises about 80 to 85% water. Edema of the cornea due to swelling of the cornea, for example with additional water, can increase the thickness of the cornea.

With refractive surgery, for example PRK, the epithelium can be removed to ablate a refractive correction into Bowman's membrane 14 and/or stroma 16. An initial profile of the anterior surface of stroma and/or Bowman's membrane is ablated to an ablated profile 20 to correct the patient's vision. The profile of tissue removed to correct vision is described in U.S. Pat. No. 5,163,934, entitled "Photorefractive keratectomy", the disclosure of which may be suitable for combination in accordance with some embodiments of the present invention described herein. Ablated profile 20 generally comprises an optical zone that extends across the cornea to correct refractive error of the eye and may correct aberrations of the eye, for example wavefront aberrations. Ablated profile 20 is bounded by boundary 20B that may circumscribe the ablated profile. The ablation profile 20 comprises a maximum dimension across, for example a diameter 20D.

The epithelium may comprise an inner boundary that moves centripetally inward as indicated by arrows 30

Figures 1, 1B:
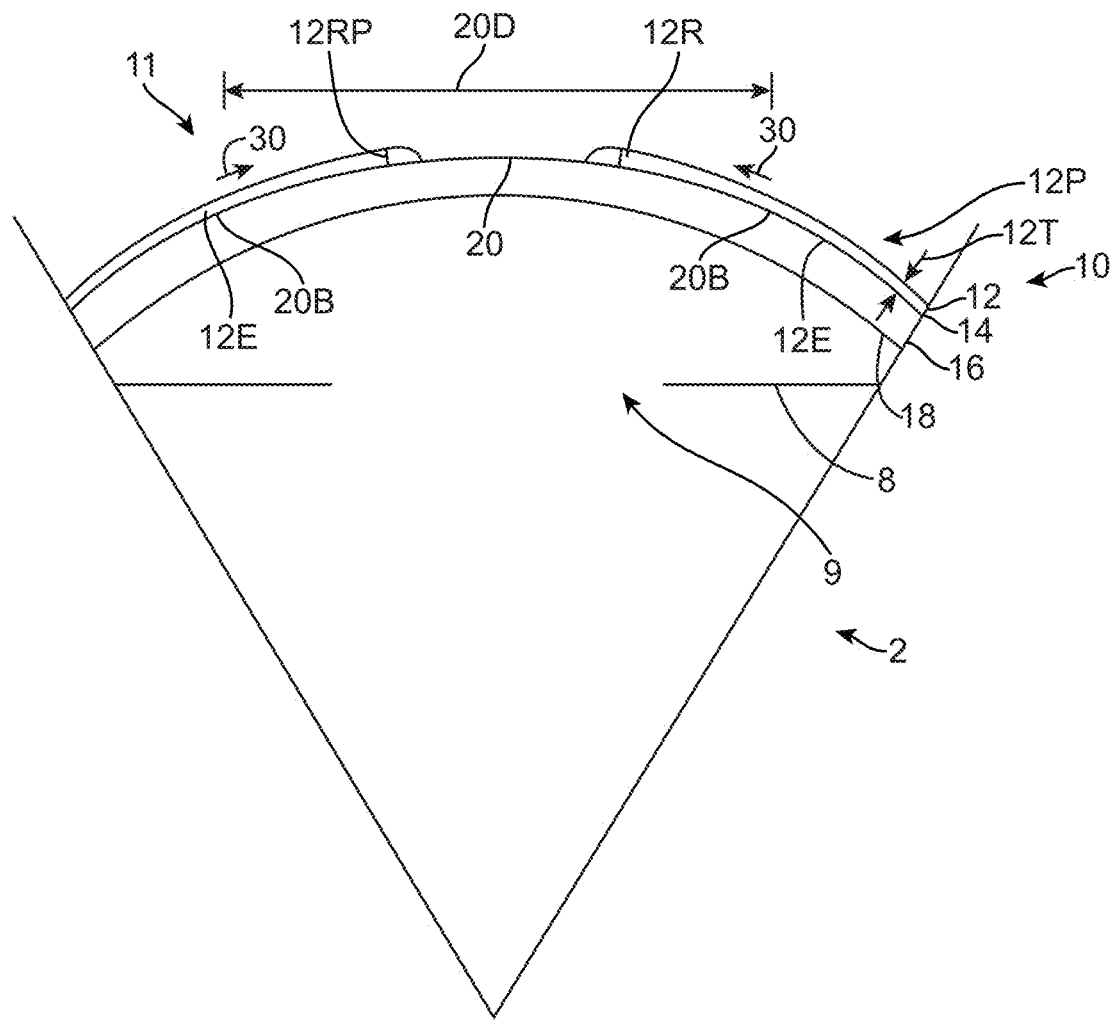

FIG. 1-1B shows an ablated eye about 1 to 2 days following refractive surgery resulting in an epithelial defect. The epithelium has at least partially covered the ablation. The epithelium may comprise irregularities and an inner boundary that moves centripetally inward as indicated by arrows 30. The thickness profile 12RP of the regenerating epithelium 12R can be irregular and degrade vision. The inner portion of the epithelium near the boundary may comprise a height greater than an outer portion of the epithelium away from the boundary of the epithelium. The portion of the ablation not covered with the epithelium and the inner portion of the epithelium near the boundary can result in aberrations, for example aberrations corresponding to a meniscus of the tear and a far sighted portion of the cornea. As variation in epithelial healing among individuals can be observed, the epithelial defect of at least some individuals can be present at 2 and 3 days post-op, with corresponding aberrations.

Figures 1, 1C:
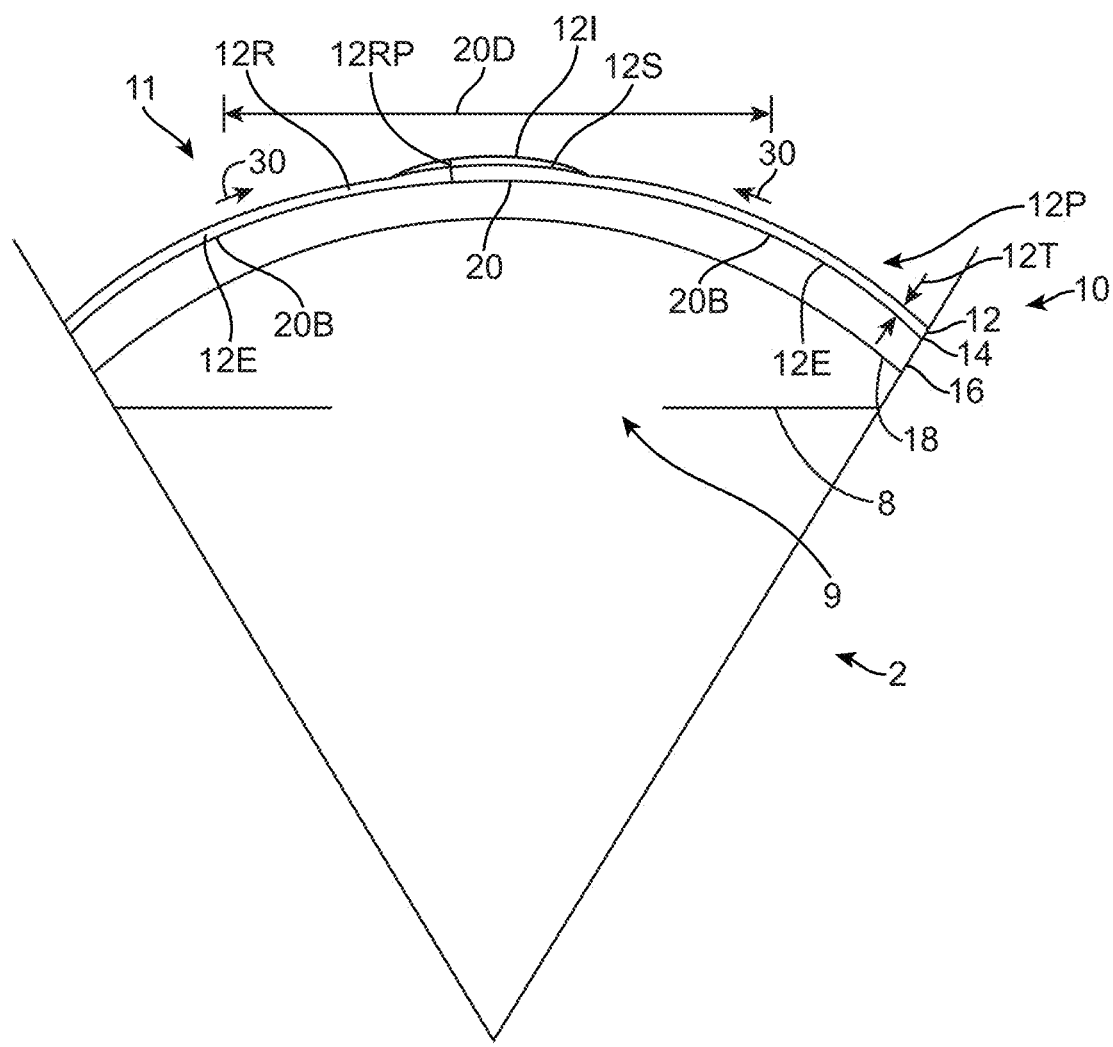

FIG. 1-1C shows an ablated eye when the epithelium has regenerated following refractive surgery resulting in an increased epithelial thickness centrally when the epithelium has regenerated, for example at about 3 days post-op. The regenerating epithelium may have an irregularity 12I, for example corresponding to an increased elevation of an inner portion of the epithelium near the center of the ablation, for example. Work in relation to embodiments as described herein suggests that the natural regeneration of the epithelium can provide an inner portion having an increased central elevation with optical power that may correspond to about 1 to 3 Diopters of additional optical power. The regenerating epithelium comprises a thickness profile 12RP extending along the surface of Bowman's membrane 14 and the ablation 20. With PRK the thickness profile 12RP of the epithelium can regenerate for at least one week, for example one month, such that vision can be degraded when the thickness profile 12RP of the epithelium regenerates, and PRK surgery of the cornea can be combined in accordance with embodiments described herein so as to improve vision.

In many embodiments as described herein, irregularities of the cornea are decreased when the epithelium regenerates so as to provide one or more of improved vision or comfort. The coverings as described herein can be configured so as to decrease an effect on vision of corneal irregularity 12I, decrease the height profile of irregularity 12I, decrease transfer of irregularity 12I to an anterior surface of the covering, smooth irregularity 12I with the covering, regenerate epithelium 12 such that irregularity 12I is decreased, or combinations thereof. In many embodiments, the covering 100 as described herein can be placed on the eye such that a smooth layer 12S of regenerated epithelium 12R substantially covers the ablated profile so as to provide improved vision sooner than would occur without covering, for example at about 3 to 4 days post-op with PRK. In many embodiments, the covering can provide an environment 100E as described herein so as to guide epithelial regeneration and smooth the regenerated epithelium.

In many embodiments, the cornea 10 of an eye 2 has an epithelial defect 11 following refractive surgery such as PRK, and a covering 100 positioned over the epithelial defect 11.

Figures 1, 2, 2A:
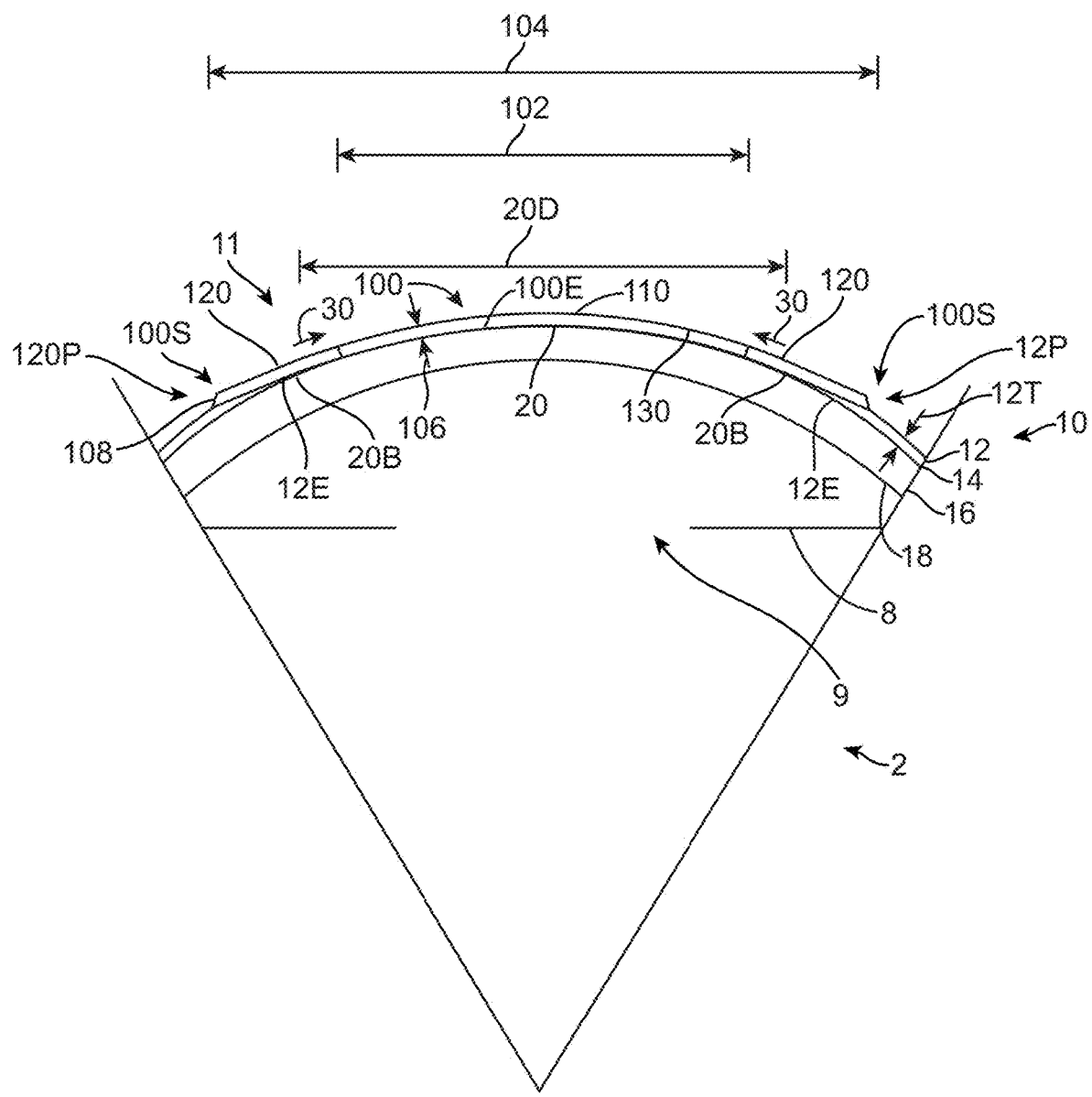

FIG. 1-2A shows a covering 100 positioned on cornea 10 an eye 2 having an epithelial defect 11, in which the covering abuts the cornea to seal the cornea. The covering may comprise a curved body, for example a curved contact lens body shaped to fit the cornea.

The covering 100 can be sized to cover the ablated profile and epithelial defect. The inner portion 110 comprises a dimension across 102 that can be sized to extend across a majority of the ablation, and the outer portion 120 comprises a dimension across 104 sized to extend across at least the epithelial defect and contact the epithelium on opposite sides of the defect.

The dimension 102 extending across a majority of the ablation may extend about 6 to 8 mm, for example, and may be sized larger than the ablation. The dimension 104 may comprise about 12 to 14 mm across, for example so as to extend to the limbus and can be sized to the limbus of the patient for example. Work in relation to embodiments suggests that the covering sized to extend to the limbus and circumferentially around the limbus can be centered on the cornea. The covering may extend such that the outer rim of the covering contacts the conjunctiva disposed above the sclera peripheral to the limbus, for example, and that such configurations may center the lens on the cornea, for example.

The thickness of the covering can be sized and shaped in many ways. The inner portion 110 of the covering comprises a thickness 106 and the outer portion 120 of the covering comprises a thickness 108. The thickness 106 of the inner portion may comprise a substantially uniform thickness such that the inner portion comprises an optical power of no more than about +/−1D prior to placement on the eye, for example when held in front of the eye and separated from the cornea by a distance. Alternatively, the thickness of the inner portion may vary so as comprise optical power, for example optical power to correct vision of the patient.

Figures 1, 2, 2B:
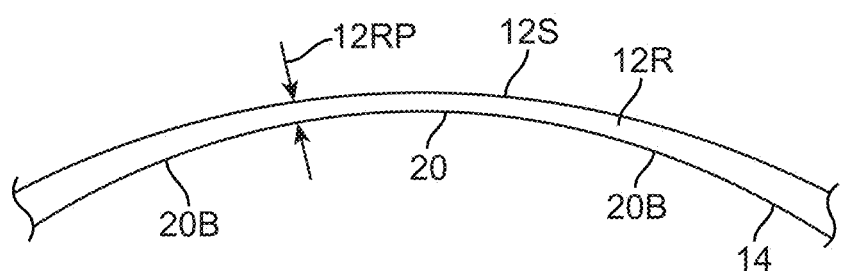
Figure 1A:
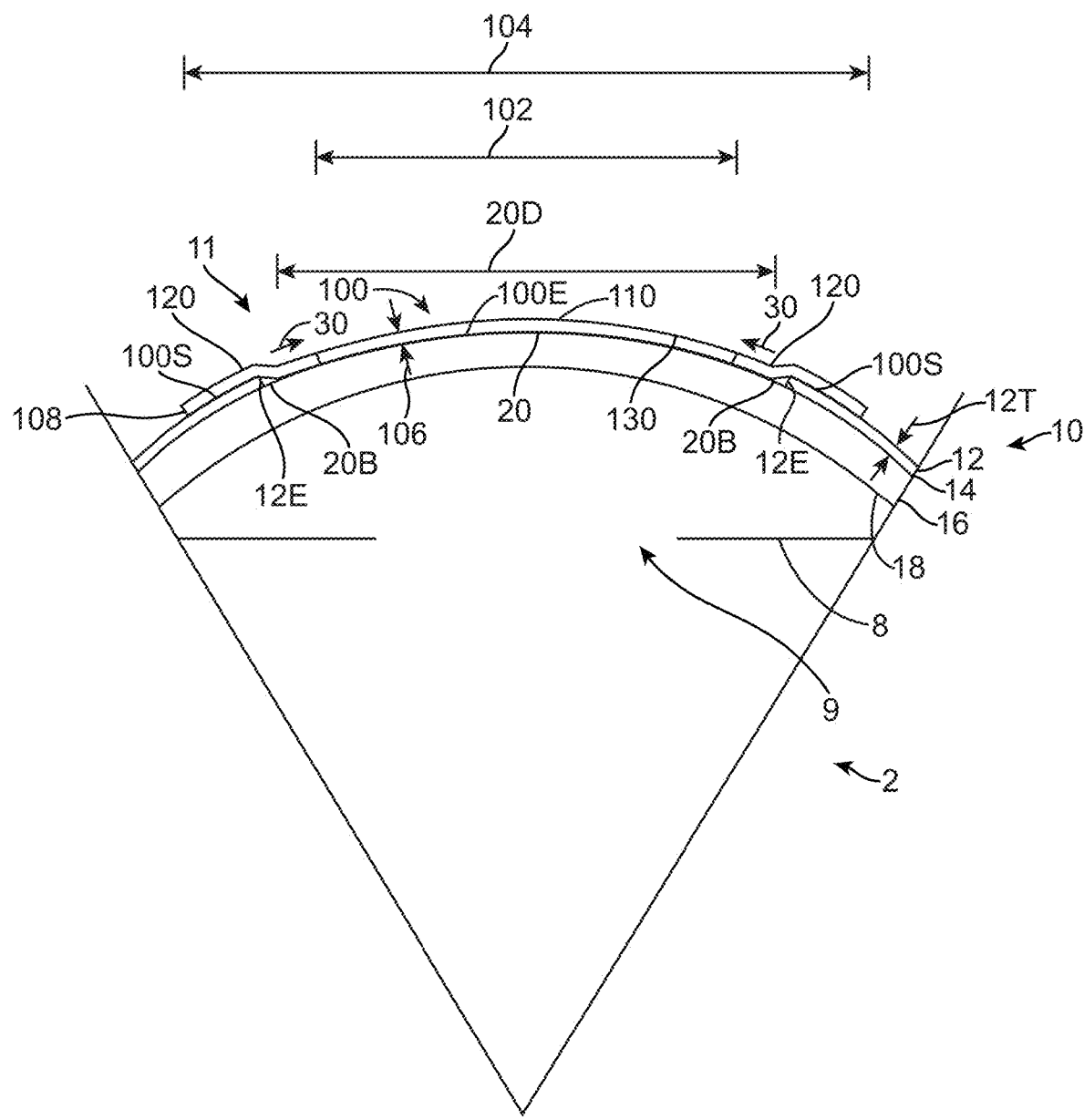

FIG. 1-2B shows a smooth layer 12S of regenerated epithelium 12R substantially covering an ablated profile. The environment 100E is configured to guide epithelial regeneration and smooth the regenerated epithelium. The regenerating epithelium comprises a thickness profile 12RP.

The epithelium grows centripetally from circumscribing boundary 12E toward the center of ablated profile 20 to cover the exposed stroma, as indicated by arrows 30.

The covering 100 may comprise an inner portion 110 and an outer portion 120. The outer portion 110 can be configured to form a seal 100S with the cornea near the edge of the ablation and the epithelial defect, for example with a soft conformable material such as silicone or silicone hydrogel. The inner portion 120 is positioned over the pupil and configured for the patient to see, and may comprise a rigidity greater than the outer portion, so as to smooth irregularities of the epithelium when the cornea heals. Alternatively, the inner portion may comprise a rigidity equal to or less than the rigidity of the outer portion as well. For example, the inner portion may comprise silicone and the outer portion may comprise silicone, and the inner portion may comprise one or more of a more rigid silicone or a greater thickness such that the inner portion can be more rigid than the outer portion so as to smooth the epithelium. Although the inner portion can be more rigid than the outer portion, the inner portion is sufficiently soft, flexible and conformable so as to conform at least partially to the ablated profile 20 in the stroma, such that the patient receives the benefit of the vision correction with the ablation profile 20 when the patient looks through the inner portion and the inner portion smoothes the epithelium. Work in relation to embodiments of the present invention suggests that the regenerating epithelium is softer than the underlying stroma of ablation profile 20, such that the inner portion can be configured to conform to the shape of the ablation profile 20 when the inner portion smoothes the epithelium disposed under the inner portion.

The covering 100 may comprise one or more of many optically clear materials, for example synthetic materials or natural material such collagen based materials, and combinations thereof, such as described in U.S. patent application Ser. No. 12/384,659, filed Apr. 6, 2009, entitled "Therapeutic Device for Pain Management and Vision", U.S. Pub. No. US 2010-0036488 A1, published on 11 Feb. 2010. For example, the lens material may comprise a naturally occurring material, such as collagen based material. Alternatively or in combination, the lens material may comprise a known synthetic material, for example hydroxyethyl methacrylate (HEMA) hydrogel, hydrogel, silicone, for example hydrated silicone and derivatives thereof. For example the optically clear material may comprise one or more of silicone, silicone hydrogel, silicone comprising resin, silicone comprising silicate, acrylate, collagen. The cured silicone may comprise silicone that is two-part heat cured and RTV (room temperature vulcanized). For example, polydimethyl siloxane such as NuSil, or poly(dimethyl) (diphenyl) siloxane may be used to mold the covering, for example with less than 10% water content so as to increase oxygen diffusion through the covering. The covering 100 may comprise perfluoropolyethers or fluorofocal. The lens material can be elastic, for example a stretchable elastic material such as silicone, such that the lens can seal the cornea. The lens material can be cured with a hardness and size and shape such that the covering comprises a modulus within a range from about 4 to about 20 MPa. The material may comprise, for example, silicone elastomer having optically clear silicate disposed therein and a water content of no more than about 10%, for example no more than about 5%, such that the lens covering has a very high Dk exceeding 150, and the silicone lens comprising silicate can be treated to provide a wettable surface. The lens may comprise hydrogel, for example silicone hydrogel, and can be formed with a water content within a range from about 5% to about 35% and a modulus within a range from about 4 to about 20 MPa, such that the covering conforms at least partially to the ablated stroma.

The covering may comprise silicone or silicone hydrogel having a low ionoporosity such that covering seals to the cornea. For example, covering may comprise silicone hydrogel comprising a low ion permeability, and the range of water can be from about 5% to about 35%, such that the Dk is 100 or more. The low ion permeability may comprise an Ionoton Ion Permeability Coefficient of no more than about $0.25 \times 10^{-3}$ cm2/sec so as to seal the cornea, for example no more than about $0.08 \times 10^{-3}$ cm2/sec. The low ion permeability comprises an Ionoton Ion Permeability Coefficient of no more than about $2.6 \times 10^{-6}$ mm2/min to seal the cornea, for example no more than about $1.5 \times 10^{-6}$ mm2/min.

The covering 100 may comprise a wettable surface coating 130 disposed on at least the upper side of the covering, such that the tear film of the patient is smooth over the covering and the patient can see. The wettable surface coating may comprise a lubricious coating for patient comfort, for example to lubricate the eye when the patient blinks. The wettable coating may comprise a contact angle no more than about 80 degrees. For example the coating may comprise a contact angle no more than about 70 degrees, and the contact angle can be within a range from about 55 to 65 degrees to provide a surface with a smooth tear layer for vision. For example, the wettable coating can be disposed both an upper surface and a lower surface of the covering. Alternatively, the lower surface may comprise a hydrophobic surface material and the lower hydrophobic surface may comprise the inner portion 110 and the outer portion 120. At least the outer portion 120 may comprises a lower surface composed of a sticky, tacky, material, for example a hydrophobic material. The inner portion may also comprise the lower surface comprised of the sticky, tacky, hydrophobic material. The upper surface may comprise the wettable coating extending over at least the inner portion 110.

The wettable coating may comprise one or more of many materials. For example, the wettable coating may comprise polyethylene glycol (PEG), and the PEG coating can be disposed on Parylene™. Alternatively, the wettable coating may comprise a plasma coating, and the plasma coating comprise a luminous chemical vapor deposition (LCVD) film. For example, the plasma coating comprises at least one of a hydrocarbon, for example CH4, O2 or fluorine containing hydrocarbon, for example CF4 coating. Alternatively or in combination, the wettable coating may comprise a polyethylene glycol (PEG) coating or 2-hydroxyethylmethacrylate (HEMA). For example, the wettable coating may comprise HEMA disposed on a Parylene™ coating, or the wettable coating may comprise N-vinylpyrrolidone (NVP) disposed on a Parylene™ coating.

The covering 100 may comprise a lower surface corresponding to one or more of many suitable shapes to fit the covering to the cornea. For example, the lower surface of the covering may correspond to base radius of curvature. With post ablation corneas, the covering can conform substantially to the cornea. The covering may comprise a second curve in combination with a first curve, such that the lower surface comprises a bicurve surface. Alternatively, the lower surface may correspond to an aspheric surface. For example an aspheric surface may comprise an oblate shape and conic constant to fit a post PRK eye. Also, it may be helpful to fit the covering to the cornea, for example with selection of one covering from a plurality of sizes.

FIG. 1A shows the covering 100 having the thickness 108 of the outer portion sized such that the outer portion can conform to the epithelium. The thickness of the outer portion can be substantially constant, or may vary as described herein below.

FIG. 1A1 shows covering 100 positioned on an eye and blinking of the eye. An upper lid and a lower lid can blink over the eye. Work in relation to embodiments suggests that the upper lid can exert a downward movement 20 and that the lower lid can exert an upper movement 22 on the eye. The downward movement 20 can be greater than the upper movement 22. The wettable coating material as described herein can decrease force and movement transferred from the lids to the covering so as to inhibit motion of the covering. The downward movement 20 greater than the upward movement 22 can effect epithelial growth near the perimeter of covering 100.

FIG. 1B1 shows covering 100 as in FIG. 1-2A prior to placement on the cornea. The covering 100 may comprise a base radius R1 of curvature, and the base radius of curvature may be slightly shorter than the ablated cornea such that the covering can be steeper than the cornea prior to placement on the cornea. The covering 100 comprises a first configuration 100C1 prior to placement on the cornea.

The base radius R1 can be sized to the cornea in many ways. For example base radius R1 may have a radius corresponding to the outer unablated portion of the cornea. Alternatively or in combination, the base radius R1 may have a radius corresponding to the post ablated eye.

The covering 100 may comprise a modulus within a range from about 4 MPa to about 20 MPa, such that central portion can conform at least partially to the ablated stroma and so that the covering can smooth corneal irregularities and stromal irregularities of the ablated cornea. The covering may comprise an elastomeric stretchable material such that the covering can stretch to fit the cornea, for example. The covering having the modulus within a range from about 4 MPa to about 20 MPa can be formed in many ways as described herein. For example, the covering may comprise a single piece of material having a substantially uniform thickness extending across the ablated cornea and at least a portion of the unablated cornea, and the single piece of material may comprise an elastic material such as a silicone elastomer or a hydrogel. Alternatively, the covering may comprise a single piece of material having a non-uniform thickness extending across the ablated cornea and at least a portion of the unablated cornea. The covering can be shaped in many ways and may comprise a single piece of one material, or may comprise a single piece composed to two similar materials, or may comprise a plurality of materials joined together.

The covering 100 may comprise one or more outer portions extending outside the inner central, and these outer portions may seal the cornea when the inner portion conforms at least partially to the ablated stroma. For example, the covering 100 may comprise outer portion additional shapes disposed outward from a central portion as described herein. For example, the covering may comprise a bicurve having a second radius of curvature disposed peripheral to the inner radius R1 of curvature to fit the unablated portion of the cornea. For example, the second and outer radius of curvature may comprise a shorter radius of curvature when the central portion is treated for myopia. The covering may comprise a third radius of curvature longer than the second radius of curvature so as to fit the sclera under the conjunctiva. The covering may comprise an oblate shape to fit the ablated and non-ablated portions of the cornea, and the covering may extend over the sclera with an outer portion, for example.

FIG. 1B2 shows the covering as in FIG. 1B1 conforming to ablated stromal tissue and smoothing the epithelium over the ablated stroma. The cornea comprises an ablated surface 20 to correct vision that may have a corresponding radius of curvature, for example radius R2. The ablated profile 20 may comprise additional, alternative, or combinational shapes with those corresponding to radius R2, such as aberrations ablated into the cornea to correct aberrations of the eye and astigmatism ablated into the cornea, and the inner portion 110 of covering 100 can conform to these ablated profiles of the cornea such that the patient can receive the benefit of the ablative vision correction when the covering is positioned on the cornea. For example, the cornea ablation profile 20 may correspond to radius of curvature R2, and the inner portion 110 can flatten from configuration 100C1 corresponding to radius of curvature R1 prior to placement to a second configuration 100C2 corresponding substantially to the ablated profile 20, such the patient can see with the benefit of ablation profile 20. For example, the second configuration 100C2 can comprise a conforming radius of curvature R12 that corresponds substantially to radius of curvature R2. The profile corresponding to the first configuration 100C1 of the covering 100 is shown positioned over cornea 10 to illustrate the change in profile of the covering from configuration 100C1 prior to placement to conforming configuration 100C2 of the covering 100 when positioned on the cornea.

The conformable covering 100 comprises sufficient rigidity so as to smooth the epithelium when covering 100 is positioned on the cornea over the ablation profile 20. The epithelium comprises a peripheral thickness 12T that may correspond substantially to a thickness of the epithelium prior to debridement of the epithelium to ablate the cornea. The epithelium also comprises regenerating epithelium 12R disposed over the ablation profile 20. The covering 100 can smooth the epithelium 12R when conforming to the cornea in the second configuration 12C2. For example, irregularities 12I of the regenerating epithelium 12R disposed over the ablation can be smoothed when the epithelium regenerates along the inner portion of covering 100, such that the irregularities 12I of the regenerating epithelium 12R are thinner than the thickness 12T of the peripheral epithelium.

Work in relation to the embodiments as described herein indicates that an at least partially conformable covering having a modulus within a range from about 4 MPa to about 20 MPa can conform at least partially to the ablated stroma and smooth irregularities of the epithelium and stroma so as to improve vision as described herein. The covering having the modulus within the range from about 4 MPa to about 20 MPa can be formed in many ways as described herein.

The conformable covering 100 may comprise a perimeter 120P with a rigidity sufficient to indent the epithelium along at least a portion of the perimeter so as to seal the cornea with seal 100S. The portion 12C of the epithelium 12 can extend over the perimeter of the covering 120P.

FIG. 1B2A shows a covering as in FIG. 1B2 forming an indentation 12I in the epithelium such that the epithelium 12 extends over at least a portion of the perimeter 120P of the covering. The covering forms indentation 12I in the epithelium such that the epithelium comprises an indentation thickness 121T that is less than an outer thickness of the epithelium 12T. The indentation of the epithelium with the covering can help to seal the cornea with the perimeter.

FIG. 1B2B shows a covering as in FIG. 1B2 forming indentation 12 in the epithelium. The covering forms indentation 12I in the epithelium such that the epithelium comprises an indentation thickness 121T that is less than an outer thickness of the epithelium 12T. The indentation of the epithelium with the covering can help to seal the cornea with the perimeter.

Work in relation to embodiments described herein suggests the indentation of the covering can vary radially around the eye of the patient, in accordance with orientation of the covering on the eye when the covering comprises a substantially constant rigidity of the outer portion, for example a substantially constant rigidity around the perimeter. The inferior portion of the covering may comprise a greater amount of epithelial covering over the perimeter than the superior portion of the covering. For example, FIG. 1B2A may correspond to a first portion of covering 100 at an inferior location of the cornea and FIG. 1B2B may correspond to a second portion of the covering at a superior location of the cornea. Work in relation to embodiments also suggests that there may be variability in covering of the perimeter with the epithelium between the nasal portion of the perimeter, and the temporal portion of the perimeter, although both the nasal and temporal locations can comprise covering intermediate and between the more extensive covering of the inferior portion and the less extensive covering of the superior portion of the perimeter.

FIG. 1B2C shows a covering abutting the cornea to seal the cornea without forming a substantial indentation in the epithelium. The covering may comprise a chamfer to contact and seal the cornea. The rigidity of the outer portion can be determined based on the thickness of the outer portion of the covering, hardness of the material, and chamfer angle so as to contact the epithelium to seal the cornea without substantial deformation of the epithelium.

The covering may comprise a non-uniform rigidity around the outer portion of the covering comprising the perimeter. For example, the covering may comprise a superior portion corresponding to a superior location on the cornea and an inferior portion corresponding to an inferior location on the cornea. The superior portion may comprise a rigidity less than the inferior portion. For example, the superior portion may comprise the rigidity less than the inferior portion, such that deformation of the epithelium is inhibited when the perimeter abuts the cornea is sealed. Alternatively, the superior portion may comprise the rigidity less than the inferior portion such the deformation of the epithelium with the covering comprises a substantially constant amount around the perimeter, for example a deformation of no more than about 10 um, for example 5 um.

FIG. 1C shows a therapeutic covering as in FIG. 1-2A comprising a covering molded with a homogeneous material, in which the outer portion comprises a thickness configured to conform with the cornea and in which the inner portion 110 comprises thickness configured to smooth the epithelium and conform to the ablated profile 20. The outer portion 120 may comprise a thickness of no more than about 100 microns. For example the outer portion 120 may comprise a thickness of about 50 microns at the boundary with the inner portion 110, and linearly taper from 50 microns at the boundary with the inner portion to about 20 microns at the periphery of the outer portion 120. The inner portion 110 may comprise a thickness of no more than about 250 microns, for example no more than about 200 microns. For example, the inner portion may comprise a thickness of about 100 microns. For example, the thickness of each of the inner portion and the outer portion may comprise no more than about 50 microns so as to provide substantial oxygen transport and epithelial regeneration. Many materials can be used as described herein, and the covering may comprise one or more materials. For example, the covering may comprise a single piece of material such as silicone having a water content within a range from about 0.1% to about 10%, for example no more than about 1%, and a hardness Shore A durometer parameter within a range from about 5 to about 90, for example within a range from about 40 to about 85.

FIG. 1C1 shows a covering 100 having an inner portion 110 comprising an inner thickness and an inner material 110M and an outer portion 120 comprising an outer thickness and an outer material 120M, in which the inner thickness is greater than the outer thickness. The inner material 110M may comprise many materials and may comprise an optically clear silicone, for example silicone with resin. The inner material may comprise silicone positioned in a mold with the outer portion 120 formed around the inner portion. The inner portion may comprise a hardness similar to the outer portion. The outer material 120M of the outer portion 120 may comprise a material similar to the inner portion. For example the outer material 120M may comprise silicone and the inner material 110M may comprise silicone. This use of similar materials on the inner and outer portion can improve adhesion of the inner portion to the outer portion. The outer material 120M may extend along the inner portion 110, for example along the underside of the inner portion 110, such that the inner material 110M is held in a pocket of the outer material 120M. Alternatively, the inner material 110M may extend substantially across the thickness of the inner portion 110, such that the outer material 120M comprises a substantially annular shape with the inner material 110M comprising a disc shaped portion disposed within the annulus and extending substantially from the upper surface coating to the lower surface coating when present.

FIG. 1C1A shows a covering as in FIG. 1C1 adhered to the cornea with a smooth upper surface, and a lower surface conforming to irregularity of the cornea, for example an irregularity comprising a central island CI of the ablated stroma. The central island CI may comprise an outward protrusion in the ablated profile of the stroma at least about 1 micron outward and about 2.5 mm across, for example. The upper surface may comprise a substantially rigid material for vision correction, and the lower surface may comprise a soft material so as to deflect to irregularities of the cornea when the upper surface provides optical correction. For example the lower surface may comprise an indentation 110I when positioned on the irregularity of the cornea. Although the lower surface comprising the soft material can deflect to correspond to the ablation profile 20, the upper surface comprising the rigid material may comprise a predetermined curvature selected by a health care provider so as to fit the ablation profile and correspond to the refractive correction of the patient so as to provide vision correction.

FIG. 1C2 shows a covering as in FIGS. 1-2A to 1B2 having inner portion 110 comprising an inner thickness and inner material 110M and outer portion 120 comprising an outer thickness and outer material 120M, in which the inner thickness can be greater than the outer thickness and the outer material 120M extends around the inner material 110M. The covering 100 may comprise at least a bicurve covering having at least a second radius R1B. The inner portion 110M may comprise three layers of material, a first layer 110L1 of a first material 110M1, a second layer 110L2 of a second material 110M2 and a third layer 110L3 of a third material 110M3. The second material 110M2 may comprise a rigid material, for example one or more of a rigid gas permeable material, a rigid silicone, or a rigid silicon acrylate. The first material 110M1 and the third material 110M3 may comprise a soft material, for example a soft elastomer or soft hydrogel such as one or more of a soft optically clear silicone or a soft silicone hydrogel. The first material, the third material, and the outer material 120M may comprise similar materials, such that the second layer of rigid material 110M2 is encapsulated with the first soft material 110M1, the third soft material 110M3 and on the perimeter with the soft outer material 120M. In many embodiments, the second rigid material 110M2 comprises a material similar to each of the first material 110M1, the third material 110M3 and the outer material 120M, for example each may comprise silicone, such that the corresponding portions of the covering 100 can be bonded together with the silicone similar silicone elastomer material, for example. In many embodiments, the covering 100 can be formed in a mold with rigid second material 110M2 placed in the mold and encapsulated within a single piece of material comprising first material 110M1, third material 110M3 and outer material 120M, such that first material 110M1, third material 110M3 and outer material 120M comprise substantially the same material, for example silicone elastomer. The rigid second material 110M2 may comprise silicone bonded to each of first material 110M1, third material 110M3 and the outer material 120M, for example with curing such that first material 110M1, third material 110M3 and outer material 120M comprise the same soft silicone material bonded to the second material 110M2 comprising rigid silicone.

The soft material comprising soft outer portion 120 composed of soft material 120M, first layer 110L1 composed of soft material 110M1 and third layer 110L3 composed of soft material 120M3 can provide improved comfort and healing for the patient. The soft material can deflect, bend or indent so as to conform at least partially to the tissue of the eye when the rigid portion comprising rigid material 110M2 corrects vision of the patient. The dimension 102 across inner portion 110 can be sized to substantially cover the ablation zone and slightly smaller than the ablation dimensions, such as ablation diameter 20D, so that the epithelium can grow inward and contact the layer 110L1 of soft first material 110M1 without substantial disruption from the rigid material 120M2 when the inner portion 110M corrects vision with the layer of rigid material 110M2. The eyelid can also move over the third layer 110M3 for improved comfort. The soft first material 110M1 and soft third material 110M3 may comprise soft elastomer or soft hydrogel, for example, and may each comprise the same material so as to encapsulate the second layer 110L2 of rigid second material 110M2.

The soft material comprising soft outer portion 120 composed of soft material 120M, first layer 110L1 composed of soft material 110M1 and third layer 110L3 composed of soft material 120M3 can have a modulus within a range from about 1 to 20 MPa, for example within a range from about 1 to 5 MPa.

The material inner material 120M and 120M2 of second layer 120L2 can have a modulus within a range from about 5 to about 35 or more, for example as set forth in Table A below. For example, when material 120M comprises silicone elastomer or layer 110L2 of material 120M2 comprises silicone elastomer, the modulus can be within a range from about 5 to about 35 MPa, for example within a range from about 20 to about 35 MPa.

The layers of covering 100 can comprise dimensions so as to provide therapeutic benefit when placed on eye 2. The thickness of layer 110L1 can be from about 5 um to about 50 um, for example, within a range from about 10-30 um, such that the layer 110L1 can provide a soft at least partially conformable material to receive the lens. The middle layer 110L2 can be from about 20 um to about 150 um, for example, and material M2 can have a modulus greater than first material 110M1 of first layer 110L1, so as to deflect the epithelium of the eye when the middle layer is deflected. The third layer 110L3 can be within a range from about 5 um to 50 um, for example within a range from about 10 um to about 30 um, and can cover second layer 110L2 so as to retain the second layer in the inner portion 110 of the covering 100.

FIG. 1C2A shows a covering as in FIG. 1C1 placed on the cornea with a smooth upper surface and a lower surface conforming to irregularity of the cornea near the edge of the ablation. As the epithelium can be about 50 um thick, in many embodiments the dimension 102 is sized so as to cover substantially the ablated cornea for vision correction and smaller than the ablation zone, such that the outer portion 120 can conform at least partially to the epithelium. The outer portion 120 may extend to the sclera, and comprise a tri-curve covering 100 as described herein, with the inner portion 110 having first layer 110L1 of first material 110M1, second layer 110L2 of second material 110M2, and third layer 110L3 of third material 110M3.

Figure 1D:
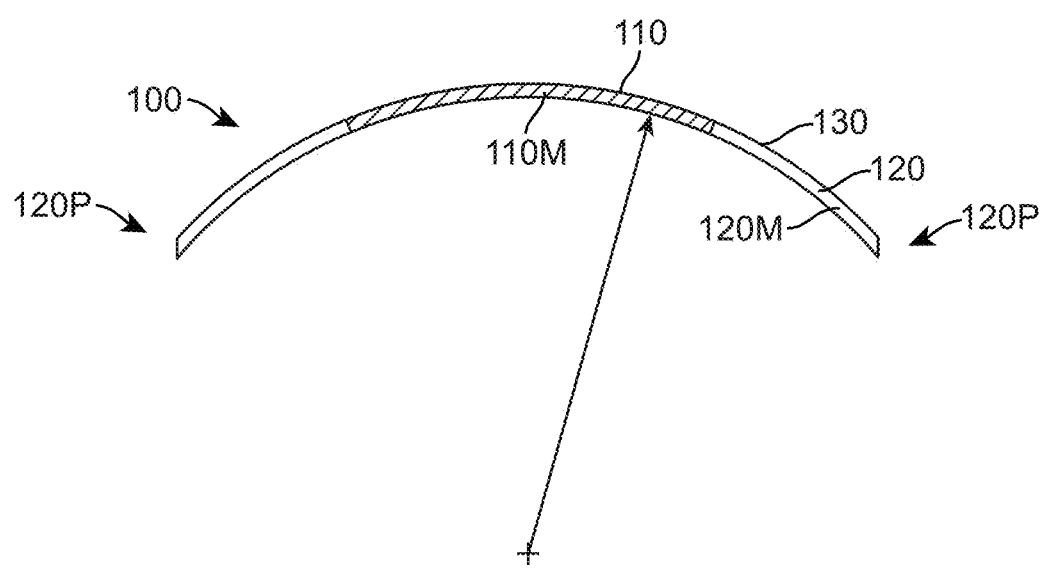
FIG. 1D shows a covering as in FIGS. 1-2A to 1B2 having an inner portion comprising an inner thickness and an inner material and an outer portion comprising an outer thickness and an outer material, in which the inner thickness is substantially similar to the outer thickness, in accordance with embodiments of the present invention.

FIG. 1D shows a therapeutic covering 100 comprising a first inner material 110M and a second outer material 120M, in which the outer portion 120 comprises a hardness configured to conform with epithelium of the cornea and in which the inner portion 110 comprises second hardness configured to smooth the epithelium and conform to the ablated profile 20. The outer material 120M may comprise many materials as herein. The Shore A hardness of each of the inner portion and the outer portion can be within a range from about 5 to about 90. For example, the outer material 120M may comprise silicone having a hardness Shore A durometer parameter from about 20 to about 50, for example from about 20 to about 40, and the inner material 110M may comprise silicone having a hardness durometer parameter from about 40 to about 90, for example from about 50 to about 90. The outer portion comprises a perimeter 120P, and the perimeter may comprise a peripheral and circumferential edge structure to abut the epithelium to form the seal with the epithelium, for example when the base radius of the covering is less than the cornea. The peripheral and circumferential edge structure can be shaped in many ways to define an edge extending around the perimeter to abut the epithelium, for example with one or more of a taper of the edge portion extending to the perimeter, a bevel of the edge portion extending to the perimeter or a chamfer of the edge portion extending to the perimeter. The inner portion 110 may comprise inner thickness and inner material 110M and the outer portion 120 may comprise an outer thickness and outer material 120M, in which the inner thickness is substantially similar to the outer thickness.

The peripheral edge structure to abut the epithelium can be used with many configurations of the inner portion as described herein. For example, the inner portion may comprise an RGP lens material having a lower rigid surface to contact and smooth the cornea and an upper rigid optical surface. Alternatively, the inner portion may conform to the cornea as described herein. The outer portion may comprise a skirt, and the skirt may comprise the peripheral edge structure to abut and seal the cornea, such as the chamfer. The rigidity of the outer portion comprising the edge structure can be determined to seal the cornea with one or more of hardness and thickness, as described herein.

Figure 1E:
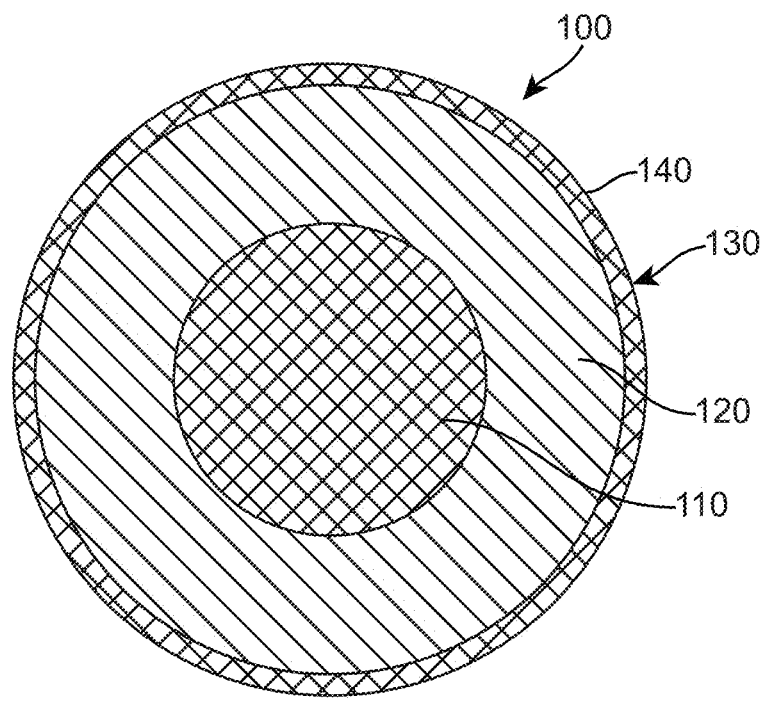
FIGS. 1E and 1F show top and side views, respectively, of a covering comprising an inner portion and an outer portion, as in FIGS. 1A to 1B2 and a peripheral rim portion disposed around the outer portion, in accordance with embodiments of the present invention.
Figure 1F:
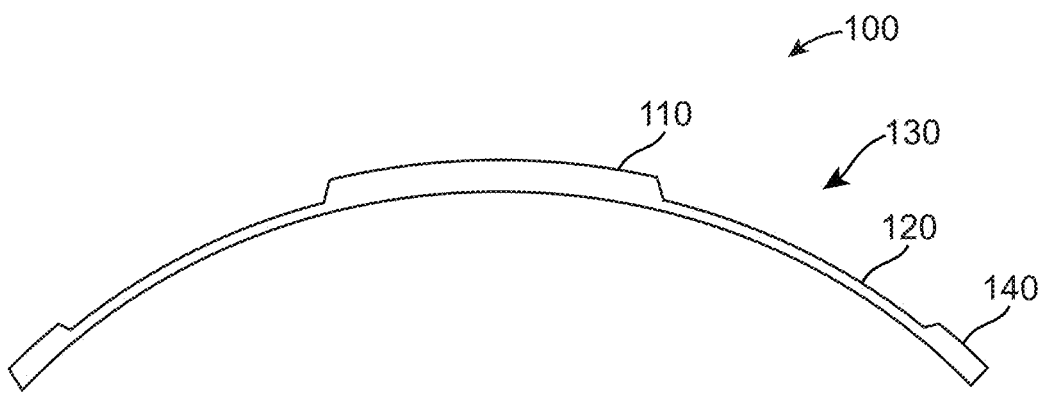

FIGS. 1E and 1F show top and side views, respectively, of covering 100 comprising inner portion 110, outer portion 120, and a peripheral rim portion 140 disposed around outer portion 120. The peripheral portion 140 can be more rigid than outer portion 120. Work in relation to embodiments suggests that in some instances the lower sticky tacky surface of outer portion 120 can stick to itself during deployment onto the eye, and the peripheral portion 140 can improve handling when the covering is placed on the eye. The covering may comprise a single piece of material or may comprise multiple pieces adhered together, for example molded together. For example, the covering may comprise an inner thickness of inner portion 110 and an outer thickness of outer portion 120, in which the inner thickness is greater than the outer thickness. The peripheral portion 140 may comprise a thickness, and the thickness of the peripheral portion 140 can be greater than the thickness of outer portion 120 such that the peripheral portion 140 is more rigid than the outer portion 120. The thickness of the inner portion 110 and the thickness of the peripheral portion 140 can be substantially similar, and these portions may comprise substantially the same thickness and rigidity.

FIG. 1G shows covering 100 comprising inner portion 110 and outer portion 120, such that outer portion 120 comprises a taper 120T of thickness 108 extending between the perimeter of the inner portion 110 and the perimeter of the outer portion 120. The taper may comprise a substantially linear change in thickness 108 extending between the perimeter of the inner portion and the perimeter of the outer portion.

FIG. 1G1 shows a covering 100 comprising inner portion 110 and an outer portion 120 comprising the taper as in FIG. 1G, and an outer rim or flange 120F of substantially uniform thickness peripheral to the taper 120T. The outer taper may extend from the dimension across 102 of the inner portion 110 to the dimension across 154A that is less than the dimension across 104 of the outer portion. The rim of substantially uniform thickness may comprise an annular shape having a thickness within a range from about 10 um thick to about 40 um thick, and may comprise a width 154B within a range from about 0.05 to about 0.8 mm, for example about 0.5 mm. The rim, for example flange 120F, may comprise a thickness of no more than about 50 um, such that the flange comprises a thickness no more than the epithelium.

The covering 100 can be dimensioned in many ways. The total diameter across can be from about 6 mm to about 12 mm, for example about 10 mm. The inner portion may comprise a diameter within a range from about 4 mm to 8 mm, for example about 6 mm. The annular rim comprising flange 120F can extend around the perimeter of the covering with a thickness of about within a range from about 5 um to about 50 um, for example about 35 um. The annular rim comprising flange 120F may comprise an inner diameter of within a range from about 5 mm to about 11 mm, for example about 9 mm and an outer diameter within a range from about 6 mm to about 12 mm, for example about 10 mm and corresponding to the perimeter of the covering. The annular rim may comprise a width of within a range from about 0.1 mm to about 1 mm, for example 0.5 mm, extending circumferentially around the covering. The outer portion 120 may comprise the rim with flange 120F and a taper 120T that extended from inner portion 110 to the rim comprising perimeter 120P. The taper in thickness can be substantially uniform between the outer diameter of the inner portion and the inner diameter of the rim, and the boundaries of the taper can be rounded and smoothed near the inner portion and the rim. The central portion may comprise a substantially uniform thickness within a range from about 50 um to about 150 um, for example 50 um. The base radius of curvature of the lower surface of the covering can be within a range from about was about 7 mm to about 8 mm. The lower surface may comprise an aspheric surface or a bicurve surface and combinations thereof. The upper surface of the covering can comprise a radius of curvature along the inner portion within about 0.1 mm curvature of the lower surface, such that the covering is substantially uniform with no substantial refractive power, for example refractive power within about +/−1D.

FIGS. 1G1A to 1G1H show a covering as in FIG. 1G1 and dimensions suitable for use in accordance with embodiments as described herein such as with experiments, clinical studies and patient treatment. FIG. 1G1A shows an isometric view of covering 100 having the inner portion 110, the outer portion 120, the taper 120T and rim comprising flange 120F. FIG. 1G1B shows a bottom view of covering 100. FIG. 1G1C shows a side view of the covering 100. FIG. 1G1D shows a top view of the covering 100. FIG. 1G1E shows a side cross sectional view of covering 100 along section D. FIG. 1G1F shows detail C of cross-section D-D, including the radius of curvature R1 of the lower surface of the inner portion 110, and the upper radius of curvature Rupper of the inner portion 110. The upper radius of curvature Rupper may correspond substantially to the lower radius of curvature R1 prior to placement on the eye, for example to within about +/−1 D of optical power, such that the inner portion 110 prior to placement may comprise no substantial optical power. Detail C shows a side cross sectional view of covering 100 of the inner portion. FIG. 1G1G shows detail B of cross-section D-D. Detail B shows a side cross sectional view of the rim comprising flange 120F. The flange 102F has a thickness 109. Flange 120F may comprise a taper extending along a width 102FW, for example from a first thickness 109A of about 35 um to second thickness 109B of about 25 um extending along width 120FW near the chamfer. Flange 120F comprises a chamfered edge 120FE to contact the cornea or conjunctiva along perimeter 120P of the covering.

FIG. 1H1 shows spatial frequency and elevation smoothing of an epithelial irregularity 12I transferred to a front surface 110U of covering 100 as in FIG. 1-2A. The regenerating epithelium 12R comprises an irregularity 12I. The covering 100 conforms substantially to the shape ablated in the stroma when positioned on the eye as noted above. The covering 100 comprises a rigidity so as to conform substantially to the ablation profile 20 over about at least about 3 to 4 mm of the ablated stroma such that the patient can see and receive optical correction with the ablated surface. The regenerating epithelium comprises a thickness profile 12RP that includes irregularity 12I. The conformable covering comprises a thickness profile of thickness 106 that encompasses a deformation thickness over the irregularity 106D. The thickness of the covering can vary over the epithelium to smooth the irregularity transmitted to the front surface of the covering so as to improve patient vision consistent with the ablation profile 20 when the covering conforms to the ablation profile 20. For example thickness 106D over the irregularity can be less than thickness 106 away from the irregularity. The irregularity may comprise an indentation and the covering may be thinner over the indentation. The silicone elastomer and hydrogel materials as described can be at least somewhat compressible so as to conform at least partially to the cornea and form an indentation so as to receive a portion of the cornea comprising one or more of epithelium or ablated stroma and decrease aberrations.

Experimental studies of OCT images and Pentacam™ images and topography images, noted below, indicate that the thickness of the inner portion of the covering 100 can vary so as to decrease optical aberrations along the upper surface when the covering is adhered to the cornea. This variation in thickness can be related to one or more of stretching of the covering over the irregularity or compression of the covering over the irregularity.

The irregularities of the epithelium generally comprise spatial frequencies that are greater than the spatial frequencies of the vision correcting portion of the ablation. The covering can provide spatial filtering of the frequencies of the underlying surface so as to inhibit relatively higher spatial frequencies of epithelial irregularities and pass relatively lower spatial frequencies corresponding to vision correction, such as lower spatial frequencies corresponding to sphere and cylinder. The spatial frequencies ablation profile 20 that are useful to correction vision can be lower than the spatial frequencies of the irregularities, and the spatial dimensions of the vision correction greater than the dimensions of the irregularities. For example, the spatial frequencies of the vision correction can correspond to periods of oscillation less than the periods of oscillation of the irregularities.

FIG. 1H2 shows spatial frequency and elevation smoothing of the epithelial irregularity with a plot of relative height relative for the upper surface of the covering and the upper surface of the irregularity. The irregularity of the regenerating epithelium 12R may comprise a profile height 12RPH and profile width 12RPW. The upper surface of the covering may comprise a profile 110UP. The irregularity of the upper surface corresponding comprises a width 110UPW and a height 110UPH. Height 110UPH is less than height 12RPH so as to correspond to smoothing of the irregularity. Width 110UPW is greater than width 12RPW so as to correspond to smoothing of the irregularity. Profile 110UP of the upper surface of the covering corresponds to lower frequencies than profile 12RP, such that the covering comprise a low pass spatial frequency filter. This can be seen with the Pentacam™ and topography data shown below in conjunction with OCT images showing that the covering and cornea conform without a substantially gap disposed therebetween. Alternatively or in combination, the covering can smooth the cornea when a gap is present, for example when a portion of the cornea is smoothed with contact to the covering and the gap provides an environment for the epithelium to grow smoothly over the ablation.

Based on the teachings described herein, a person of ordinary skill in the art can conduct studies to determine empirically the rigidity of the inner portion so as to pass substantially vision correction spatial frequencies of the ablation to the upper surface of the covering and inhibit spatial frequencies of the irregularities of the ablated stroma and epithelium, for example with Pentacam™ and topography studies as described in the experimental section.

Work in relation to the embodiments as described herein indicates that a covering comprising a modulus within a range from about 4 MPa to about 20 MPa can provide smoothing with low pass spatial frequency filtering as described with reference to FIGS. 1H1 and 1H2. The covering may comprise an elastically stretchable material, for example an elastomer or a hydrogel, such that the lens can conform at least partially to the ablated stroma and exert at least some pressure on the ablated stroma and epithelium when at least partially conformed so as to smooth irregularities of the epithelium and irregularities of the stroma. The covering can comprise a thickness and a hardness so as to provide the spatial frequency filtering to improve vision in post-PRK patients with the modulus within the range from about 4 MPa to about 20 MPa. For example the lens thickness can be increased to increase the modulus, decreased to decrease the modulus. The hardness of the material can be increased to increase the modulus and decreased to decrease the modulus. The modulus within the range from about 4 MPa to about 20 MPa can attenuate substantially higher spatial frequencies corresponding to irregularities of the epithelium and stroma so as to smooth the high spatial frequencies corresponding to the irregularities that can degrade vision, and can conform substantially to lower spatial frequencies that correspond to the vision correction so as to pass the lower spatial frequencies corresponding to vision correction so that the patient can experience an improvement in vision when the epithelium regenerates under the covering. For example, the high spatial frequencies may correspond to frequencies greater than about $1/6$ (0.17) cycles per mm, and the low spatial frequencies may correspond to frequencies less than about $1/6$ (0.17) cycles per mm. A person of ordinary skill in the art can determine the modulus and corresponding spatial frequencies to attenuate and pass, in accordance with the teachings as described herein. For example, the modulus of the covering can be measured with known methods and apparatus to measure the modulus of a contact lens, and measurements with Pentacam™ images as described herein can be used to determine the relationship of the modulus of the measured lens coverings to smooth of irregularities, conformation of the lens coverings to the ablation, and vision.

FIG. 1I1 shows an inhibition of transfer of a corneal irregularity to a front surface of a covering, for example one or more of a stromal irregularity or an epithelial irregularity. The front surface of the covering comprises an optical surface for vision without substantially transfer of the irregularity to the front surface of the covering.

FIG. 1I2 shows elevation smoothing of the epithelial irregularity with a plot of height relative to a reference sphere for the upper surface of the covering and the upper surface of the irregularity. The plot shows a substantially spherical front surface of the covering, such that the transfer of the irregularity to the front surface is inhibited.

FIG. 1I3 shows a thickness profile of the covering as in FIG. 1I2 so as to smooth irregularities transferred to the front surface of the covering. The thickness profile can vary in response to the underlying surface, for example with a decrease in thickness corresponding to an elevation in the surface profile of the cornea.

FIG. 1J1 shows covering 100 having a bicurve profile to fit an ablated cornea. The bicurve profile may comprise an inner portion having a lower surface comprising a radius of curvature R1 and an outer portion having an radius of curvature R1B. The inner portion may comprise a radius selected to fit approximately the post-ablated cornea, for example to within about +/−2D. The outer portion may comprise the radius of curvature R1B sized to correspond to the outer unablated cornea, for example to within about +/−2D. The covering may comprise an elastic material with a modulus within a range from about 4 MPa to about 20 MPa, such that the covering can conform at least partially to the cornea and smooth irregularities of the cornea as described herein. R1 can be longer than R1B, for example with PRK ablation to treat myopia. R1 can be shorter than R2, for example with PRK ablation to threat hyperopia.

FIG. 1J2 shows covering 100 having an oblate profile to fit an ablated cornea, for example a cornea ablated for myopia. The covering may comprise an apical radius of curvature corresponding to R1 near a center of the covering, and a peripheral radius of curvature, based on the conic constant of the oblate profile of the lower surface of covering 100. Alternatively, the lower covering 100 may comprise a prolate ellipsoid shape to fit a PRK ablation to treat hyperopia.

FIG. 1J3 shows covering 100 having a tricurve profile to fit sclera and an ablated cornea. The tricurve covering may comprise an inner portion with an inner lower surface having radius of curvature R1 and an outer portion comprising an outer lower surface having radius of curvature R1B, as described above. The covering may comprise a third portion 132 disposed outside the outer portion and having a third radius of curvature R1C sized to fit the sclera and contact the conjunctiva disposed over the sclera. Work in relation to embodiments suggests that coupling to the sclera may improve alignment of the lens on the cornea.

The covering 100 having the tricurve profile may comprise dimensions sized to fit the cornea and sclera of the eye 2. The covering 100 having the tricurve profile may comprise an inner portion 110 and an outer portion 120 as described herein. The outer portion 120 may comprise the third scleral portion 132S having curvature R1C shaped to fit the sclera of the eye, for example shaped so as to contact the conjunctiva of the eye such that the conjunctiva is located between the sclera and the scleral portion 132S. The inner portion 110 may comprise a dimension 102 and the outer portion 120 may comprise a dimension 104 as described herein. The covering 100 may comprise a sag height 105 extending between an upper location of the inner portion 110 and the outer boundary of outer portion 120 shaped to fit the cornea. The third portion 132 may comprise a dimension across 103.

The dimension 102, the dimension 104 and the dimension 103 can be sized to the eye based on measurements of the eye. The dimension 103 may correspond to an annular region of the sclera extending from the limbus to the outer boundary of the third portion across a distance within a range from about 1 to 4 mm, for example within a range from about 1.5 to 2 mm. The size of the limbus of the eye can be measured so as to correspond to dimension 104, for example, and can be within a range from about 11 to 13 mm. The ablation zone can corresponds to dimension 102, and dimension 102 corresponding to the rigid inner portion can be sized about 0.5 to about 2 mm less than the dimension across the ablation zone, such that the soft outer portion 120 contacts the eye near the edge of the ablation and the epithelial debridement.

The radius of curvature R1C of portion 132 can be determined so as to fit the eye, and can be within a range from about 12 mm+/−3 mm. The outer portion can be fit to within about +/−0.5 mm, for example to within about +/−0.25 mm.

The dimensions of the covering 100 can be determined in many ways, for example with topography measurements of the cornea and sclera. The corneal and scleral topography can be measured with many instruments, such as with the Orbscan™ topography system commercially available from Bausch and Lomb, and the Pentacam™ Scheimpflug camera system commercially available from Oculus. The ablation profile can be combined with the topography to determine the shape of the eye.

The dimensions of covering 100 can be sized to one or more of the cornea and sclera based on tolerances that may be determined clinically.

The outer portion 120 and the third portion 132 may comprise openings such as fenestrations as described herein, for example when the material comprises silicone.

The outer portion 120 and third portion 132 may comprise a hydrogel material, for example a silicone hydrogel material, and the inner portion 110 may comprise the rigid material 110M, for example second layer 110L2 and second material 110M2 between first layer 110L1 of first material 110M1 and third layer 110L3 of third material 110M3 as described herein.

As the tricurve covering may couple to the sclera so as to provide environment 100E to promote epithelial regeneration without substantially sealing the cornea, the outer portion 120 of the covering and the third portion 132 of the covering may comprise substantially water permeable material, for example when the inner portion 120 comprises the rigid material as described herein.

FIG. 1J4 shows covering 100 having a curved profile to fit sclera and an oblate profile to fit ablated cornea. The covering comprises the inner portion having the lower surface with the oblate profile having radius of curvature R1 comprising an apical radius of curvature and radius of curvature RO, and an outer portion comprising a lower surface having radius R1C to couple to the sclera as described herein. The apical radius of curvature may comprise a first radius of curvature and the radius of curvature RO may comprise a second radius of curvature corresponding to a conic constant of the oblate profile.

The portions of the coverings as described herein, for example the inner portion and the outer portion, may comprise a junction wherein a first portion connects with a second portion, and the junction may have the modulus as described herein. The covering may comprise a contact lens having a central lens portion having a center stiffness of at least about 2 psi*mm2 coupled to an outer lenticular junction portion having a lenticular junction stiffness of at least about 5 psi*mm2.

FIG. 1J5 shows a covering 100 having the tricurve profile to fit sclera and the ablated cornea similar to FIG. 1J3. The modulus and thickness of the sclera contacting portion can be configured in many ways to fit may eyes with comfort and so as to resist movement of the inner portion 120. The modulus of sclera coupling portion 132 may be no more than about 5 MPa and the thickness no more than about 200 um so as to stretch substantially for comfort and resist movement of the inner portion when the placed on the sclera.

The dimension 103 of sclera contacting portion 132 may correspond to an annular region of the sclera extending from the limbus to the outer boundary of the third portion across a distance within a range from about 1 to 4 mm, such that the dimension 103 can be from about 12 mm to about 16 mm, for example from about 14 mm to about 16 mm.

The radius of curvature R1C, thickness and modulus of the portion 132 can be configured so as to fit the eye to resist movement of inner portion 120 and with comfort. The radius of curvature R1C can be sized less than the radius of curvature of the sclera and conjunctiva. For example, the radius of curvature R1C can be no more than about 10 mm, for example no more than about 9 mm when the curvature of the scleral portion of the eye is at least about 12 mm for example. The third relative rigidity may comprise no more than about 4E-5 Pa*m^3 so as to stretch substantially for comfort and resist movement of the inner portion when the outer portion is placed on the sclera.

The thickness of the third portion having radius of curvature R1C can vary, for example from a thickness of about 200 um to a tapered edge.

Figure 5A:
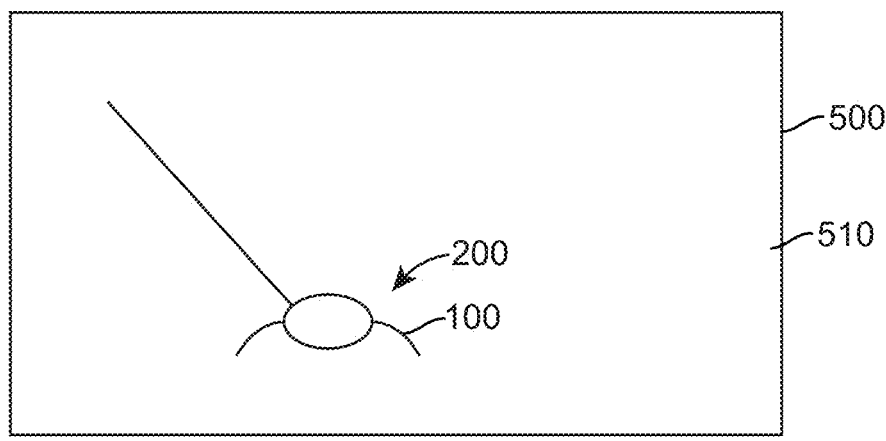
FIG. 5A shows an apparatus comprising a covering and applicator stored in a substantially dry, sterile compartment of a container, in accordance with embodiments of the present invention.
Figure 5B:
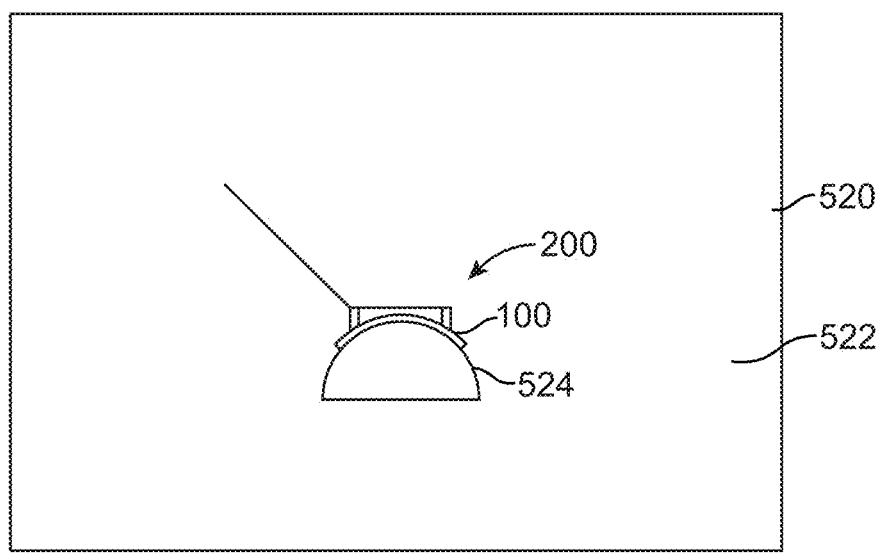
FIG. 5B shows an apparatus comprising a covering and applicator stored in a substantially moist, sterile compartment of a container, in accordance with embodiments of the present invention.
Figure 5D:
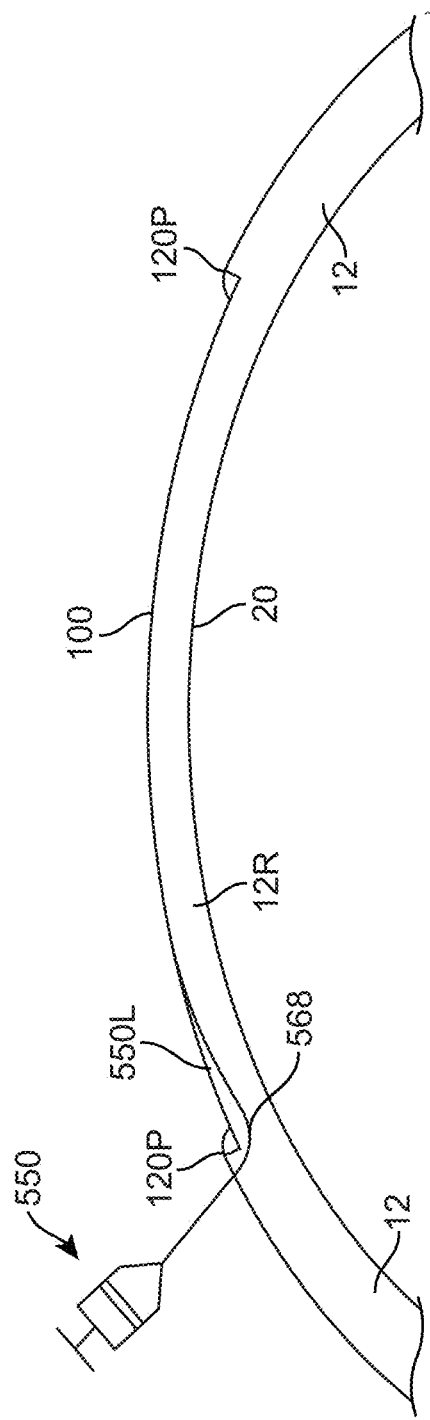
FIG. 5D shows a cannula of the apparatus as in FIG. 5C1 inserted under the covering.
Figure 6:
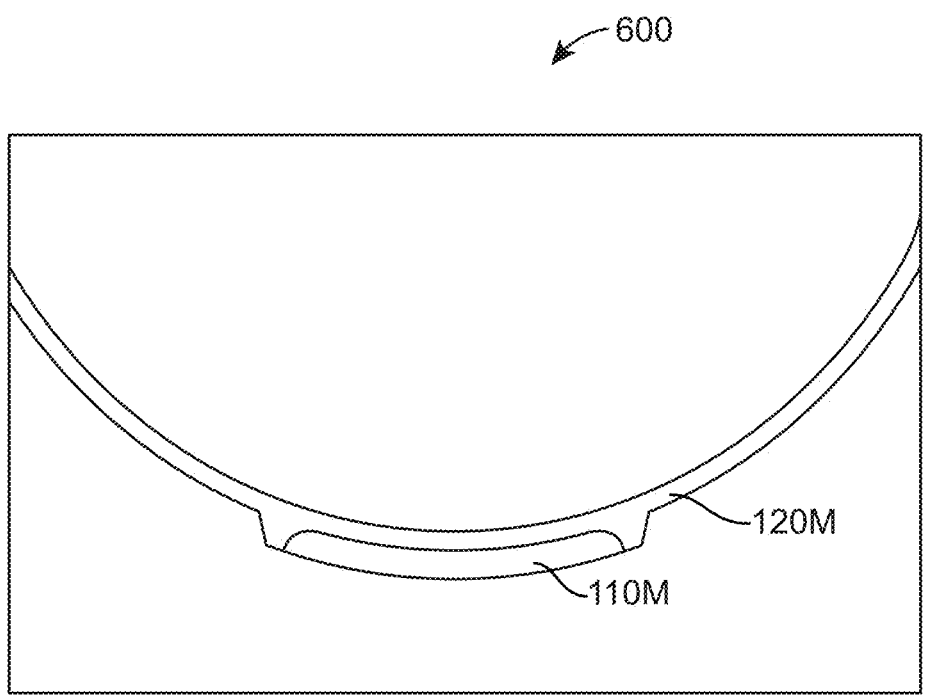

FIG. 1J6 shows a tapered edge of the covering having a tricurve profile to fit sclera and an ablated cornea as in FIG. 1J5. The third portion 132 may comprise a flange 120F having a narrowing taper extending a distance 120FW to a chamfer 120FE. The chamfer 120FE can be defined along an outer rim where a first convexly curved lower surface joins a second convexly curved upper surface. The convex surfaces along the outer rim allow the covering to slide along the conjunctiva and the narrowing taper permits the third portion of the covering to stretch substantially and couple to the sclera and conjunctiva with decreased resistance for comfort.

The dimensions of the covering 100 can be determined in many ways, for example with topography measurements of the cornea and sclera. The corneal and scleral topography can be measured with many instruments, such as with the Orbscan™ topography system commercially available from Bausch and Lomb, and the Pentacam™ Scheimpflug camera system commercially available from Oculus. The ablation profile can be combined with the topography to determine the shape of the eye.

Figure 1K:
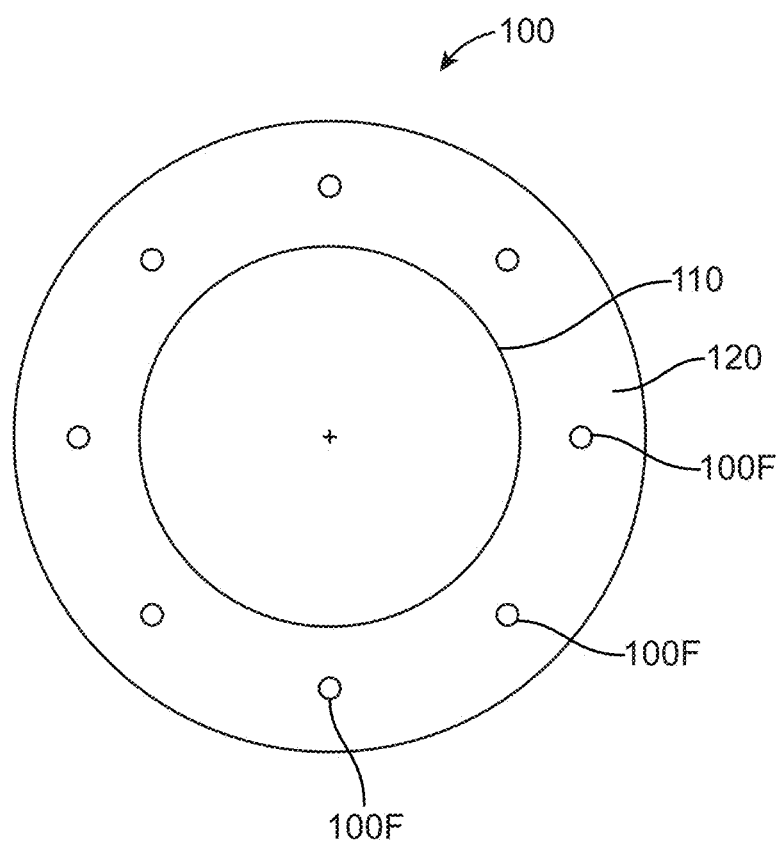
FIG. 1K shows a covering having fenestrations on an outer portion to pass a medicament when the cornea is sealed, in accordance with embodiments of the present invention.

FIG. 1K shows covering 100 having inner portion 110 and outer portion 120, and fenestrations 100F extending through the thickness of the covering on the outer portion so as to pass a medicament when the cornea is sealed. The medicament may comprise an anesthetic, an analgesic, or other medication, for example. The covering sealed to the cornea can inhibit the egress of the medicament toward the epithelial defect so that reepithelialization is not delayed. For example, an anesthetic such as proparacaine, lidocaine can be used to inhibit pain when the epithelium regenerates.

Figure 1L:
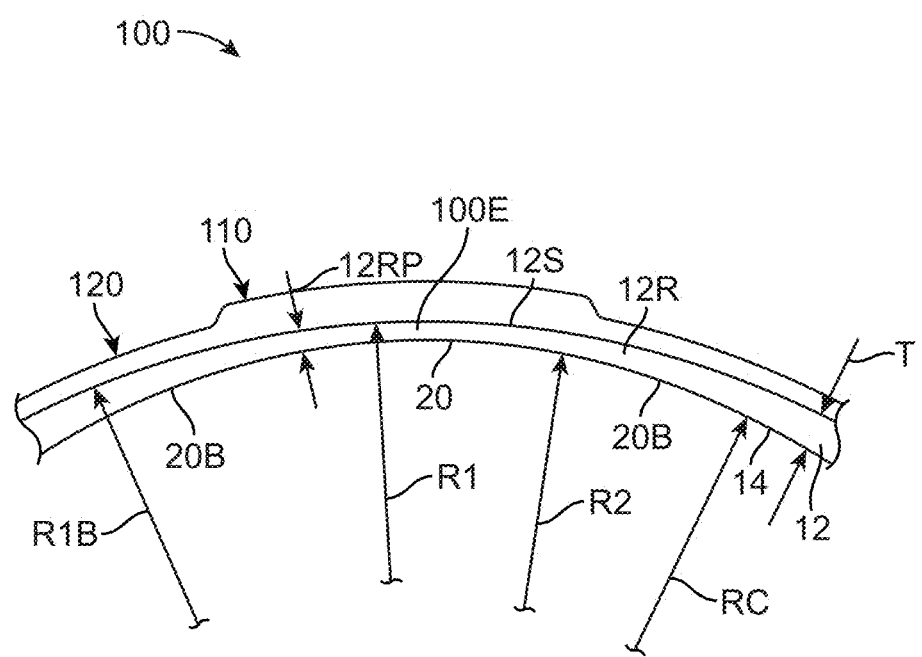
FIG. 1L shows fitting of a covering to a cornea in accordance with embodiments as described herein.

FIG. 1L shows fitting of a covering 100 to a cornea. The covering may comprise a base curvature, for example first radius of curvature R1 of inner portion 110 that may correspond to a radius of curvature when the covering comprises first configuration C1 prior to placement on the cornea. The covering may comprise a second radius of curvature R1B. The ablated cornea may comprise a second radius of curvature R2. The outer unablated portion of the curvature may comprise a corneal radius of curvature RC. The second radius of R2 of the outer portion 120 can be sized to fit the outer unablated portion of the cornea having radius of curvature RC, for example to within about +/−1D corresponding to within about +/−0.2 mm for RC of about 8 mm.

The first radius of curvature R1 can be greater than the ablated radius curvature R2 such that the curvature of the inner portion of the covering is less than the curvature of the cornea. As the curvature is inversely related to the radius of curvature, the inner portion 110 has a curvature less than the curvature of the ablation profile 20 of the cornea when the base radius of curvature R1 of the inner portion is greater than the radius of curvature R2 of the ablated cornea. The covering having substantially uniform thickness as described herein with the curvature less than the ablated cornea can correct visual aberrations that may be related to epithelial irregularity 12I, for example so as to correct temporary myopia related to irregularity 12I.

Work in relation to embodiments indicates that environment 100E to promote epithelial regeneration can be enhanced when the curvature of the inner portion 110 is less than the curvature of the ablated cornea corresponding to radius R2. The base radius of curvature R1 sized greater than the radius of curvature R2 of the ablated profile 20 can define environment 100E with a concave meniscus profile such that pressure near the boundary of inner portion 110 is decreased to encourage epithelial migration inward as indicated by arrows 30 and pressure near a center of inner portion 110 is increased so as to inhibit formation of irregularity 12I and provide smooth regeneration of the epithelium. For example, the inner portion of the covering can have a curvature corresponding to about 1 to about 2.5 D less optical power than the ablated profile 20. This amount of lesser curvature of the covering can correct temporary myopia related to epithelial irregularity 12I and may also smooth the irregularity based on the deflection pressure as described herein, for example.

While the outer portion 120 can be fit in many ways, the outer portion 120 may comprise radius of curvature R1B corresponding to about 0 to 2D less optical power than the corresponding optical power of the unablated cornea having curvature RC. For example, the unablated portion of the cornea may have an optical power of about 43D, and the outer portion 120 may have a curvature R1B corresponding to about 41 to 43D, such that the covering is fit on the cornea with a fit ranging from matched to loose. Such fitting can be used with tri-curved coverings as described herein.

The tri-curve and oblate covering profiles as described herein can be sized similarly to the bicurve surface so as to provide inner portion 110 with a decreased curvature and increased radius of curvature relative to ablation profile 20 so as to promote epithelial regeneration. For example inner portion 110 may comprise an increased apical radius of curvature relative to the radius of curvature of the ablation profile 20 of the cornea.

The amount of decreased curvature of inner portion 110 can be characterized in many ways, for example with Diopters of the cornea and Diopters of the front or back surface of the inner portion of the covering. In many embodiments the covering may comprise an inner portion having radius of curvature R1 that can be about 2 D less than the optical power of the ablated cornea. For example, when the cornea is ablated from about 43D to about 40D, the base radius of curvature R1 of covering 100 correspond about 38D, two Diopters flatter than the ablated cornea so as to provide environment 100E.

The deflectable coverings having the amount of relative rigidity within the ranges as described herein can be fit to the ablated cornea in many ways. As the covering deflects, the patient can be fit with a covering that can be flatter or steeper than the ablation prior to placement on the eye, and when the covering is placed on the eye the covering can deflect substantially in response to the shape of the ablation so that the patient can see and receive the visual benefit of the ablation profile.

In many preferred embodiments, the amount of the difference in curvature between the front surface of the ablation profile and the covering prior to placement on the eye can be within a range from about 0 D to about 3 D so as to promote vision and epithelial regeneration. For example, the covering prior to placement with configuration C1 can be flatter than the cornea by an amount within a range from about 1 D to about 3 D, and when placed on the eye the covering deflects so as to conform at least partially to the ablated cornea. The epithelium may comprise a thickness of about 50 um. The covering prior to placement with configuration C1 having a curvature flatter than the cornea can decrease pressure to the epithelium near the edge of the covering as the covering with the flatter curvature may be deflected less when the inner portion conforms to the ablation. The covering prior to placement with configuration C1 having a curvature flatter than the cornea can increase pressure to the epithelium along the inner portion of the ablation as the covering may be deflected less when the inner portion conforms to the ablation.

In many embodiments the inner portion 110 has a substantially uniform thickness and no substantial optical power such that the optical power of the covering corresponding to the index of refraction of the covering, the upper surface of the covering, and the lower surface of the covering, comprises no more than about +/−1.5D, for example no more than +/−1D. When the covering having the substantially uniform thickness is placed on the eye and deflected so as to conform at least partially to the ablation and smooth the inner 2-3 mm of the cornea, the covering corresponds substantially to the ablation profile such that the patient can see.

Figure 1M:
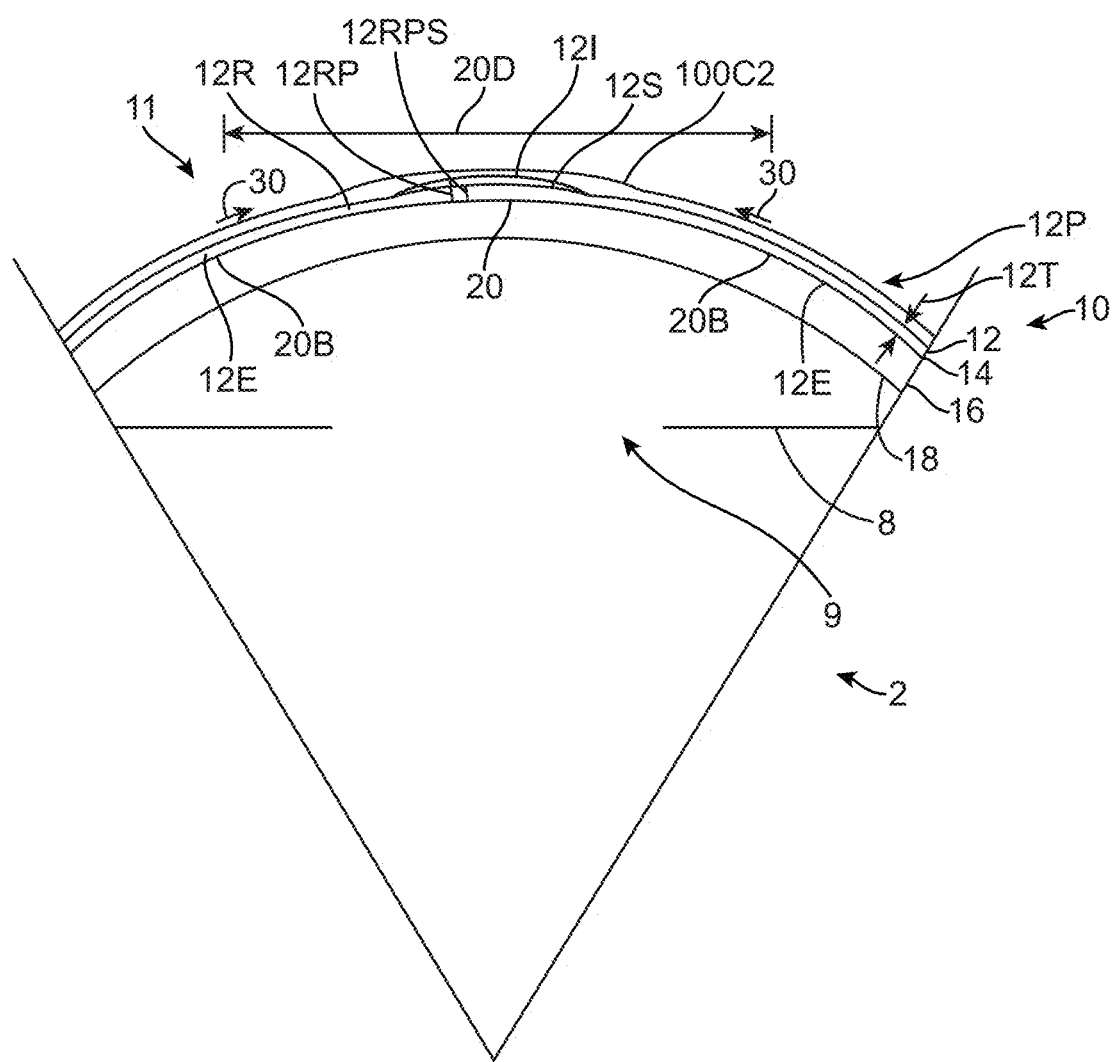
FIG. 1M shows deflection of a portion of a covering in response to an epithelial irregularity so as to smooth the irregularity, in accordance with embodiments as described herein.

FIG. 1M shows deflection of a portion of a covering in response to an epithelial irregularity so as to smooth the irregularity. The regenerating epithelium comprises a smoothed regeneration profile 12RPS and a smoothed irregularity 12S. For reference, the regeneration profile 12RP without the covering and irregularity 12I without the covering are shown. The covering can smooth the epithelium with pressure corresponding to deflection of the covering as described when the covering 100 comprises a second configuration 100C2 as herein.

Figure 1N:
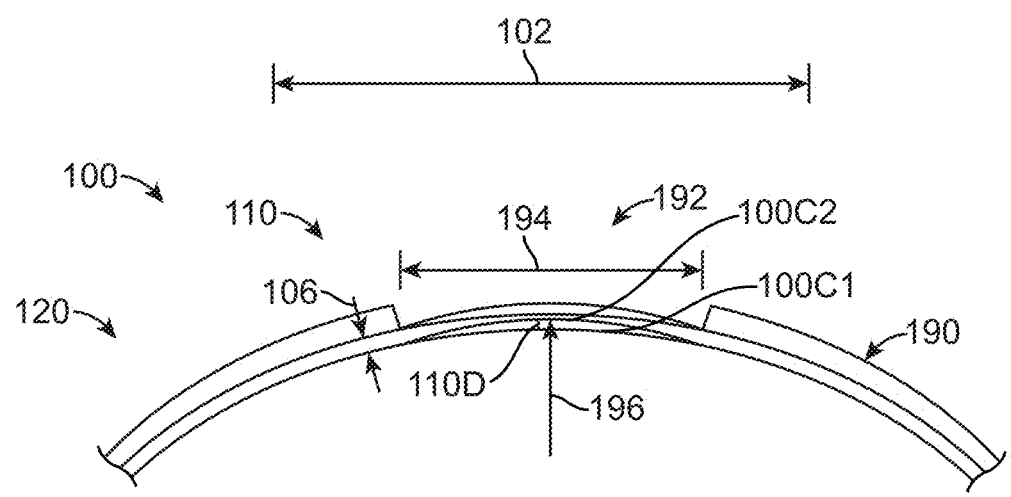
FIG. 1N shows a test apparatus to measure deflection of a portion of a lens in response to a load, in accordance with embodiments as described herein.

FIG. 1N shows a test apparatus 190 to measure deflection of a portion of a lens in response to a load. The test apparatus 190 may comprise a rigid support having an aperture 192, such that deflection of the covering 100 through the aperture 192 can be measured. The aperture 192 has a dimension across 194 that can be sized smaller than the dimension across inner portion 110, so as to measure a deflection 110D of the inner portion 110 in response to a load 196. The deflection 110D may comprise a peak deflection, for example a distance. The load 196 may comprise a point load or a load distributed over an area corresponding to diameter 104, for example a pressure from a gas or liquid on the lower side of the covering. The covering may comprise a first configuration C1 corresponding to the shape of the covering prior to placement on the eye, and the covering may comprise a second configuration C2 when placed on the eye, and the amounts of force and/or pressure to deflect covering 100 can be determined such that covering 100 can be deflected without substantially degrading vision and so as to smooth the epithelium. For example, the covering may deflect slightly so as to decrease vision no more than about 1 or 2 lines of visual acuity and such that the covering can smooth the epithelium and provide environment 100E as described herein.

The modulus and thickness of the covering can be used to determine an amount of relative rigidity of the covering 100, the corresponding amount of force to deflect the covering 100 across a distance, and the corresponding amount pressure to smooth the epithelium with the deflected covering as described herein.

The amount of relative rigidity can be determined based on the modulus multiplied with cube of the thickness. The amount of deflection corresponds to the $6^{th}$ power of the deflected span across the covering, the modulus, and the cube of the thickness. The approximately fourth order relationship of the span to the deflection can allow the coverings as described herein to conform at least partially to the ablation profile within a range from about 4 to 6 mm, and inhibit substantially irregularities having diameters of about 3 mm or less, for example.

The deflection can be approximated with the following equation:

$$\text{Deflection} \approx (\text{constant}) * (\text{Load} * \text{Span}^{\wedge} 4) / (\text{Modulus} * \text{thickness}^{\wedge} 3)$$

The above approximation can be useful to understand the properties of covering 100, for example with a substantially uniform thickness of the inner portion. The substantially uniform thickness may comprise a thickness that is uniform to within about +/−25%, for example to within about +/−10%, such that the covering can conform substantially to at least a majority of the surface area of an ablation zone and inhibit irregularities over a smaller portion of the ablation zone corresponding to no more than a minority of the surface area of the ablation. In many embodiments, the covering conforms over an area having diameter of at least about 4 mm and inhibits irregularities over an area having a diameter of no more than about 4 mm, for example less inhibits irregularities over an area of no more than about 3 mm. For example, based on the above equations, the deflection is related to the fourth power of the span, such that for a comparable load, a 2 mm span will have about $\frac{1}{16}^{th}$ the deflection of a 4 mm span. Similarly, a 3 mm span will have a deflection that is about $\frac{1}{16}^{th}$ the deflection of a 6 mm span. As the deflection is related to the cube of the thickness, doubling the thickness can decrease the deflection by about a factor of 8. The above approximations can be combined with clinical testing to determine thicknesses and moduli suitable for incorporation in accordance with embodiments as described herein.

The equations for deflection of an unsupported circular span of a material having a substantially uniform thickness are:

$$E_c = E_1\left(\frac{t_1}{t_1+t_2}\right) + E_2\left(\frac{t_2}{t_1+t_2}\right)$$

$$\text{"Relative" Rigidity} = E_c(t_1+t_2)^3$$

$$y = \frac{3wR^4}{16Et^3}(5+v)(1-v)$$

$$w = \frac{y16Et^3}{(5+v)(1-v)3R^4}$$

where:
W=evenly distributed load over the surface, Pressure (Pa)
R=span of unsupported material (m)
E=Young's Modulus (Pa)
t=Thickness (m)
v=Poisson's Ratio (unit-less, assumed to be constant among materials)
y=Deflection (m)

Equations for deflection is described in *Theory and analysis of elastic plates*, Junuthula Narasimha Reddy, p. 201 equation 5.3.43 (1999).

Although the above equations describe relative rigidity for a substantially flat surface, the equations can approximate a curved surface and a person of ordinary skill in the art can determine the deflection load and relative rigidity empirically based on the teachings described herein, for example with finite element modeling.

Work in relation to embodiments in accordance with clinical studies as described herein has shown that the inner portion 110 of the covering 100 having the relative rigidity of about 3E-4 ($3\times10^{-4}$ Pa*m^3) can be effective so to improve vision and conform at least partially of the eye so as to provide at least some comfort and improve fitting. Many eyes have been measured with many coverings and work in relation to embodiments indicates that an inner portion 110 having a relative rigidity within a range from

TABLE A1

Material, modulus, thickness, relative rigidity Dk/and deflection load of inner portions of coverings as described herein.

| Button Material | Uniform Button Thickness (um) | Button Thickness (m) | Flexural Modulus (MPa) | Flexural Modulus (Pa) | Relative Rigidity (Pa * m^3) | Material Dk | Dk/t |
|---|---|---|---|---|---|---|---|
| Rigid Silicone | 250 | 2.50.E−04 | 35 | 35000000 | 5.47E−04 | 600 | 240 |
| Rigid Silicone | 200 | 2.00.E−04 | 35 | 35000000 | 2.80E−04 | 600 | 300 |
| Rigid Silicone | 150 | 1.50.E−04 | 35 | 35000000 | 1.18E−04 | 600 | 400 |
| Rigid Silicone | 100 | 1.00.E−04 | 35 | 35000000 | 3.50E−05 | 600 | 600 |
| Rigid Silicone | 50 | 5.00.E−05 | 35 | 35000000 | 4.38E−06 | 600 | 1200 |
| Exemplary Silicone | 293 | 2.93.E−04 | 20 | 20000000 | 5.03E−04 | 600 | 205 |
| Exemplary Silicone | 272 | 2.72.E−04 | 20 | 20000000 | 4.02E−04 | 600 | 221 |
| Exemplary Silicone | 250 | 2.50.E−04 | 20 | 20000000 | 3.13E−04 | 600 | 240 |
| Exemplary Silicone | 215 | 2.15.E−04 | 20 | 20000000 | 1.99E−04 | 600 | 279 |
| Exemplary Silicone | 200 | 2.00.E−04 | 20 | 20000000 | 1.60E−04 | 600 | 300 |
| Exemplary Silicone | 175 | 1.75.E−04 | 20 | 20000000 | 1.07E−04 | 600 | 343 |
| Exemplary Silicone | 150 | 1.50.E−04 | 20 | 20000000 | 6.75E−05 | 600 | 400 |
| Exemplary Silicone | 100 | 1.00.E−04 | 20 | 20000000 | 2.00E−05 | 600 | 600 |
| Exemplary Material | 50 | 5.00.E−05 | 20 | 20000000 | 2.50E−06 | 600 | 1200 |
| enflufocon A (Boston ES) | 25 | 2.50.E−05 | 1900 | 1900000000 | 2.97E−05 | 18 | 72 |
| enflufocon A | 50 | 5.00.E−05 | 1900 | 1900000000 | 2.38E−04 | 18 | 36 |
| enflufocon A | 150 | 1.50.E−04 | 1900 | 1900000000 | 6.41E−03 | 18 | 12 |
| hexafocon B (Boston XO2) | 25 | 2.50.E−05 | 1160 | 1160000000 | 1.81E−05 | 141 | 564 |
| hexafocon B | 50 | 5.00.E−05 | 1160 | 1160000000 | 1.45E−04 | 141 | 282 |
| hexafocon B | 150 | 1.50.E−04 | 1160 | 1160000000 | 3.92E−03 | 141 | 94 |

As shown in Table A1, an RGP material such as an enflufocon or hexafocon having a thickness of about 50 um can have a relative rigidity suitable for epithelial smoothing and so as to conform at least partially to the ablated stroma. The rigid silicone having a modulus of about 20 MPa and a thickness of about 250 um will provide a relative rigidity 3E-4 and deflection under load similar to the RGP material having a thickness of about 50 um and modulus of about 1900 MPa so as to provide a relative rigidity of about 2.4E-4. Commercially available RGP lens materials as shown in Table A1 can be combined in accordance with embodiments described herein so as to provide covering 100. Based on the teachings described herein, a person of ordinary skill in the art can determine the thickness of the covering based on the modulus and the intended relative rigidity.

about 1E-4 to about 5E-4 (Pa*m^3) can allow the covering to conform to the ablation and smooth the epithelium as described herein. For example, inner portion 110 may a relative rigidity within a range from about 2E-4 to about 4E-4, and the eye can be fit accordingly based on the deflection of the covering 100.

The relative rigidity can be related to the amount of deflection of the covering 100 on the eye. Work in relation to embodiments indicates that a relative rigidity of inner portion 110 about 3E-4 can deflect about +/−2D when placed on the eye so as to conform to an ablation to within about +/−2D across the approximately 5 or 6 mm ablation diameter when an inner diameter of about 2 or 3 mm is smoothed. A covering 100 having a relative rigidity of about 1.5 E-4 can deflect about +/−4D when placed on the eye so as to conform to an ablation to within about +/−4D across an approximately 5 or 6 mm diameter when an inner diameter of about 2 or 3 mm is smoothed.

The outer portion of the covering may comprise a relatively rigidity less than the inner portion to fit an outer portion of the eye such as an outer portion of the cornea or to fit the sclera when placed on the conjunctiva.

The coverings as described herein may comprise a relative rigidity corresponding to a range within two or more values of many of the coverings of Table A1, for example a relative rigidity within a range from about 2.50E-06 to about 6.41E-03 (Pa*m^3), and two or more intermediate values for example within a range from about 6.75E-05 to about 5.47E-04 (Pa*m^3). Based on the teachings described herein the covering can have a relative rigidity within one or more of many ranges such as within a range from about 0.5 E-3 to about 10 E-3 (Pa*m^3), for example a range from about 1 E-3 to about 6 E-3, for example. Based on the teachings described herein, a person of ordinary skill in the art can conduct clinical studies to determine empirically the thickness and modulus corresponding to a relative rigidity of the inner portion 110 for the covering 100 so as to smooth irregularities and conform substantially to the ablation zone.

TABLE A2

Pressure for 5 um deflection at diameters of 3, 4, 5 and 6 mm for coverings of Table A1.

| Button Material | Button Thickness (um) | Relative Rigidity (Pa * m^3) | Pressure Required to obtain 5 um deflection (Pa) | | | |
|---|---|---|---|---|---|---|
| | | | 3 mm span | 4 mm span | 5 mm span | 6 mm span |
| Rigid Silicone | 250 | 5.47E-04 | 1002.2 | 317.1 | 129.9 | 62.6 |
| Rigid Silicone | 200 | 2.80E-04 | 513.1 | 162.4 | 66.5 | 32.1 |
| Rigid Silicone | 150 | 1.18E-04 | 216.5 | 68.5 | 28.1 | 13.5 |
| Rigid Silicone | 100 | 3.50E-05 | 64.1 | 20.3 | 8.3 | 4.0 |
| Rigid Silicone | 50 | 4.38E-06 | 8.0 | 2.5 | 1.0 | 0.5 |
| Exemplary Silicone | 293 | 5.03E-04 | 921.9 | 291.7 | 119.5 | 57.6 |
| Exemplary Silicone | 272 | 4.02E-04 | 737.6 | 233.4 | 95.6 | 46.1 |
| Exemplary Silicone | 250 | 3.13E-04 | 572.7 | 181.2 | 74.2 | 35.8 |
| Exemplary Silicone | 215 | 1.99E-04 | 364.3 | 115.3 | 47.2 | 22.8 |
| Exemplary Silicone | 200 | 1.60E-04 | 293.2 | 92.8 | 38.0 | 18.3 |
| Exemplary Silicone | 175 | 1.07E-04 | 196.4 | 62.2 | 25.5 | 12.3 |
| Exemplary Silicone | 150 | 6.75E-05 | 123.7 | 39.1 | 16.0 | 7.7 |
| Exemplary Silicone | 100 | 2.00E-05 | 36.7 | 11.6 | 4.8 | 2.3 |
| Exemplary Silicone | 50 | 2.50E-06 | 4.6 | 1.4 | 0.6 | 0.3 |
| enflufocon A (Boston ES) | 25 | 2.97E-05 | 54.4 | 17.2 | 7.1 | 3.4 |
| enflufocon A | 50 | 2.38E-04 | 435.2 | 137.7 | 56.4 | 27.2 |
| enflufocon A | 150 | 6.41E-03 | 11751.3 | 3718.6 | 1523.0 | 734.5 |
| hexafocon B (Boston XO2) | 25 | 1.81E-05 | 33.2 | 10.5 | 4.3 | 2.1 |
| hexafocon B | 50 | 1.45E-04 | 265.7 | 84.1 | 34.4 | 16.6 |
| hexafocon B | 150 | 3.92E-03 | 7174.5 | 2270.1 | 929.8 | 448.4 |

The data of Table A1 and A2 show that the pressure to deflect a 3 mm zone a distance of 5 um can be about three times the pressure to deflect a 4 mm zone the distance of 5 um, and about 15 times the pressure to deflect the 6 mm zone the 5 um distance. For example, for the relative rigidity of about 3.13E-4 (Pa*m^3), the 5 um deflection pressures are 572.7, 181.2, 74.2, 35.8 (Pa) for diameters of 3, 4, 5 and 6 mm, respectively, such that the central 3 mm of inner portion 110 can provide a compressive force to irregularities of about 570 Pa when the inner portion 110 conforms to the ablation across a 6 mm span with a pressure of about 35 Pa, for example.

The relative rigidity and deflection pressures can be determined for many coverings based on the teachings described herein, for example for coverings having a plurality of layers having a plurality of materials.

TABLE A3

Relative Rigidity of Layered Coverings

| Total Thickness | Layered Material | Material 1 (Rigid) | | Material 2 (Soft) Flexural | | Composite | | Composite Relative Rigidity (Pa * m^3) |
|---|---|---|---|---|---|---|---|---|
| | | Thickness (m) | Modulus (Pa) | Thickness (m) | Modulus (Pa) | Thickness (m) | Modulus (Pa) | |
| 270 um thick | Exemplary Silicone Shield | 2.40E-04 | 2.00E+07 | 3.00E-05 | 2.00E+06 | 2.70E-04 | 1.80E+07 | 3.54E-04 |
| | Soft and Hard are Equal | 1.35E-04 | 2.00E+07 | 1.25E-04 | 2.00E+06 | 2.70E-04 | 1.13E+07 | 1.99E-04 |
| 150 um thick | Exemplary Silicone Shield | 1.20E-04 | 2.00E+07 | 3.00E-05 | 2.00E+06 | 1.50E-04 | 1.64E+07 | 5.54E-05 |

TABLE A3-continued

Relative Rigidity of Layered Coverings

| | | Material 1 (Rigid) | | Material 2 (Soft) Flexural | | Composite | | |
|---|---|---|---|---|---|---|---|---|
| Total Thickness | Layered Material | Thickness (m) | Modulus (Pa) | Thickness (m) | Modulus (Pa) | Composite Thickness (m) | Modulus (Pa) | Relative Rigidity (Pa * m^3) |
| | Soft and Hard w/ Equal thickness | 7.50E−05 | 2.00E+07 | 7.50E−05 | 2.00E+06 | 1.50E−04 | 1.10E+07 | 3.71E−05 |

When two or more materials are combined so as to provide two or more layers, the relative rigidity of each layer can be combined so as to determine a total composite rigidity. For example, the combined rigidity can be determined for a covering having first layer 110L1 of first material, a second layer 110L2 of second material M2 and third layer 110L3 of third material 110L3, in which the first and third materials can be the same material.

A weighted average system can be used to treat the two layers as one material. The relative amounts of each material and the moduli of the two materials can be combined to determine a composite modulus based on the weight average of the thickness of each layer. For example, with 90 um of 20 Mpa material layer and a 10 um of 5 MPa material layer can be combined so as to determine the composite modulus as 20 MPa*0.9+5 MPa*0.1=18.5 MPa The equations described herein accommodate many layers of different materials and thicknesses.

Based on the composite modulus, one can multiply the composite modulus by the overall thickness cubed, in the present example 18.5 MPa*100^3. Although these calculations can be based on approximations, a person of ordinary skill in the art can conduct simulations, for example finite element modeling simulations, so as to determine the amount of relative rigidity, pressures and deflection forces and pressures as described herein.

The index of refraction of one or more layers of covering 100 may correspond substantially to the index of refraction of the cornea.

One or more of the materials 110M1, 110M2 or 110M3 may comprise an index of refraction within a range from about 1.38 to about 1.43 so as to match the index of refraction of the cornea to within about +/−0.05. For example the materials 110M1 and 110M3 may comprise an optically transparent soft silicone elastomer having an index of refraction of about 1.41 and the material M2 may comprise an optically transparent rigid silicone elastomer having an index of refraction of about 1.43, for example available from NuSil. Alternatively, material 110M1 and material 110M3 may comprise silicone hydrogel and material 110M2 may silicone, for example.

While the covering may comprise similar materials such as a more rigid silicone combined with a softer silicone, the covering may comprise dissimilar materials. For example, and RGP material can be combined with a hydrogel, such as the bicurve or tricurve embodiments as described herein. The covering can extend at least to the limbus for stability. The RGP material may comprise the second layer 110L2 of the second material 110M2, for example in accordance with Table A, and the hydrogel may comprise the first layer 110L1 of the first material 110M1 and the third layer 110L3 of the third material 110M3. The hydrogel may have an index of refraction from about 1.38 to about 1.42 so as to match the index of refraction of the cornea of about 1.377 to within about 0.05 and may comprise one or more of HEMA, NVP, GMA, MMA, SiH, TRS, HEMA/NVP, MMA/NVP, HEMA/GMA, or SiH/TRS, commercially available from Vista Optics, UK, for example. The hydrogel comprising HEMA/NVP, MMA/NVP, or HEMA/GMA may have water content within a range from about 40% to about 70% so as to comprise the index of refraction within the range from about 1.38 to about 1.43. A water content of about 40% corresponds to an index of refraction of about 1.43 and a water content of about 70% corresponds to an index of refraction of about 1.38. The hydrogel comprising SiH/TRS may comprise water content within a range from about 20% to about 70% so as to comprise the index of refraction within the range from about 1.38 to about 1.43. With these SiH hydrogels a water content of about 20% corresponds to an index of refraction of about 1.43 and a water content of about 70% corresponds to an index of refraction of about 1.38.

Surgical Placement of the Covering

FIG. 2A shows surgical placement of covering 100 on an eye having an epithelial defect with an applicator 200. The applicator 200 comprises a support 210 to carry the covering 100 and a movable component 230 to advance the covering onto the cornea with motion 240. The support 210 comprises an opening 212 sized to receive the movable component 230. The support 210 may comprise a lower portion 220 to couple to the covering, for example to adhere to the covering, and a handle 214. Coupling 220 of the support to the covering can be used to carry the covering for alignment and placement on the cornea. The support may comprise a rigid structure, for example a rigid annular structure 216, to couple the handle to the lower portion of the support. The handle 214 may comprise a neck 214N that extends to the rigid annular structure 216.

The movable component 230 can be sized and shaped in many ways to advance the covering 100 onto the eye with the support 210. For example, the movable component 230 may comprise a disc shape portion of a window 232 sized to pass within opening 212. The disc shaped portion of rod comprising window 232 may comprise a window composed of an optically transparent material, for example an optically transparent material such as one or more of a rigid material, glass, glass fibers, plastic, polyacrylate, polyimide, silicone. Alternatively the movable component may comprise an annulus sized to pass within opening to contact the covering.

The support 210 and the movable component 230 each comprise at least a portion viewable therethrough such that the patient can see a fixation light and the physician can see at least one structure of the eye to align the covering with the eye when the covering is positioned on the eye. The covering can be positioned with an operating microscope 202, for example an operating microscope of a commercially laser refractive surgery system. The operating microscope 202 may comprise an objective lens 204 and an eyepiece 206 for an operator 207 such as a surgeon to view the eye. A fixation light 208 such as an LED may be positioned on the operating microscope such that the patient can view the fixation light and fixate on the light 208 so as to steady the eye.

The handle 214 can be pivoted with a hinge, bearing, or pivot mechanism disposed between the handle and the support 210 such that the handle 214 can pivot away from the operating microscope.

The covering 100 may comprise a marking 100MK to align the covering with the cornea. Alternatively or in combination, the applicator 200 may comprise a marking 200MK to align the covering with the cornea. The marking can be helpful, for example when the covering comprises an inferior rigidity less than a superior rigidity.

FIG. 2A1 shows a surgeon's view of the eye through the applicator as in FIG. 2A. The surgeon can view through opening 212 and window 232 so as to visualize a tissue structure of the eye such as the iris 8 or pupil 9. The surgeon may visualize the limbus of the eye, for example with low magnification of the microscope. The surgeon can align the structure of the eye with a structure of the applicator 200. For example, circular aperture 212 can be aligned with pupil 9.

FIG. 2A2 shows a patient's view of a fixation light through the applicator as in FIG. 2A. The patient can see the fixation light 208 through the covering and the applicator, such that the patient can fixate when the covering is placed on the cornea. Prior to placement of the covering over the ablation and epithelial defect, the patient may observe haze 208H around the fixation light, for example when the covering is positioned on cornea without liquid disposed on the surface. Although haze 208H may be present, the patient can fixate sufficiently for the surgeon to position the covering over the ablation and pupil.

FIG. 2B shows applicator 200 coupled to covering 100 for placement on a cornea as in FIG. 2A. The applicator 200 comprises a lower portion 220 to couple the applicator to covering 100. The coupling 222 of the applicator 200 to the covering 100 can be achieved in many ways, for example with one or more of adhesion, block adhesion, sticking, interlocking structures, or surface tension.

The coupling 222 of the lower port may comprise block adhesion. For example, the lower portion 220 may comprise silicone and the covering may comprise silicone. The covering can be placed in contact with the lower portion 220 in the presence of a solvent such as alcohol, and the solvent evaporated such that the covering 100 is adhered to the lower portion 220. Similar adhesion can be achieved with a wettable coating disposed over the covering 100, as described above. The lower portion 220 may comprise a wettable coating to contact the covering.

Work in relation to embodiments suggests that in some instances the lower sticky tacky surface of outer portion 120 can stick to itself during deployment onto the eye, and the applicator 200 can improve handling when the covering 100 is placed on the eye.

The covering used with the applicator may comprise many coverings, for example a covering as described above, a covering as described in U.S. patent application Ser. No. 12/384,659, filed Apr. 6, 2009, entitled "Therapeutic Device for Pain Management and Vision", previously incorporated herein by reference, or a commercially available covering, such as a commercially available therapeutic contact lens or a commercially available hybrid lens comprising an RGP inner portion and a hydrogel skirt.

FIG. 2C shows applicator 200 coupled to covering 200 with coupling 222 comprising block adhesion and peeling 242 of the covering from the applicator with movable component 230. The lower portion 220 may contact the covering 100 with an angle such that the covering peels from the support when the movable component is advanced. Such peel can be effective to remove the covering when the covering is adhered to the support.

FIG. 2C1 shows applicator 200 coupled to covering 100 with foam 222F to adhere to the covering to the applicator when dry and application of a liquid 222L to release the covering from the applicator when wet. Alternatively, the foam 222F can couple the applicator 200 covering 100 such that the covering can be removed with the movable component 230.

Figure 2A:
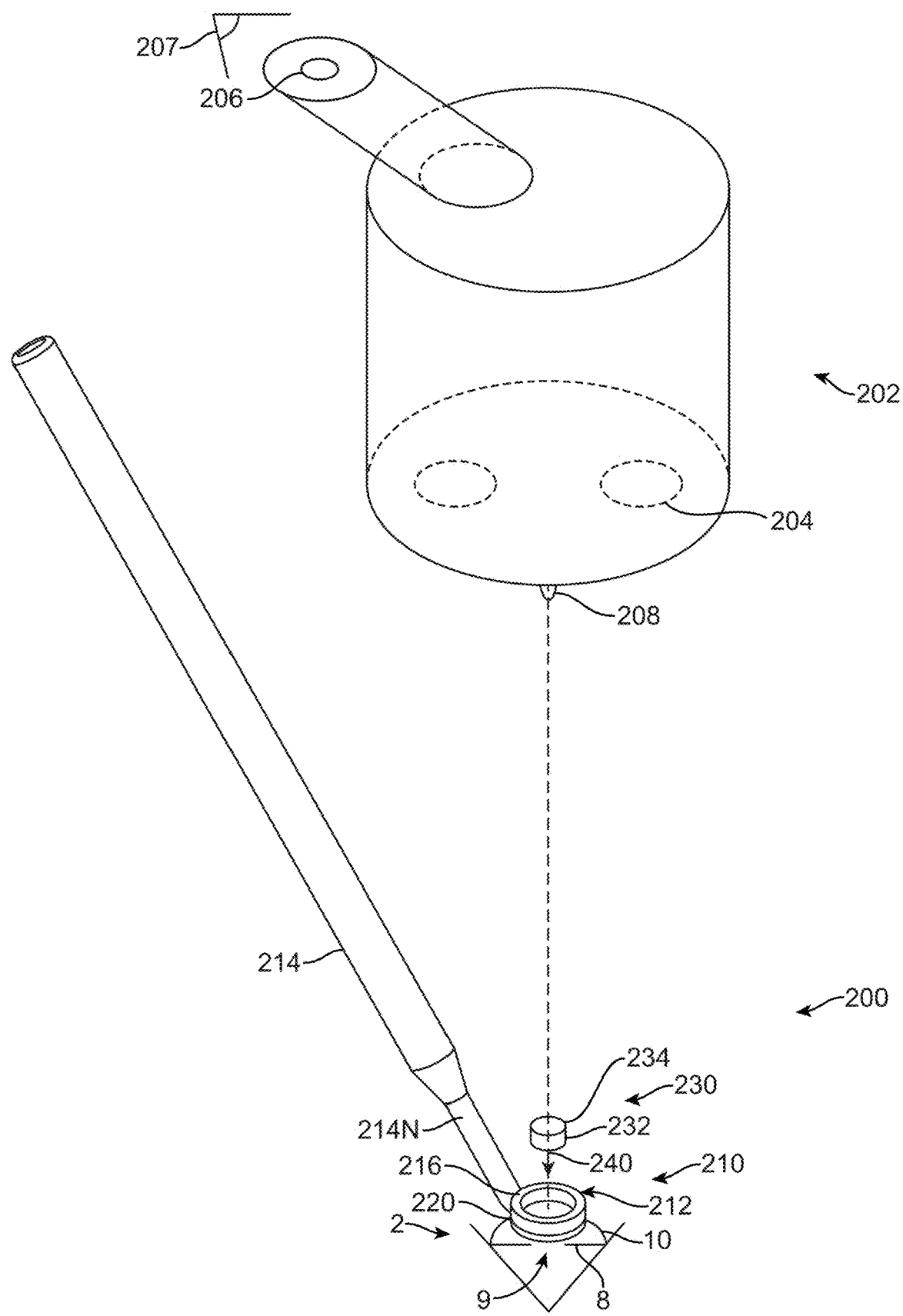
Figure 2B:
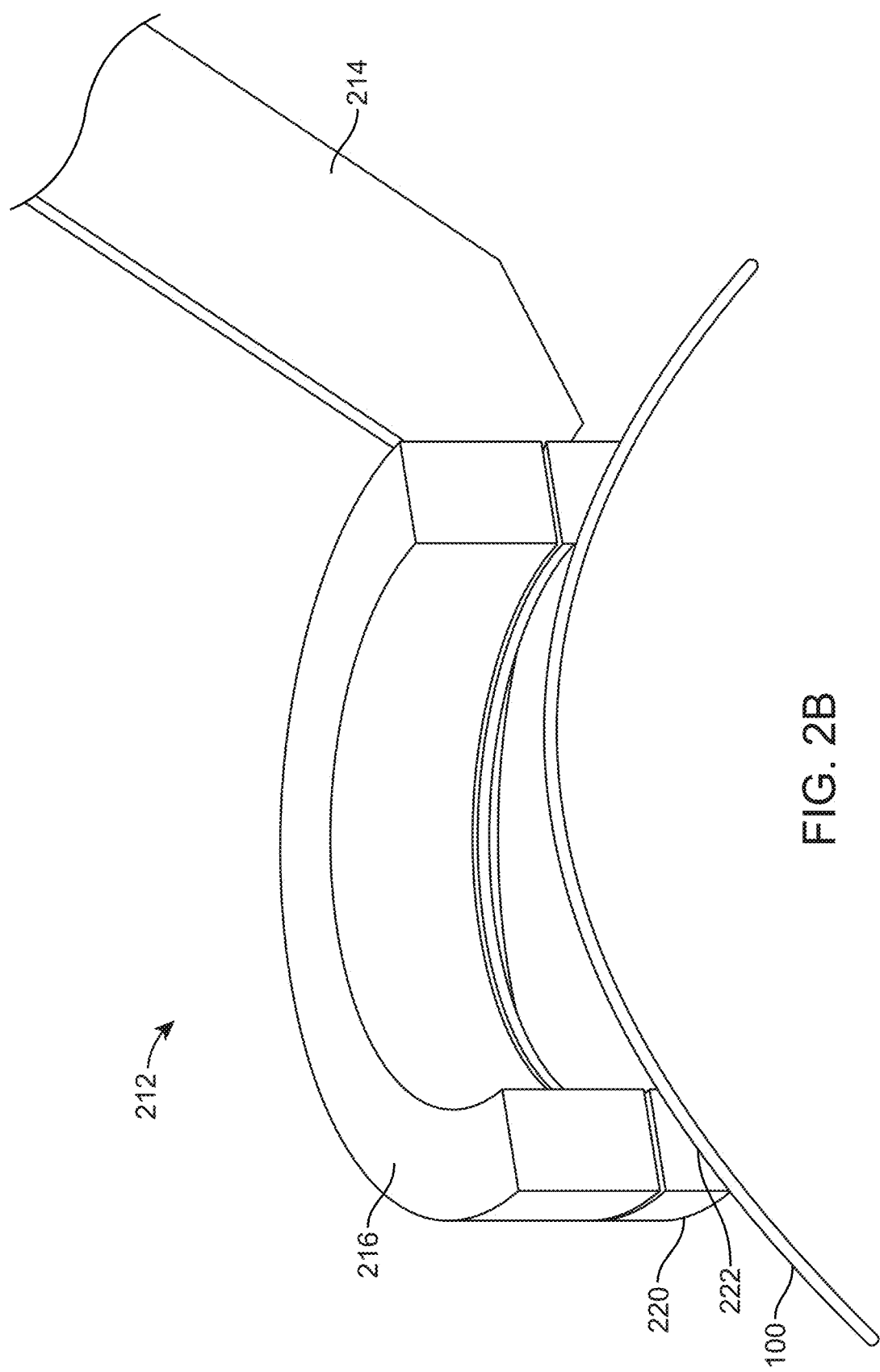
Figure 2D:
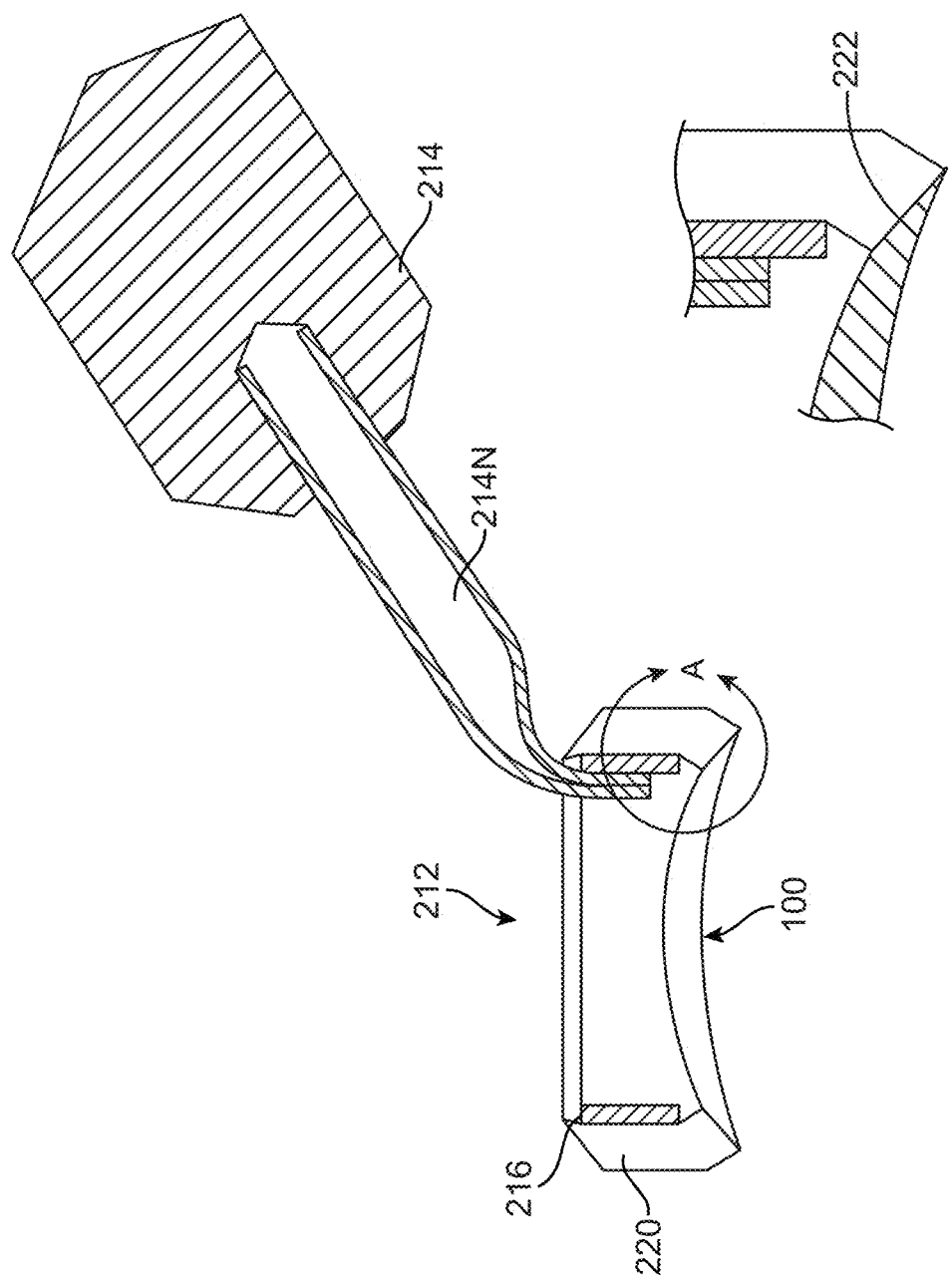
FIG. 2D shows an applicator as in FIG. 2A coupled to a covering.

FIG. 2D shows applicator 200 coupled to covering 100 with silicone to silicone adhesion. The covering lower portion 220 of the support 210 may comprise silicone and a silicone surface. In particular, lower portion 220 may comprise a very smooth ⅜"×¼" silicone tube stretched over a 0.344" ring or tube. The covering 100 may comprise silicone on the upper surface in contact with the silicone of the lower portion 220, such that covering 100 is adhered to the support with a silicone to silicone interface. The silicone to silicone interface can be formed with evaporation of a solvent when the lower portion 222 contacts the covering, as described above. Handle 214 may comprise machined Acrylonitrile Butadiene Styrene (ABS). Neck 214N may comprise 14 Gage TW 204 tube crimped and spot welded so as to attach handle 214 to annular structure 216. Annular structure 216 may comprise a 0.344" ring or a 0.344"×0.324" 304 tube.

FIG. 2D1 shows covering 100 coupled to applicator 200 with silicone to silicone adhesion and the lower surface of the lower portion 220 inclined at an angle.

FIG. 2E shows applicator 200 comprising a rigid component 250 and a flexible component 254. The flexible component 254 may comprise a concave first configuration to carry the covering 100 and a second configuration to release the covering. The rigid component 250 may comprise a window 252 of a transparent material. The flexible component 254 may comprise a thin transparent sheet of material, for example a flexible diaphragm. The flexible component can be urged downward so as to advance covering 100 downward on to the eye with movement 240.

The rigid component 252 and flexible component 254 may define a chamber 253. The chamber 253 can be filled with a fluid such as a gas or a liquid. The handle 214 may comprise a button 256 so as to deliver gas to chamber 253 with movement 258 of the button 256. The fluid may comprise a cooled fluid such as a cooled gas or a cooled liquid so as to cool the cornea and denervate the cornea, for example as described in U.S. Provisional Pat. App. Ser. No. 61/279,612, filed on 23 Oct. 2009, entitled "Corneal Denervation for Treatment of Ocular Pain", the entire disclosure of which is incorporated herein by reference and suitable for combination in accordance with at least some embodiments of the present invention as described herein.

The chamber 253 can be configured to displace a predetermined quantity of air, for example with a syringe to displace the movable component a predetermined amount toward the cornea. Alternatively or in combination, the handle may comprise a bulb to displace the movable component with movement of the fluid.

FIG. 2E1 shows coupling of a covering to an applicator as in FIG. 2E. The thin flexible component 254 can extend substantially along covering 100. The thin flexible component 254 may comprise a coating to inhibit adherence of the covering to the thin flexible component. The covering may be adhered to lower portion 220 with adhesion as described above.

Figure 2F:
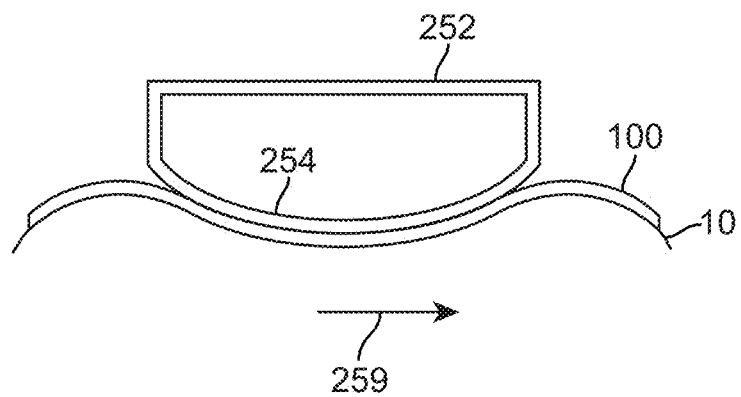
FIG. 2F shows an applicator and a covering as in FIG. 2E with the applicator in an expanded configuration to position the covering on the cornea, in accordance with embodiments of the present invention.

FIG. 2F shows an applicator and a covering as in FIG. 2E with the applicator in an expanded configuration to position the covering on the cornea. The thin flexible component 254 can expand, for example to a convex configuration with expansion of chamber 252. The covering 100 can peel from the lower portion as described above.

Figure 2G:
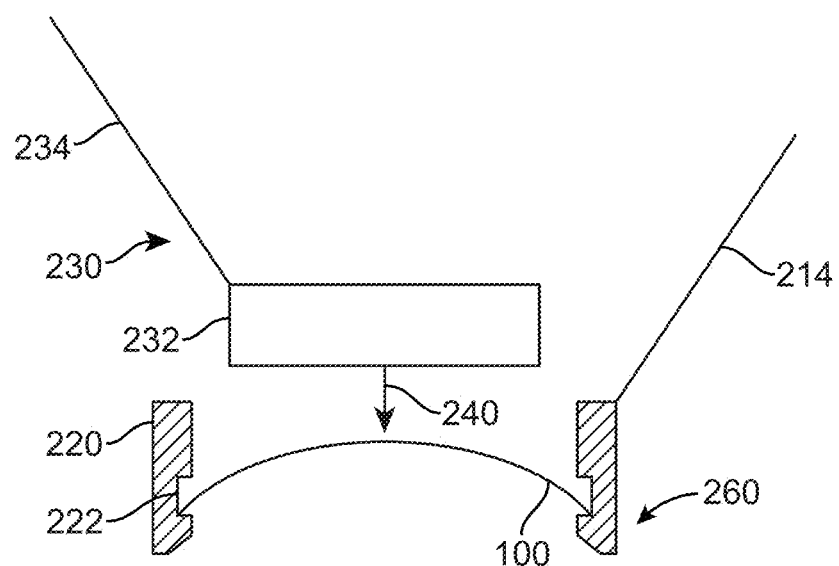
FIG. 2G shows an applicator and a covering with the covering held in a channel of the applicator, in accordance with embodiments of the present invention.

FIG. 2G shows an applicator 200 and covering 100 with the covering held in a channel 260 of the applicator. The channel 260 can be sized to receive the covering 100, for example with a diameter slightly larger than the covering.

Figure 2H:
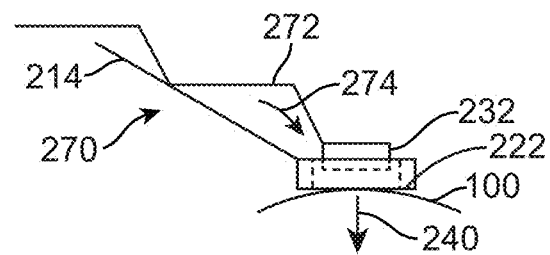
FIG. 2H shows an applicator and a covering with the applicator comprising an extension to deliver the covering, in accordance with embodiments of the present invention.

FIG. 2H shows applicator 200 and covering 100 with the applicator comprising an extension 270 to deliver the covering. The extension 270 can extend between handle 214 and movable component 230 comprising window 232 as described above. Extension 270 may comprise a flexible component 272 coupled to the window 232, such that the extension 270 can be pushed toward the eye so as to move the covering toward the eye with movement 270.

Figure 2I:
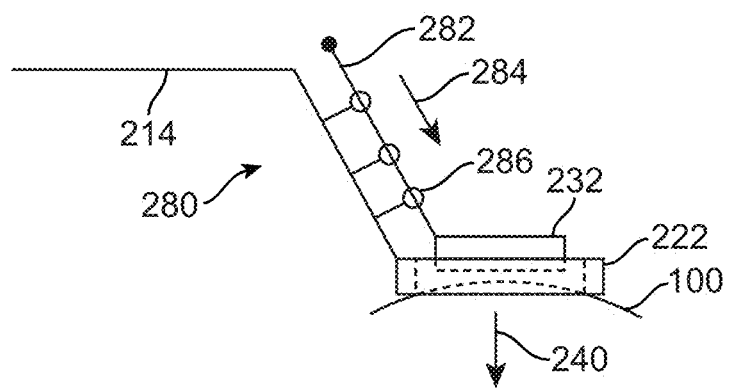
FIG. 2I shows an applicator and a covering with the applicator comprising a slider to release the covering, in accordance with embodiments of the present invention.

FIG. 2I shows applicator 200 and covering 100 with the applicator comprising a slider 270 to release the covering. The slider 270 can be slid toward the eye with movement 284 coupled to window 232 such that the covering is moved toward the eye with movement 240.

FIG. 2J shows applicator 200 and covering 100 with the applicator comprising a hinge 290 to release the covering. The hinge 290 can comprise an extension 294 movable about a pivot 292. Motion of extension 294 about pivot 292 can advance the movable component 230 comprising window 232 toward the eye with movement 240.

FIGS. 2K1 and 2K2 show side and top views, respectively, of applicator 200 and covering 100 with the applicator comprising a compressed structure 296 that is released so as to deliver the covering to the cornea. The compressed structure 296 may comprise many materials, for example a shape memory material such as nitinol, a spring, a metal, plastic, or a combination thereof. The compressed structure can be connected to the rigid portion of the support with a trigger structure 298 such as a latch, notch, L-connector, keeper or loop, such that the compressed structure can be released with movement 297 the trigger structure. The compressed structure comprises a first configuration of the movable structure of the applicator 100. The structure 296 can be sized such that the patient view of the fixation light for alignment is not occluded substantially and such that the physician view of the structure of the eye for placement of the covering on the eye is not occluded substantially.

FIG. 2K3 shows the applicator as in FIGS. 2K1 and 2K2 with the structure 296 in a released second configuration so as to deliver the covering 100 to the cornea.

Figure 3A:
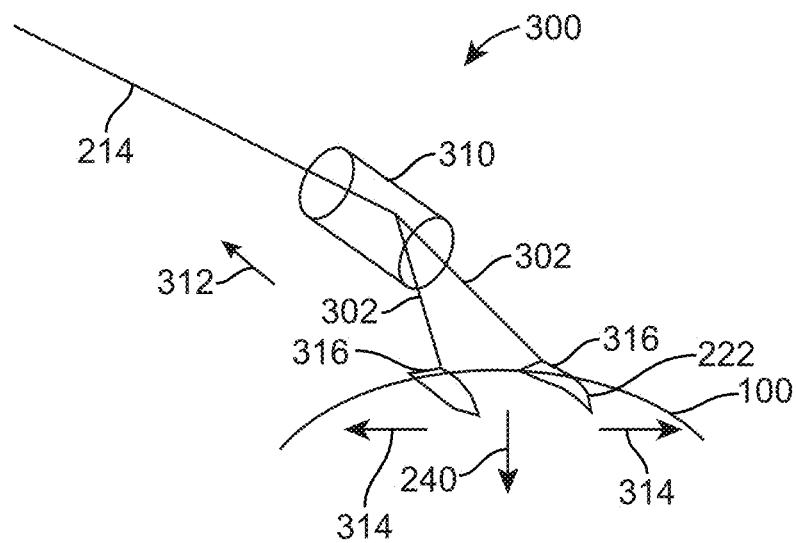
FIG. 3A shows an applicator comprising extensions coupled to pads to deliver the covering, in accordance with embodiments of the present invention.

FIG. 3A shows applicator 100 comprising a sliding mechanism 300 and extensions 302 coupled to pads 316 to deliver the covering 100. The pads 316 can be connected to covering 100 with coupling 222. The pads 316 can be spaced apart by a distance such that the patient can view the fixation light between the pads. The extensions 302 extend from pads 316 to handle 214 at an oblique angle such that the handle does not occlude the view of the fixation light and surgical view of the alignment structures of the eye. The extension 302 may comprise one or more of a flexible material, an elastic material, or a shape memory material such that the pads can urge apart when the covering is positioned on the cornea with motion 240. For example, a slider 310 can be retracted with a movement 312 such that pads 316 are urged apart with movement 314 when the covering is positioned on the cornea. The pads may comprise an inclined lower surface such that the pads can peel away from the covering when urged apart.

Figure 3B:
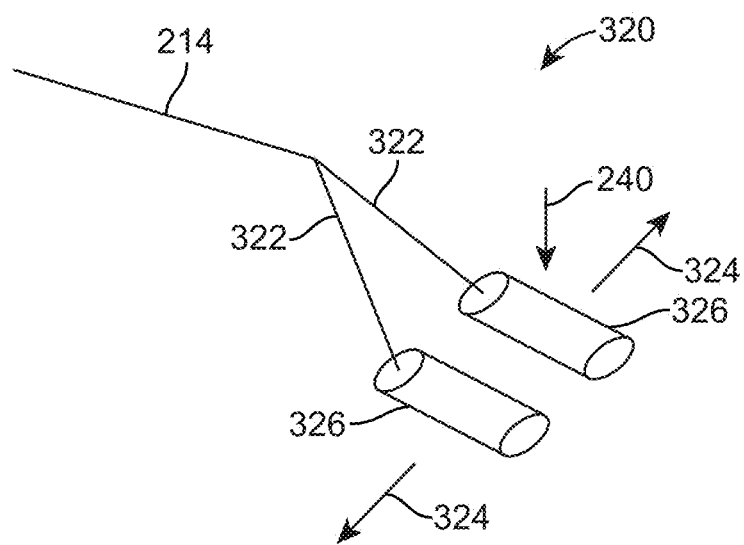
FIG. 3B shows an applicator comprising roller pads to deliver the covering, in accordance with embodiments of the present invention.

FIG. 3B shows applicator 100 a spring mechanism 320 comprising extensions 322 coupled to roller pads 326 to as to deliver the covering 100 to the cornea. The roller pads can be coupled to the covering 100 with coupling 222 as described above. Alternatively, rollers 326 can be used to smooth the covering on the eye, for example when the covering is substantially dry. The extensions 322 extend from the handle 214 to the rollers 326 and may comprise one or more of a flexible, elastic, resilient or shape memory material such that the rollers can move apart with separation 240 when positioned on the eye and urged toward the cornea with movement 240. The extensions 222 can extend from the rollers to the handle for a sufficient distance at an oblique angle such that the handle does not interfere with patient fixation. The rollers can be spaced apart by a distance such that the rollers do not interfere substantially with patient fixation and the surgeon's view of the structures of the eye.

Figure 3C:
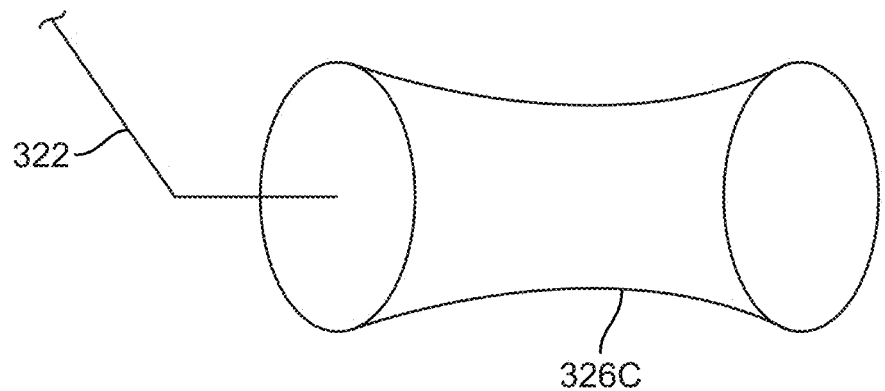
FIG. 3C shows concave roller pads for use with an applicator as in FIG. 3B, in accordance with embodiments of the present invention.

FIG. 3C shows a concave roller pad 326C for use with an applicator 100 as in FIG. 3B. Each of the roller plurality of roller pads may comprise concave roller pad 326C. The concave roller pad can fit the covering on the cornea, so as to smooth the covering onto the cornea as described above.

Figure 3D:
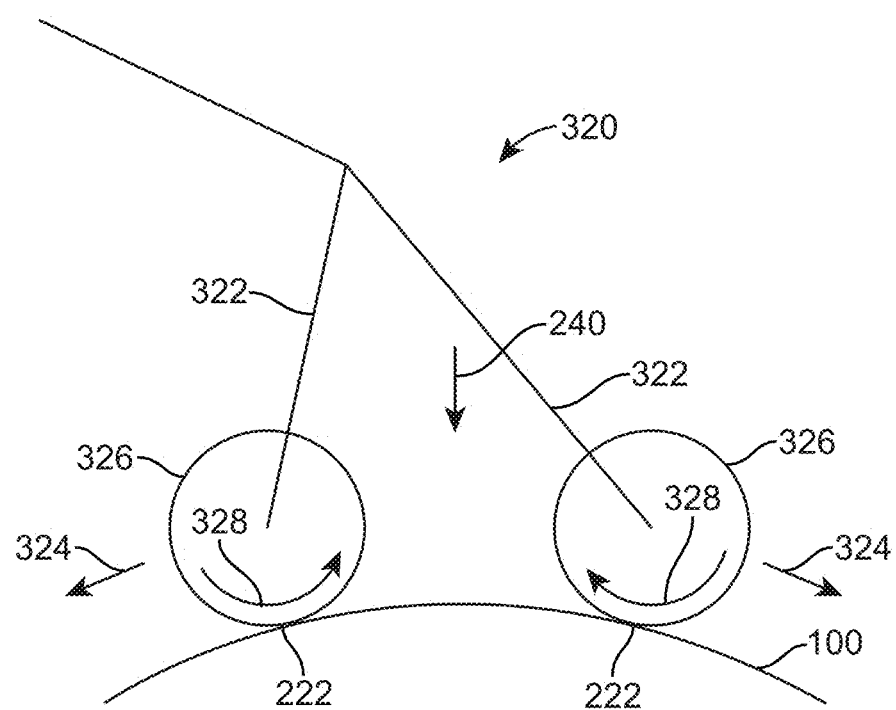
FIG. 3D shows delivery of a covering to the cornea with an applicator comprising rollers as in FIG. 3B, in accordance with embodiments of the present invention.

FIG. 3D shows delivery of a covering to the cornea with the applicator comprising rollers as in FIGS. 3B and 3C. The applicator can be coupled to the covering with coupling 222. The movement 240 toward the eye can separate the rollers 326 with movement 324. The rollers can undergo rotational movement 328 when separated with movement 324 so as to smooth the covering.

Figure 4A:
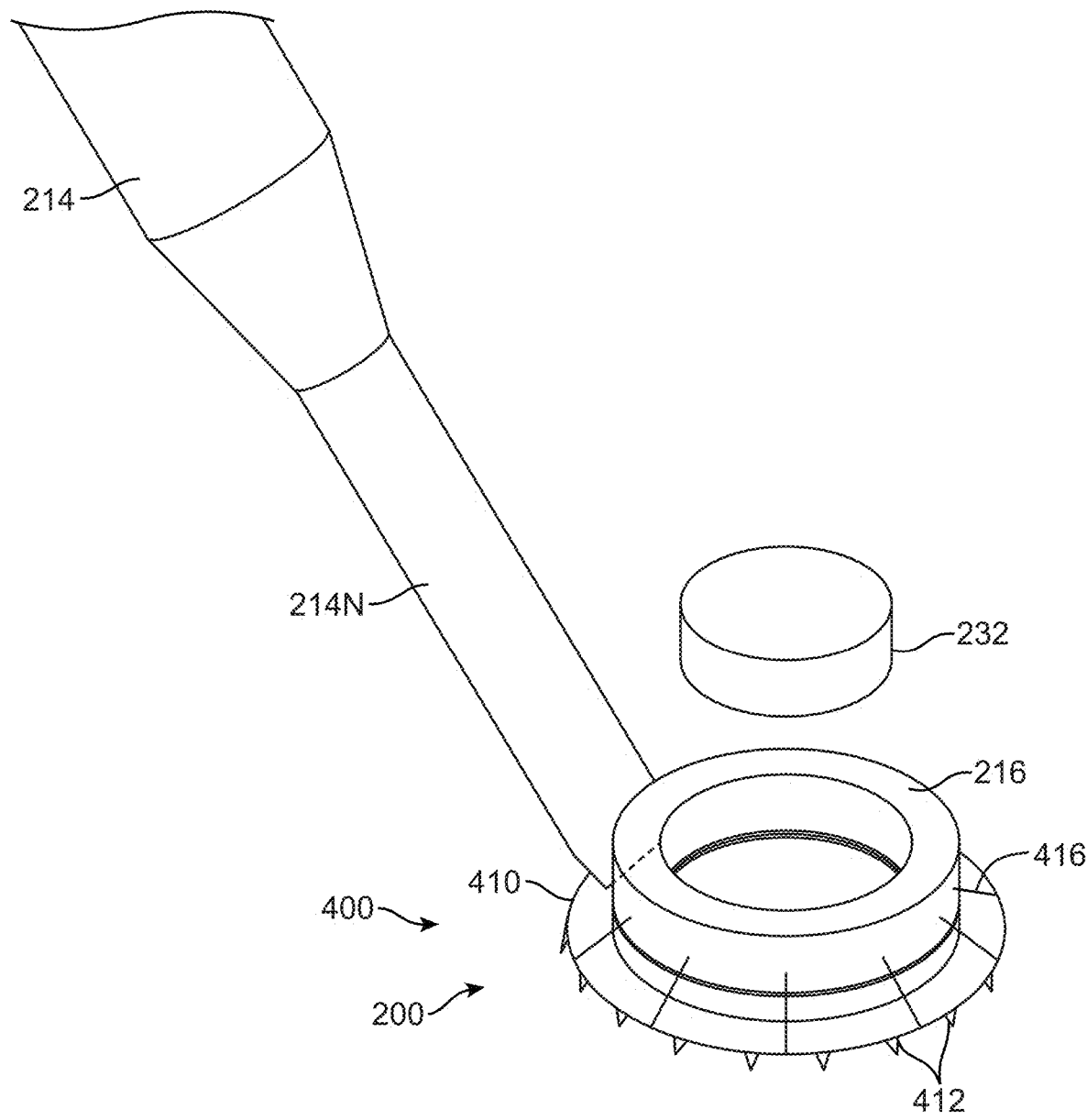
FIG. 4A shows an applicator comprising a fixation ring coupled to a covering, in accordance with embodiments of the present invention.
Figure 4B:
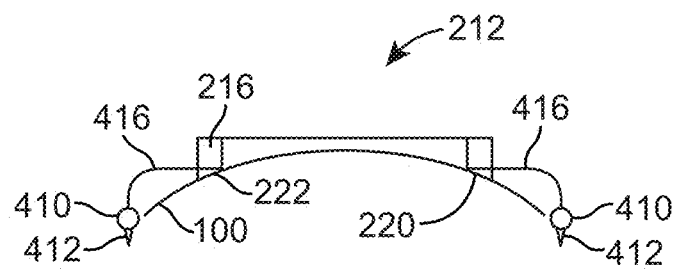
FIG. 4B shows a side view of the applicator as in FIG. 4A.

FIG. 4A shows an applicator 400 comprising a fixation ring 410, and FIG. 4B shows a side view of the applicator 400. The applicator 400 may comprise many of the components of applicator 200, as described above, coupled to fixation structure such as fixation ring 410. The fixation ring 410 can be affixed to the rigid portion 216 with extensions 416 extending from the rigid portion to the fixation ring. The fixation ring may comprise teeth 412. The teeth 412 can be sized such that the teeth engage the sclera, or the limbus, for example. The covering can be carried with coupling 222. The fixation ring 410 can be sized such that covering 100 fits within fixation ring 410. The movable component, for example window 232, can be moved toward the cornea to deliver the covering when the fixation ring engages the eye with the rigid portion and coupling 222 positioning the covering on the cornea. The applicator 400 can be used with an opaque movable component, for example a compressible foam to contact the covering.

FIG. 5A shows an apparatus 500 comprising covering 100 and applicator 200 stored in a substantially dry, sterile compartment 510 of a container. The apparatus 500 may comprise a kit. The components and packaging can be sterilized in many known ways such as e-beam, ethylene oxide gas, and gamma-ray. The apparatus 500 can be provided to the physician and opened with the applicator 200 coupled to covering 100, for example adhered to covering 100 and ready for placement on the cornea. The covering may comprise at least an optically transparent portion when dry, and the applicator and covering can be viewable therethrough when positioned on the cornea as described above.

FIG. 5B shows an apparatus 520 comprising covering 100 and applicator 200 stored in a substantially moist, sterile compartment of a container. The apparatus 520 may comprise a kit. The components and packaging can be sterilized in many known ways such as e-beam, gamma-ray, ethylene oxide and autoclave. The apparatus 520 can be provided to the physician and opened with the applicator 200 coupled to covering 100, for example adhered to coupled to 100 with support 524 to hold the covering against the applicator during shipping, such that the covering an applicator are ready for use to place the covering on the cornea. The covering may comprise at least an optically transparent portion when dry, and the applicator and covering can be viewable therethrough when positioned on the cornea as described above.

FIGS. 5B1 and 5B2 shows an apparatus comprising a covering and an applicator stored in a sterile compartment of a container, in which the container comprises a support surface with the covering disposed thereon in a channel sized to receive the applicator, in accordance with embodiments of the present invention;

FIG. 5B3 shows an applicator with a support coupled to a handle with a joint 540 disposed between the support and the handle to move the handle when the support is coupled to the eye. The joint may comprise a pivot, u-joint and additional articulating structures.

FIG. 5C1 shows an apparatus comprising a removal tool 550. The removal tool 550 may comprise an elongate structure 552 that is graspable by a user, for example a syringe or handle. The elongate structure such as the syringe may comprise a chamber having an amount of liquid disposed therein. The removal tool comprises a distal portion 560 having a tip 568. The distal portion 560 may comprise components of a known hydro dissection tip modified in accordance with the teachings described herein. The fluid, for example liquid may 550L, may comprise saline, for example, or a visco-elastic material. The distal portion 560 may comprise a first proximal extension 562 and a second distal extension 564 with an angle 566 disposed therebetween, so as to define an angle and extend substantially along a plane. The distal portion comprises a lumen that extends from the syringe to the tip 568. The cross sectional perimeter of the area of the tip comprises a long distance dimension 568L and a short distance dimension, for example major and minor axes of an elliptical cross section. The long distance dimension 568L of the cross section extends along a third direction.

The long distance dimension 568L be oriented with respect to the handle such that the third long dimension extends along the lower side of the covering. For example the long distance dimension 568L can extend along the lower surface of the covering, when the handle is positioned in a superior temporal location relative to the eye, such that fluid flows inferiorly and nasally when the covering is separated from the regenerated epithelium with the liquid.

FIG. 5C2 shows the distal portion 560 of the removal tool. The angle 566 can be from about 120 to about 150 degrees, for example 135 degrees similar to a commercially available hydro-dissection tip for cataract surgery. The distal portion 560 of the removal tool shown in FIG. 5C2 is angled at 135 degrees with a 11 mm bend to tip.

FIG. 5C3 shows the apparatus of FIG. 5C1 aligned with the patient to position the tip 568 under the covering. The patient comprises a midline M and the nose is dispose along the midline. The removal tool 550 can be positioned on either side of the midline. Alternatively the removal tool may comprise a first removal tool 550A for positioning on the right side of the patient and a second removal tool 550B for positioning on the left side of the patient. The handle of the removal tool can be positioned oblique to the midline when the tip is positioned under a temporal location of the covering, such that the physician can rest his or her hand on a support when the tip is positioned under the covering. The long dimension 568L can extend substantially along the plane of the pupil when the tip is positioned under the perimeter of the covering and aligned with the covering for removal and the handle is positioned near the temple of the patient. This alignment of the long dimension with the lower side of the covering and the plane of the pupil can decrease deformation of the epithelium when the covering is removed so as to lift the covering upward and break the seal to lift the covering upward from the cornea. Although, the long dimension 568L can extend perpendicular to the plane of the pupil when the tip is positioned under the perimeter of the covering work in relation to embodiments suggests that such perpendicular alignment may deflect the epithelium slightly and may not break the seal of the covering with the epithelium as effectively.

FIG. 5C4 shows the long dimension 568L of the cross section of the opening of tip 568 aligned substantially with a plane of the pupil and a peripheral temporal portion of the covering when the handle is positioned near the temple of the patient;

FIG. 5D shows separation of the covering 100 from the regenerated epithelium 12R with injection of the liquid 550L. The regenerated epithelium substantially covers ablated profile 20, and may comprise at least about 2-3 cell layers thick, for example a thickness of at least about 20 to 30 um. This substantial covering can occur 2 days or 3 days post-op, for example. Work in relation to embodiments suggest that the covering can remain on the cornea after the initial covering, for example up to one week post ablation with a high Dk covering providing the environment to promote reepithelialization as described herein without substantial swelling of the cornea.

FIG. 6 shows a mold 600 to form a covering and having a solid inner component comprising a rigid material placed therein prior to injection of a flowable material. The mold 600 may comprise inner material 110M positioned within the mold as a solid piece of material and outer material 120M comprising a flowable material injected into mold 600 and cured around the preformed piece comprising inner material 120M. The flowable material can be injected around the inner material 100M in many ways. For example, the inner material 110M may comprise a second layer 110L2 of rigid material 110M2 of the inner portion 110 as described herein, and the flowable material can be injected around the upper and lower surfaces of second material 110M2 so as to form a first layer 110L1 of first material 110M1 and a third layer 110L3 of the third material 110M3 with the flowable material such that the first material 110M1, the third material 110M3 and the outer material 120M each comprise substantially the same soft material when cured. Alternatively or in combination, the mold may have the first layer 110L1 of the first material 110M1 and the second layer 110L2 of the second material 110M2 placed therein, and the flowable material injected so as to form outer material 120M and the third layer 110L3 of the third material 110M3. For example, the third layer 110L3 may be formed with a solid spacer of third material 110M3 placed in the mold, and the flowable material comprising material 110M1 injected around the spacer of cured material 110M3 and layer 110M2 so as to form layer.

Figure 6A:
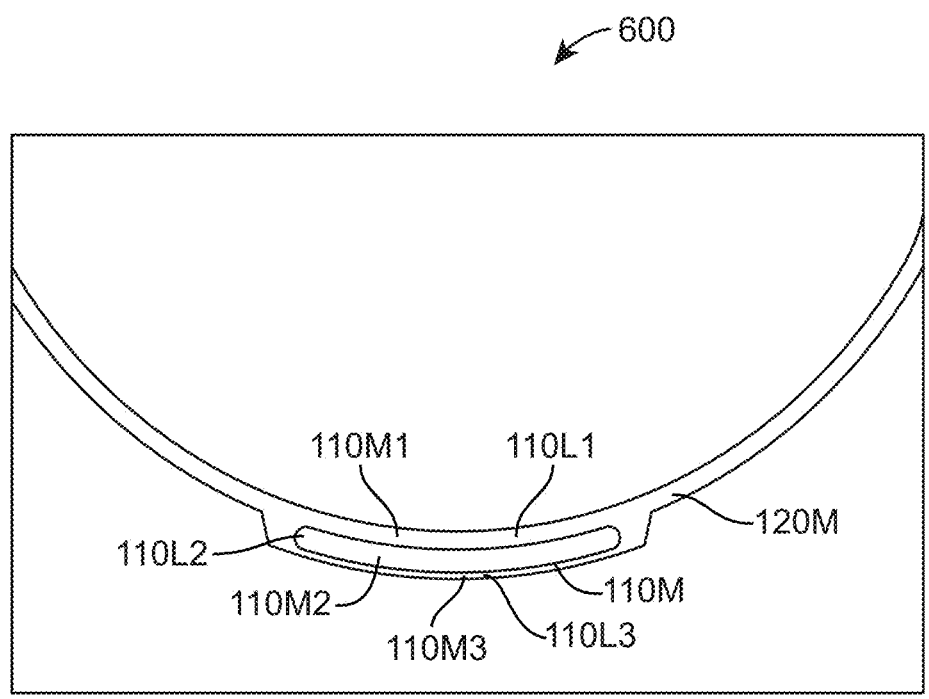
FIG. 6A shows a mold to form a covering and having a solid inner component comprising a rigid material placed therein prior to injection of a flowable material, in accordance with embodiments of the present invention.

FIG. 6A shows a mold 600 to form a covering and comprising a solid inner component comprising a rigid material placed therein prior to injection of a flowable material. The mold 600 may comprise inner material 110M positioned within the mold as a solid piece of material and outer material 120M comprising a flowable material injected into mold 600 and cured around the preformed piece comprising inner material 600. The mold may comprise an upper portion and a lower portion. In many embodiments, the covering 100 can be formed in a mold with rigid second material 110M2 placed in the mold and encapsulated within a single piece of material comprising first material 110M1, third material 110M3 and outer material 120M, such that first material 110M1, third material 110M3 and outer material 120M comprise the same material, for example silicone. The rigid second material 110M2 may comprise silicone bonded to each of first material 110M1, third material 110M3 and the outer material 120M, for example with curing such that first material 110M1, third material 110M3 and outer material 120M comprise the same soft silicone material bonded to the second material 110M2 comprising rigid silicone.

Figure 7:
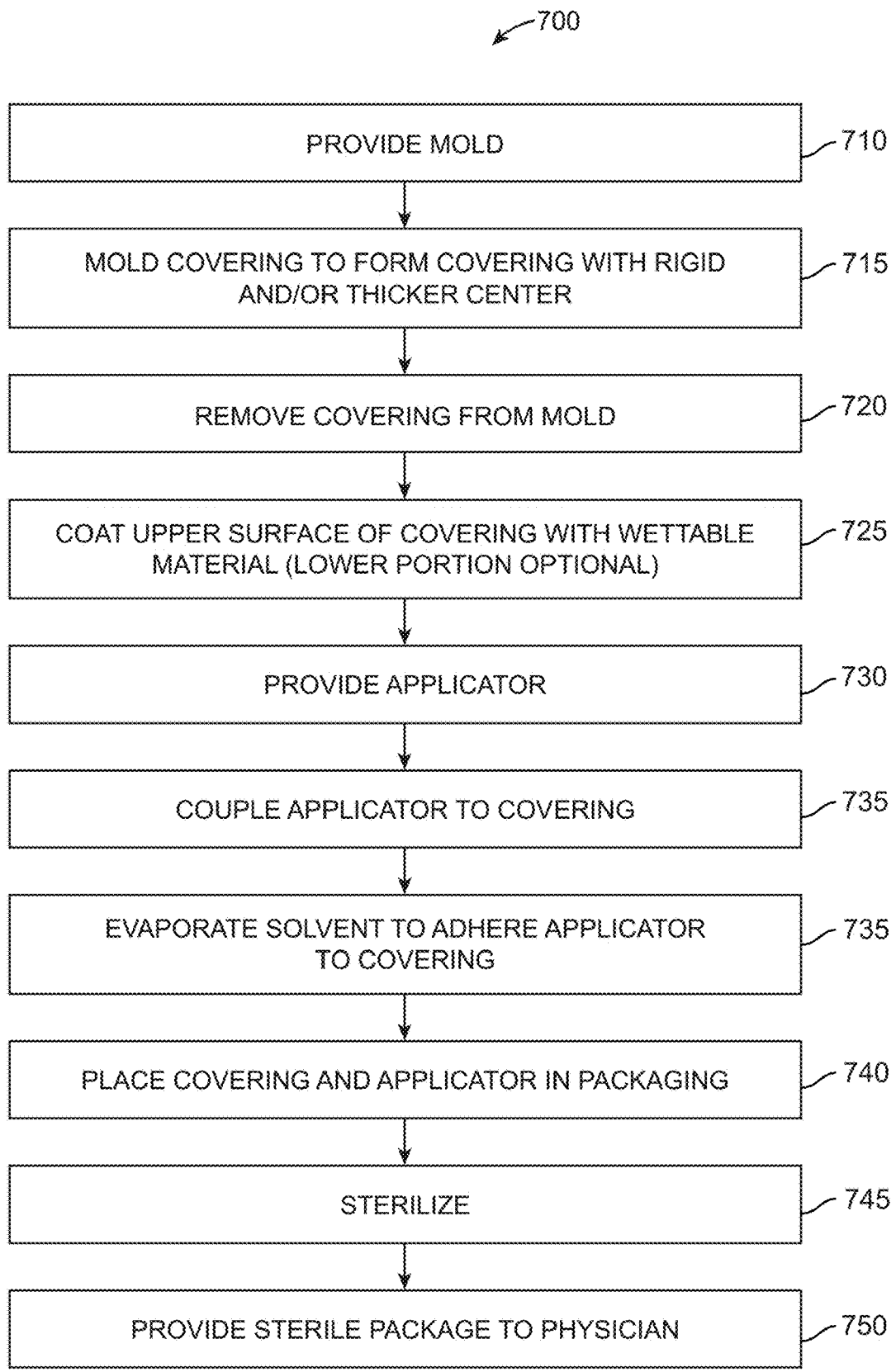
FIG. 7 shows a method of manufacturing a covering with a mold as in FIG. 6, in accordance with embodiments of the present invention.

FIG. 7 shows a method of manufacturing 700 a covering with a mold, for example as described above. A step 710 provides the mold. A step 715 molds the covering to form the covering as described above.

The rigidity and hardness of the molded covering can be determined by one or more of the material hardness, the modulus or the thickness. The molded covering may comprise a covering with an inner center more rigid than the outer periphery, for example, and the center can be thicker than edge. For example, the covering may comprise a single piece covering with an inner portion thicker than the outer portion such that the inner portion is more rigid than the outer portion. Alternatively or in combination, an optically clear inner portion can be molded; the inner portion placed in the mold, and the covering molded to form the outer portion around the inner portion. For example, the molded inner portion comprising layer 110L2 of material 110M2 as described herein, and one or more of layers 110L1 or 110L3 molded around layer 110L2. A step 720 removes covering from the mold. A step 725 coats at least the upper surface of covering with wettable material, and coating of the lower is optional. A step 730 provides the applicator. A step 735 couples the applicator to the covering. A step 735 evaporates solvent so as to adhere applicator to covering. A step 740 places the covering and applicator in packaging. A step 745 sterilizes the contents of the package. A step 750 provides the sterile package to physician.

It should be appreciated that the specific steps illustrated in FIG. 7 provide a particular method of manufacturing a covering, according to an embodiment of the present invention. Other sequences of steps may also be performed according to alternative embodiments. For example, alternative embodiments of the present invention may perform the steps outlined above in a different order. Moreover, the individual steps illustrated in FIG. 7 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 8:
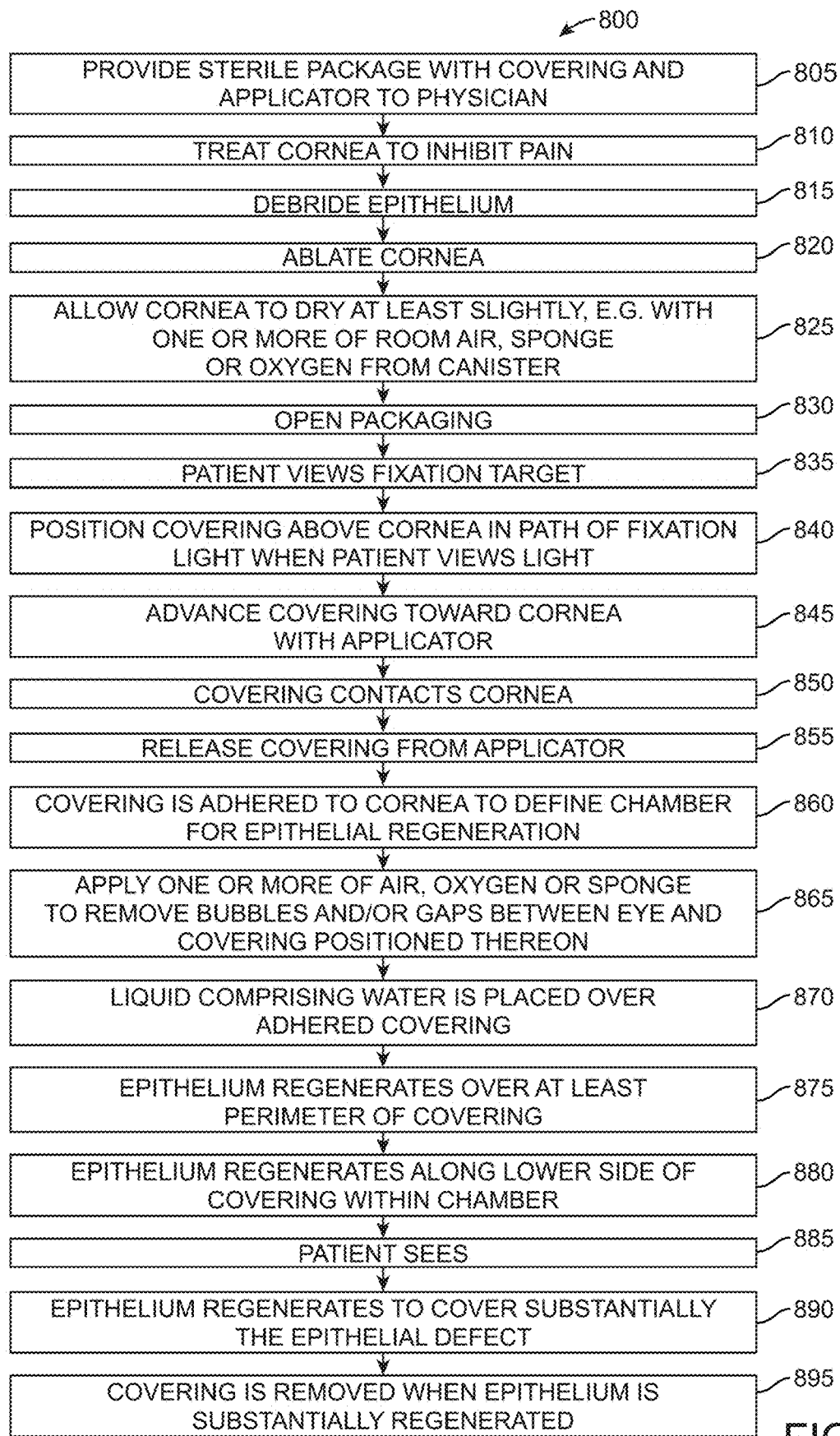
FIG. 8 shows a method of placing a covering on a cornea of an eye, in accordance with embodiments of the present invention.

FIG. 8 shows a method 800 of placing a covering on a cornea of an eye. A step 805 provides the sterile package with covering and applicator to physician. A step 810 treats the cornea to inhibit pain. A step 815 debrides the epithelium. A step 820 ablates the cornea. A step 825 allows the cornea to dry at least slightly, for example with one or more of room air, oxygen or a sponge. The cornea may also be dried with air flow from a pressurized source such as oxygen from a canister. A step 830 opens the packaging. A step 835 fixates the patient visually on the fixation target with viewing of the fixation target. A step 840 positions the covering above cornea in the optical path of the fixation light when patient views light. A step 845 advances the covering toward cornea with the applicator. A step 850 contacts cornea with the covering. A step 855 releases the covering from the applicator, for example ejects covering from the applicator. At step 860, the covering is adhered to the cornea to seal the cornea, for example with one or more of a radius of the covering less than the radius of the cornea, a sticky tacky lower surface of the covering, a substantially conformable outer portion of the covering to seal the cornea, a rigidity of the perimeter of the covering sufficient to abut the epithelium and seal the cornea, for example with deformation of the epithelium, or a conformable portion of the covering disposed over the boundary of the epithelium and the debrided region. A step 865 applies one or more of gas, air, oxygen, or sponge, so as to remove bubbles and/or gaps between the cornea and the covering positioned thereon. At a step 870 a liquid comprising water, for example saline, is applied to the covering and when the covering is sealed on the cornea so as to inhibit swelling. At a step 875, the epithelium regenerates over at least a peripheral portion of the covering, for example over a perimeter of the covering. The epithelium may regenerate toward a center of the covering over the upper surface of the covering. At step 880 the epithelium regenerates along a lower side of the covering within the chamber, for example guided by the lower surface of the covering and the ablated PRK surface. A step 885 allows the patient to see with the covering in position. At a step 890, the epithelium regenerates substantially across the ablated surface, for example with a cell layer comprising at least about 2-3 cells across the ablated surface. At a step 895, the covering is removed when the epithelium is substantially regenerated. The covering can be removed when no substantial visual interference results from removal such that vision is not substantially changed with removal, for example no more than one line of visual acuity.

Work in relation to embodiments suggests that the covering can be left on the cornea with high oxygen permeability for more than a plurality of days, for example at least one week, such as one month or more, such that the epithelium is substantially regenerated across the ablation to a thickness of at least about 40 um and at least about 4-5 cell layers and so as the covering has guided the regeneration of the epithelial and thus provides a smooth epithelium for vision. For example, the covering may remain on the cornea for about one month post PRK ablation to smooth and regenerate the epithelium on the ablation profile with good adherence of the epithelium to the ablation profile and good patient vision.

It should be appreciated that the specific steps illustrated in FIG. 8 provide a particular method of treating a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added or removed depending on the particular applications.

One of ordinary skill in the art would recognize many variations, modifications, and alternatives.

Figure 9:
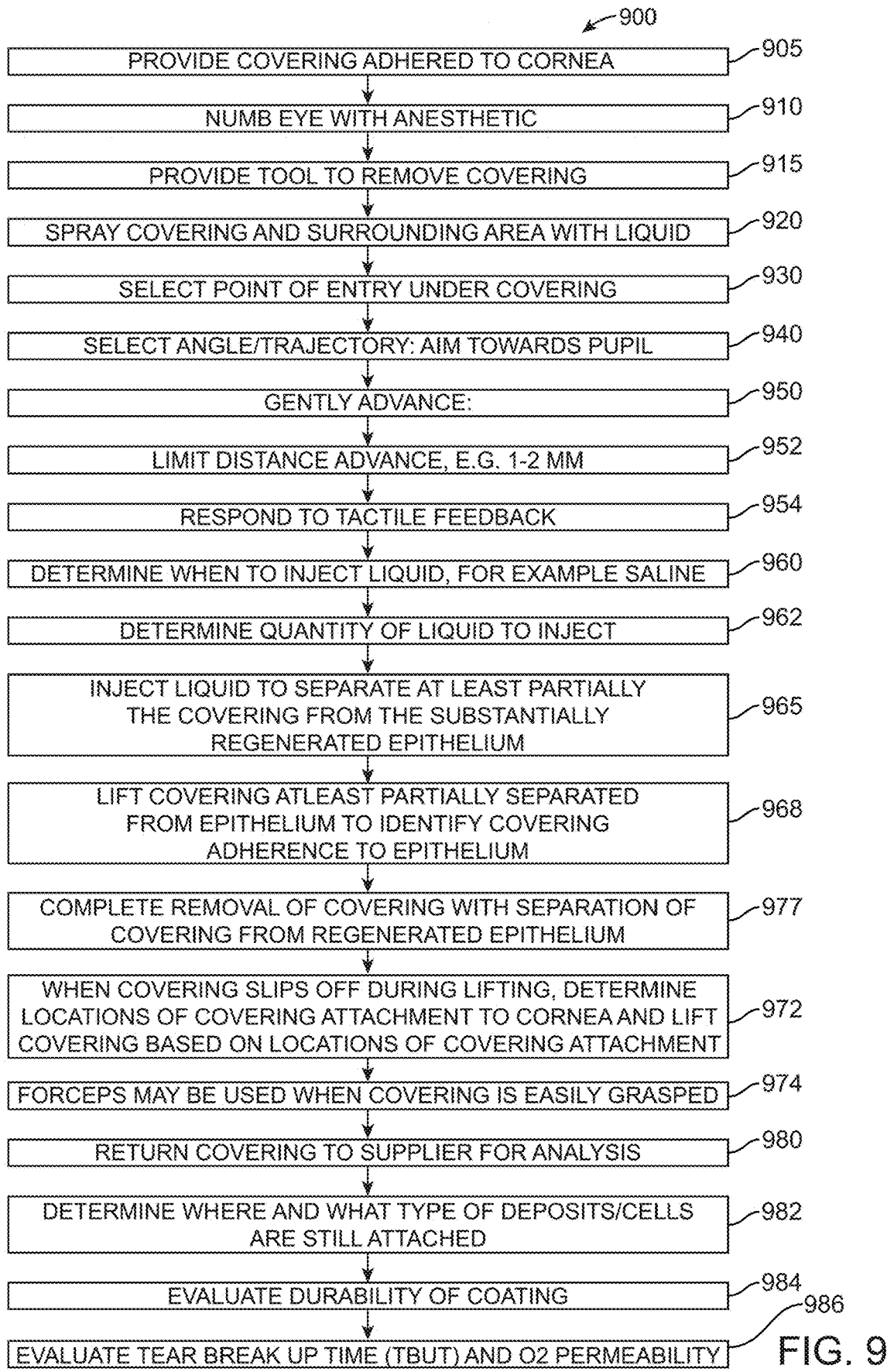
FIG. 9 shows a method of removing a covering from a cornea of an eye, in accordance with embodiments of the present invention.

FIG. 9 shows a method 900 of removing a covering adhered to an epithelium of a patient. A step 905 provides a covering adhered to the cornea of the patient, for example as described above. A step 910 anesthetizes the eye with anesthetic, for example numbs the eye. A step 915 provides a tool to remove the covering. The tool may comprise an elongate structure having a lumen to extend under the covering and pass the liquid under the covering, for example a hydro-dissection tool. A step 920 sprays the covering and surrounding area of the cornea with liquid. A step 930 identifies, for example selects, a location of entry under the covering, for example a point of entry under the covering. A step 940 identifies and an orientation, for example selects and angel and trajectory, to advance the removal tool inwardly, for example toward the pupil. A step 950 gently advances the removal tool. A sub-step 952 limits the distance the tool is advanced to 1-2 mm. A sub-step 954 responds to tactile feedback so as to limit advancement of the tool under the covering. A step 960 determines when to inject the liquid under the covering, for example saline. A step 962 determines a quantity of liquid to inject. A step 965 injects the liquid to separate at least partially the covering from the substantially regenerated epithelium. A step 968 lifts the covering when the covering is at least partially separated from the epithelium. The lifting of the covering can identify further separate the covering from the epithelium so as to identify adherence of the covering to the epithelium, for example locations of adherence of the covering to the epithelium.

A step 970 completes removal of the covering with separation of the covering from the substantially regenerated epithelium. A sub-step 972 determines locations of covering attachment to the cornea, for example when the covering slips. The covering can be lifted further based on the attachment locations. A sub-step 974 may use forceps to remove the covering.

A step 980 returns the covering to the supplier for analysis. A sub-step 982 determines where and what type of material and/or cells the deposits comprise and whether cells of the epithelium remain attached to the covering. A sub-step 984 evaluates durability of the covering. A sub-step 986 evaluates the tear break up time (hereinafter "TBUT") and oxygen (hereinafter "O02") permeability of the covering.

It should be appreciated that the specific steps illustrated in FIG. 9 provide a particular method of removing a covering from a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 9 may include multiple sub-steps that may be performed in various sequences as appropriate to the individual step. Furthermore, additional steps may be added or removed depending on the particular applications. One of ordinary skill in the art would recognize many variations, modifications, and alternatives.

The method 700, the method 800 and the method 900 can be combined. For example a covering can be manufactured in accordance with method 700 and provided to the physician, the covering placed in accordance with method 800, and the covering removed in accordance with the method 900.

Experimental

Based on the teachings described herein, a person of ordinary skill in the art can conduct experiments and clinical studies to determine sealing of the cornea with the covering to promote epithelial regeneration and improved vision.

Clinical studies to determine smoothing of corneal irregularities with the covering.

A clinical study was conducted to determine smoothing of corneal irregularities using the covering with dimensions as described above with reference to FIGS. 1C1, 1G1A to 1G1H and a rigid inner portion and softer outer portion as shown with reference to FIGS. 1C1.

The clinical study included images from at least 10 patients that showed consistent smoothing of the front surface of the covering as compared to the front surface of the cornea.

Figure 10A:
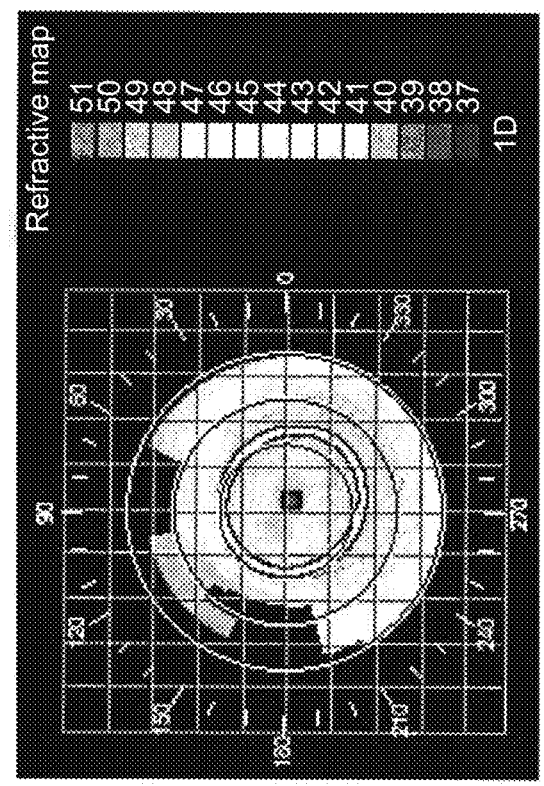
FIG. 10A shows corneal topography and smoothing of epithelial irregularities with the covering, in accordance with embodiments of the present invention.
Figure 10A:
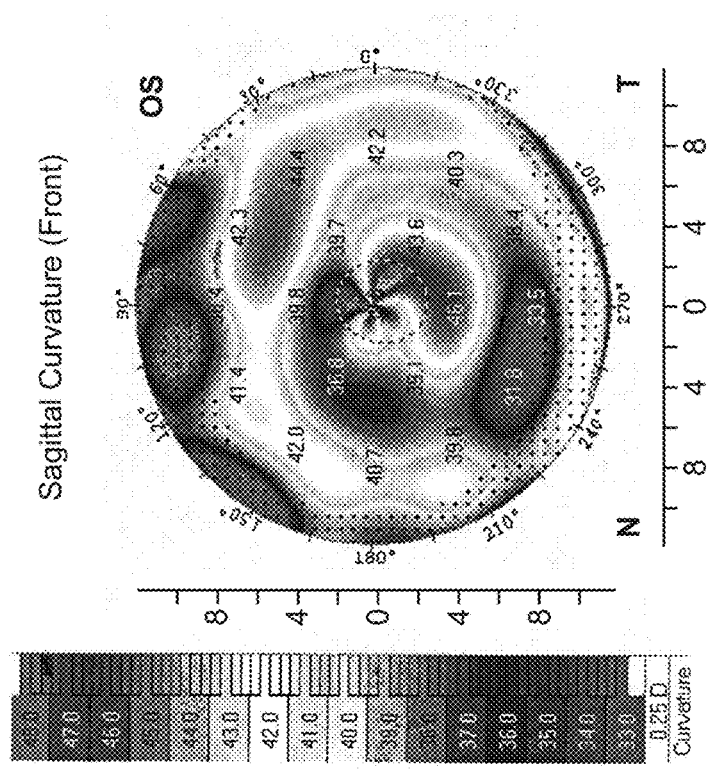

FIG. 10A shows corneal topography and smoothing of epithelial irregularities with the covering at 24 hours post-op. The Pentacam™ image shows the profile of the front surface of the cornea comprising the epithelium, the epithelial defect and ablated stroma. The commercially available Pentacam comprises Scheimpflug camera and prism to profile the front surface of the cornea when the covering is positioned on the cornea. The central portion of the ablated stroma profile comprises an irregularity referred to as a central island having a steep curvature corresponding to an optical power of about 46D surrounded by flatter portions of the ablated cornea having a curvature corresponding to an optical power of about 40D. The EyeSys™ refractive map comprises a front surface refractive map of the optical power of the covering when the covering is positioned over the irregularities shown in the Pentacam™ image. The refractive map shows a much smoother surface having a curvature corresponding to a refractive power of about 43D at 3 mm, 44D at 5 mm and 44D at 7 mm. Based on these images the front surface of the covering is substantially smoother than the underlying epithelium.

Figure 10B:
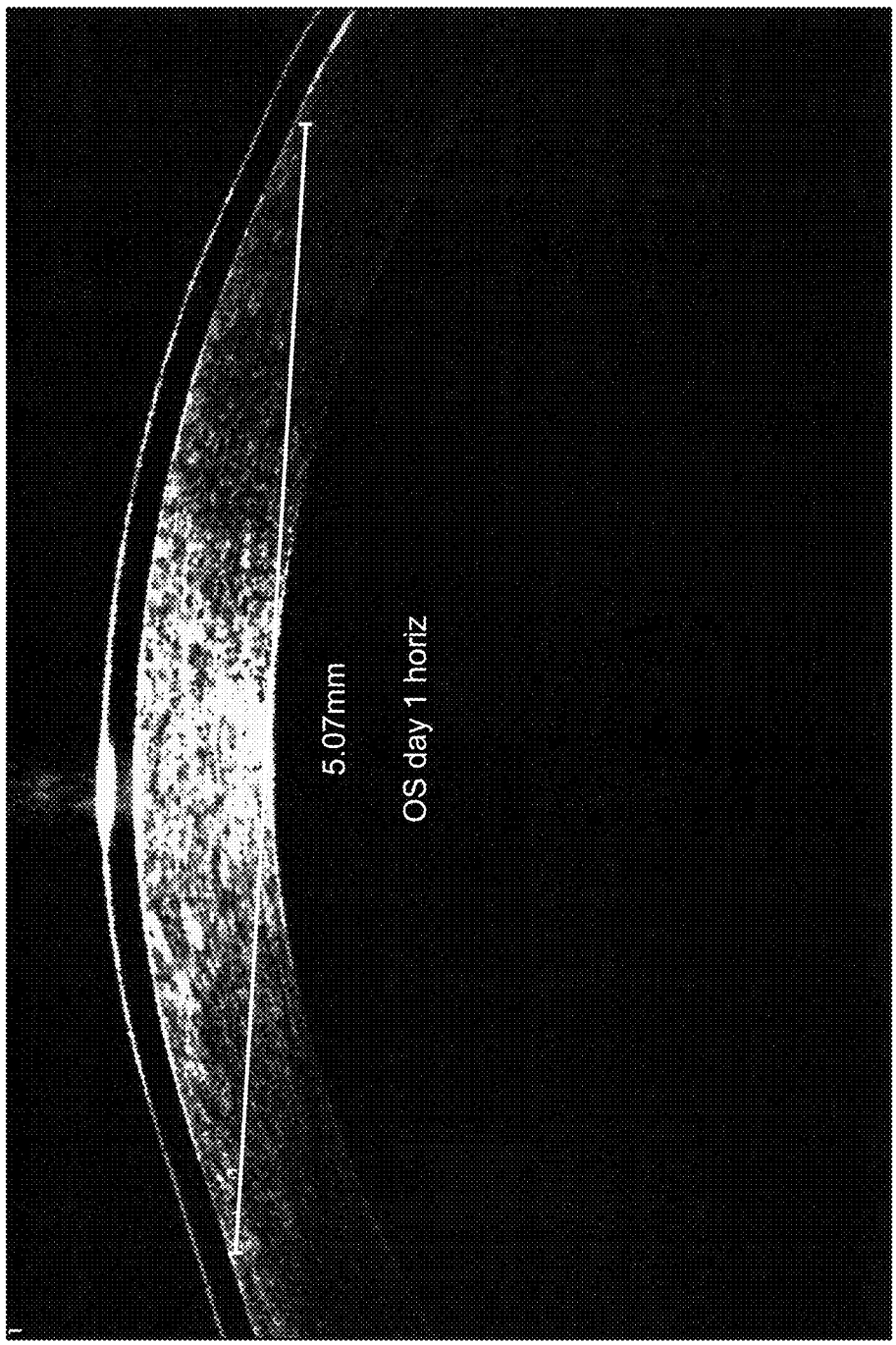
FIGS. 10B, 10C and 10D show, horizontal, vertical and central OCT images, respectively, of the covering on the eye of FIG. 10A without a gap disposed between the covering and the cornea such that the covering directly contacts the ablated stroma and regenerating epithelium.
Figure 10C:
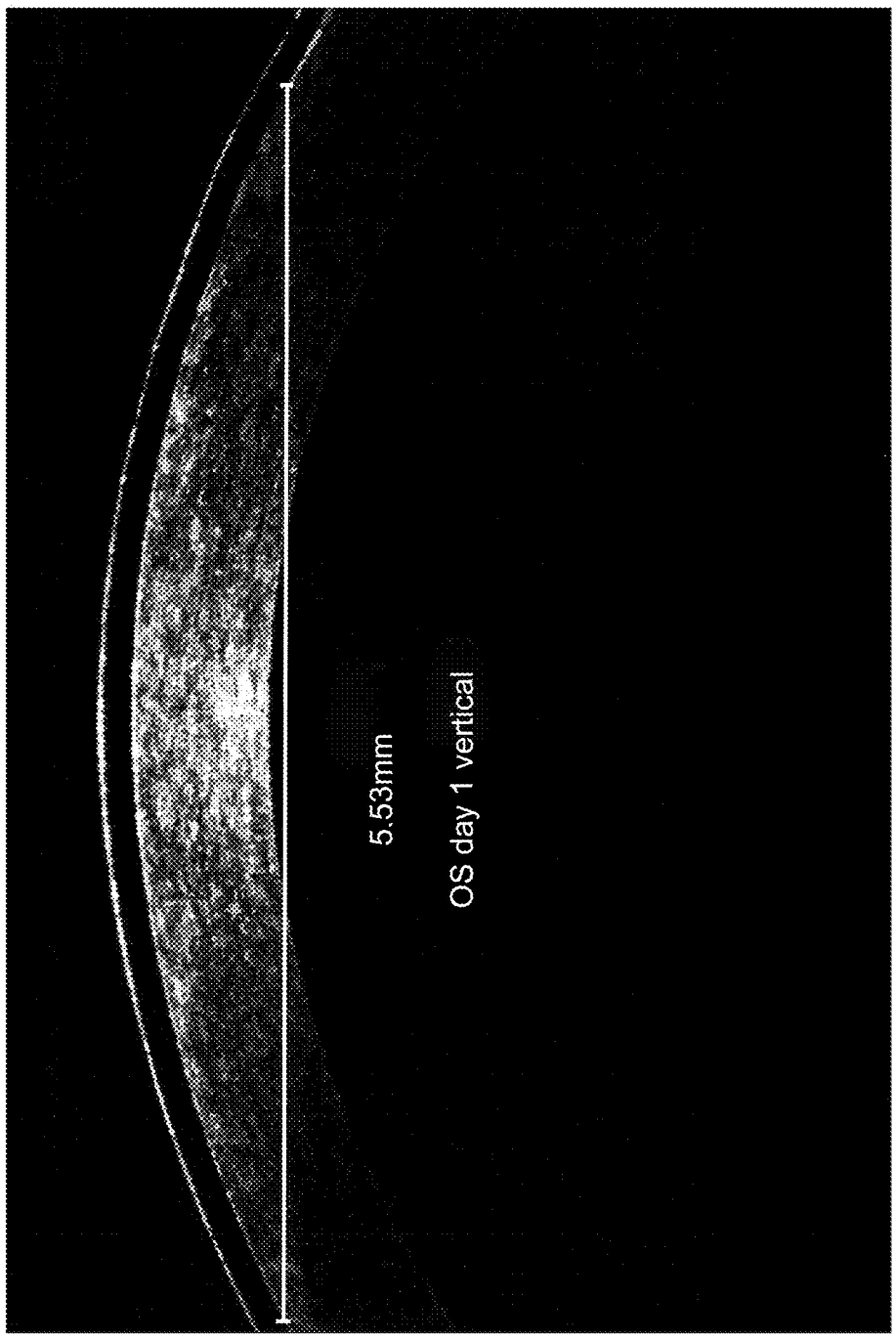
Figure 10D:
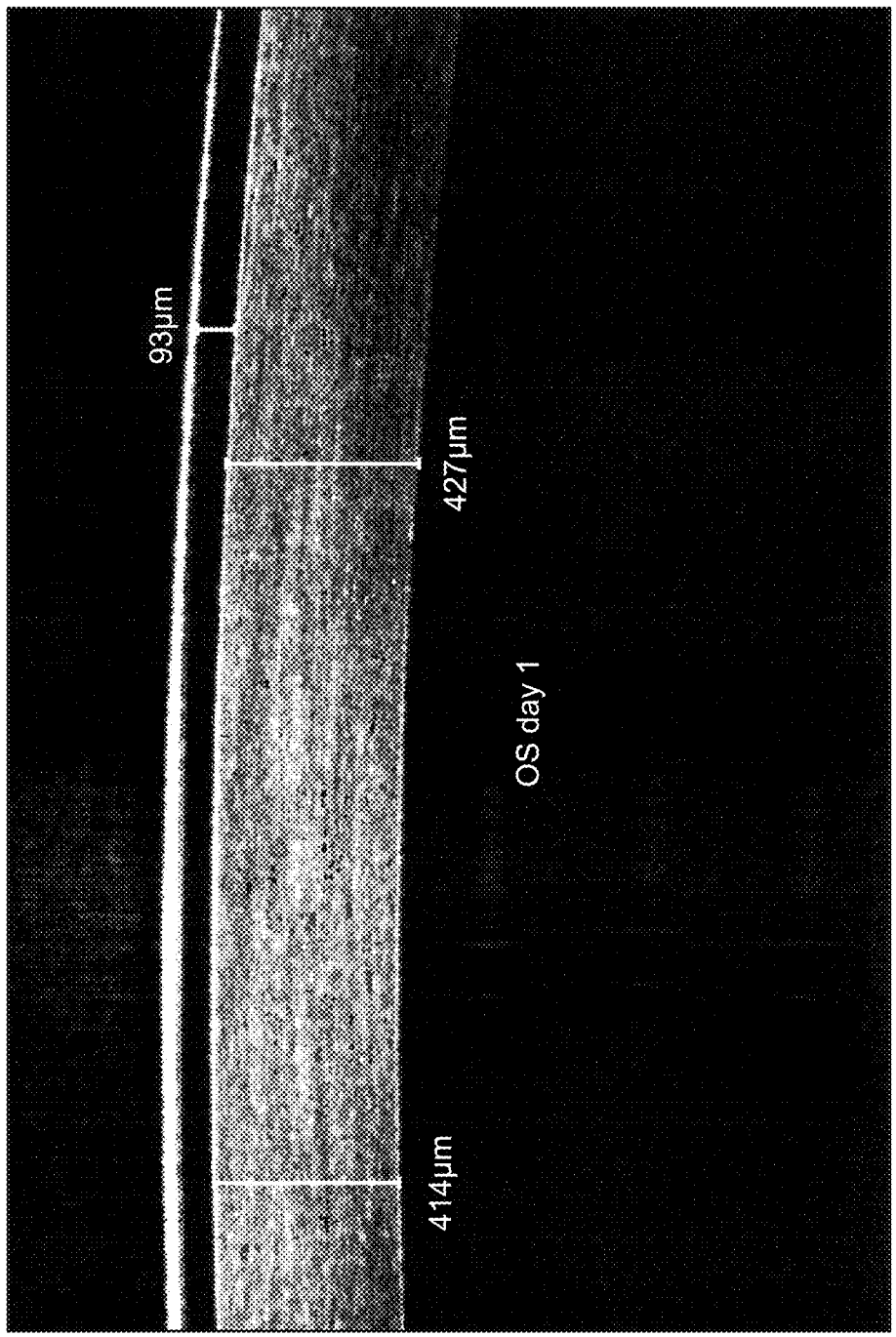

FIGS. 10B, 10C and 10D show horizontal, vertical and central OCT images, respectively, of the covering on the eye of FIG. 10A without a gap disposed between the covering and the cornea such that the covering directly contacts the ablated stroma and regenerating epithelium. FIGS. 10B and 10C show an advance edge of the regenerating epithelium. FIG. 10D shows the thickness of the central portion of about 93 um and an ablated corneal thickness of about 427 um and 414 um. Each of these images show direct contact of the covering to the cornea and no gap appears between the covering and the cornea.

Similar images have been obtained at 48 and 72 hours post-op and show smoothing of the covering, and that the central island of the cornea decreases with time.

Images similar to 10A to 10D have been obtained and show smoothing with a majority of patients, such that the covering with tear smooth the irregularities of the cornea. The wettable surface coating of the front surface can provide a tear on the front surface to smooth irregularities transferred to the covering.

Clinical Studies to Seal the Covering on the Cornea.

The clinical studies described herein show sealing of the cornea and smoothing of the epithelial defects of the study. Based on the embodiments describe herein, a person of ordinary skill in the art can conduct additional studies to determine the rigidity of the outer portion of the covering to facilitate removal and seal the cornea. Additional studies can be conducted to determine the conformability of the inner portion to correct vision, for example with the ablated stroma as described above. Additional studies may be conducted so as to improve reepithelialization rates. Such studies can be conducted separately or in combination, in accordance with the embodiments studied, as described herein.

A clinical study was conducted to determine the effect of covering rigidity on sealing of the covering with the cornea and epithelial shaping near the perimeter of the covering. Two sets of coverings were prepared from silicone resin. Each set was coated with a luminous chemical vapor deposition such that the upper surface comprised a wettable surface. The coverings had substantially the same shape in accordance with the dimensions FIGS. 1G1A to 1G1H. The total diameter across was about 10 mm. The inner portion comprised a diameter of about 6 mm. An annular rim of extended around the perimeter of the covering with a thickness of about 35 um. The annular rim comprised an inner diameter of 9 mm and an outer diameter of 10 mm corresponding to the perimeter of the covering. The annular rim comprised a width of 0.5 mm extending circumferentially around the covering. The outer portion comprised the rim and a taper that extended from inner portion to the rim. The taper in thickness was substantially uniform between the outer diameter of the inner portion at 6 mm diameter and the inner diameter of the rim at 9 mm. The central portion comprised a substantially uniform thickness of about 100 um. The outer rim comprised substantially uniform thickness of about 0.35 um. The base radius of curvature of the lower surface of the covering was about 7.5 mm. The upper surface of the covering comprised a radius of curvature of about 7.529 mm, such that the covering was substantially uniform with no substantial refractive power.

The first set of coverings comprised single piece silicone elastomer coverings having Shore A hardness of about 40 (hereinafter "Group I"), for example about 45, and the second set comprised single piece silicone elastomer coverings having a Shore A hardness of about 85 (hereinafter "Group II"). The Shore A hardness of Group I corresponds to a soft covering, and the Shore A harness of Group II corresponds to a rigid covering. The covering comprises a shield that protects the cornea. Both silicone coverings were coated with an LCVD coating on the upper (anterior) surface and the lower surface comprised a sticky tacky silicone surface to adhere to the cornea.

The OCT images of the eyes show an increased epithelial covering on the perimeter of the corresponding to an inferior location on the eye of the patient and a decreased covering the perimeter of the covering superiorly. The chamfer abuts the epithelium so as to deflect the epithelium and form an indentation in the epithelium to seal the cornea. The following images are substantially representative and show sealing of the epithelial defect of the cornea following PRK. The hours refers to the hours post-PRK.

FIGS. 11A1A to 11A1D show OCT images of portions of the soft covering from, respectively, the superior portion of the covering, the nasal portion of the covering, the temporal portion of the covering and the inferior portion of the covering at 48 hours post-op on the right eye (OD).

FIGS. 11A2A to 11A2D show OCT images of portions of the soft covering from, respectively, the superior portion of the covering, the nasal portion of the covering, the temporal portion of the covering and the inferior portion of the covering at 48 hours post-op on the left eye (OS).

FIGS. 11A3A to 11A3D show OCT images of portions of the soft covering from, respectively, the superior portion of the covering, the nasal portion of the covering, the temporal portion of the covering and the inferior portion of the covering at 72 hours post-op on the right eye (OD).

FIGS. 12A1A to 12A1C show OCT images of portions of the rigid covering from, respectively, the temporal portion of the covering, the nasal portion of the covering and the inferior portion of the covering at 24 hours post-op on the right eye (OD).

FIGS. 12A2A to 12A2D show OCT images of portions of the rigid covering from, respectively, the superior portion of the covering, the temporal portion of the covering, the nasal portion of the covering and the inferior portion of the covering at 48 hours post-op for on the left eye (OS).

FIGS. 12A3A to 12A3D show OCT images of portions of the rigid covering from, respectively, the superior portion of the covering, the temporal portion of the covering, the nasal portion of the covering and the inferior portion of the covering at 72 hours post-op on the left eye (OS).

The soft shields show less covering of the outer portion with the epithelium than the rigid coverings. In some of the above examples with the rigid shield, the chamfer of the rigid portion extends substantially into the epithelium and may contact Bowman's membrane in at least some instances. While effective in sealing the covering, work in relation to embodiments suggests that less covering of the outer portion can facilitate removal.

Additional studies are contemplated to determine the hardness and rigidity to seal the cornea uniformly with hardness parameter that can be intermediate to those tested as described above. For example, additional studies are contemplated to determine the perimeter suitable for substantially uniform covering of the epithelium around the covering, for example with a variable rigidity perimeter as described above. Also, studies can be conducted with the coating disposed over the silicone to determine the promotion of epithelial growth with the environment provided high Dk covering and sealing. Work in relation to embodiments indicates that the epithelium of a majority of patients can regenerate substantially within two days post-PRK to cover the ablated stroma, for example with the LCVD coating on silicone and the shape tested in the embodiments 11A1A to 12A3D. Testing of the oxygen permeability Dk parameter of these LCVD on silicone embodiments indicates that the Dk can exceed 400, so as to substantially promote regeneration of the epithelium.

Clinical Studies of Patients after PRK.

Experimental studies have been conducted to determine the improvement in vision with therapeutic coverings as described herein. A series of patents was treated with PRK and the patients received a either commercially available bandage contact lens (BL) or a therapeutic covering (TC) as described herein. The study design and protocol was in accordance with the study designs and protocols described in published U.S. patent application Ser. No. 12/384,659, filed Apr. 6, 2009, entitled "Therapeutic Device for Pain Management and Vision", the full disclosure of which has been previously incorporated by reference and suitable for combination in accordance with some embodiments of the present invention as described herein. The therapeutic covering as described herein comprised molded elastomeric silicone lenses formed with a mold shaped in accordance with FIGS. 1G to 1G1H above. The elastomeric lens was treated with LCVD as described herein. The molded elastomeric silicone lenses comprised a modulus within a range from about 4 to about 20 MPa, a Dk of at least about 150, a water content of no more than about 10%, and a low ion permeability. The clinical results are shown in Table I below.

TABLE I

| Clinical results with therapeutic covering following PRK. | | | |
|---|---|---|---|
| % 20/40 (6/12) or Better | 24 hours | 48 hours | 72 hours |
| PRK (BL) | 25% (n = 24) | 29% (n = 24) | 66% (n = 12) |
| PRK (TC) | 100% (n = 13) | 92% (n = 13) | 100% (n = 13) |

The data of Table I show patient visual acuity for the patients with the commercially available bandage lens (BL) and the therapeutic covering (TC) as described herein at 24, 48 and 72 hours, respectively. At all time points, at least about 92% of the TC patients were 20/40 or better. The TC patient population had 100%, 92% and 100% of patients 20/40 or better at 24, 48 and 72 hours post-op, whereas the BL patient population had 25%, 29% and 66% of patients 20/40 or better, at 24, 48 and 72 hours post-op respectively. These data show that the therapeutic covering as described herein can improve visual acuity in individual patients of a population of patients having PRK and that the therapeutic covering provides better visual acuity for an individual patient than if the patient had not received the covering. Although the above data were obtained with a sample size of 24 patients in the BL ground and 13 patients in the TC group, additional studies can be undertaken by a person of ordinary skill in the art, in accordance with the teachings described herein.

The embodiments as described herein can be combined in many ways. As used herein like alphanumeric characters describe like structures and methods and are interchangeable among the figures and supporting text in accordance with the embodiments described herein.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A covering to treat an eye of a patient, wherein,
the eye comprises a cornea, an ablated stroma, and an epithelium, wherein the epithelium comprises an inner portion comprising irregularities characterized by an irregularity profile and an outer portion;
the covering comprises a conformable inner portion comprising an upper surface profile;
the covering comprises an outer portion configured to adhere to the outer portion of the epithelium; and
the upper surface profile corresponds to a profile of the ablated stroma and is configured to smooth the irregularities when the outer portion of the covering adheres to the outer portion of the epithelium,
wherein the irregularities comprise high spatial frequencies and the conformable inner portion is configured to smooth the high spatial frequencies, and
wherein the high spatial frequencies correspond to frequencies greater than 0.17 cycles/mm.

2. The covering of claim 1, wherein,
the irregularity profile comprises spatial frequencies;
the upper surface profile comprises spatial frequencies; and
the upper surface profile spatial frequencies are lower than the spatial frequencies of the irregularity profile.

3. The covering of claim 1, wherein the conformable inner portion comprises a stretchable material configured to stretch across the irregularities of the epithelium and to smooth the irregularities transferred from the irregularity profile in contact with the lower surface to the upper surface profile when the outer portion of the covering is adhered to the outer portion of the epithelium.

4. The covering of claim 1, wherein the conformable inner portion comprises a stretchable material having a thickness profile configured to smooth the irregularities of the epithelium when the covering is positioned on the cornea.

5. The covering of claim 1, wherein the inner portion comprises a compressible material to conform to the irregularities of the epithelium with a lower surface and smooth irregularities transferred from the irregularity profile in contact with the lower surface to the upper surface profile when the outer portion is adhered to the epithelium.

6. The covering of claim 1, wherein the covering comprises a material having a modulus within a range from 4 MPa to 20 MPa.

7. The covering of claim 1, wherein the covering comprises a material selected from a silicone hydrogel, silicone, and a combination thereof.

8. The covering of claim 1, wherein the inner portion of the covering comprises an optical power that is from 1D to 2.5D less than the optical power of the ablated stroma.

9. A covering to treat an eye of a patient, wherein,
the eye comprises a cornea, an ablated stroma, and an epithelium, wherein the epithelium comprises an inner portion comprising irregularities characterized by an irregularity profile and an outer portion;
the covering comprises a conformable inner portion comprising an upper surface profile;
the covering comprises an outer portion configured to adhere to the outer portion of the epithelium; and
the upper surface profile corresponds to a profile of the ablated stroma and is configured to smooth the irregularities when the outer portion of the covering adheres to the outer portion of the epithelium,
wherein the inner portion of the covering comprises an optical power that is from 1D to 2.5D less than the optical power of the ablated stroma.

10. The covering of claim 9, wherein,
the irregularity profile comprises spatial frequencies;
the upper surface profile comprises spatial frequencies; and
the upper surface profile spatial frequencies are lower than the spatial frequencies of the irregularity profile.

11. The covering of claim 9, wherein the conformable inner portion comprises a stretchable material configured to stretch across the irregularities of the epithelium and to smooth the irregularities transferred from the irregularity profile in contact with the lower surface to the upper surface profile when the outer portion of the covering is adhered to the outer portion of the epithelium.

12. The covering of claim 9, wherein the conformable inner portion comprises a stretchable material having a thickness profile configured to smooth the irregularities of the epithelium when the covering is positioned on the cornea.

13. The covering of claim 9, wherein the inner portion comprises a compressible material to conform to the irregularities of the epithelium with a lower surface and smooth irregularities transferred from the irregularity profile in contact with the lower surface to the upper surface profile when the outer portion is adhered to the epithelium.

14. The covering of claim 9, wherein the covering comprises a material having a modulus within a range from 4 MPa to 20 MPa.

15. The covering of claim 9, wherein the covering comprises a material selected from a silicone hydrogel, silicone, and a combination thereof.

16. The covering of claim 9, wherein the irregularities comprise high spatial frequencies and the conformable inner portion is configured to smooth the high spatial frequencies.

* * * * *